(12) United States Patent
Nishimura et al.

(10) Patent No.: US 8,877,454 B2
(45) Date of Patent: Nov. 4, 2014

(54) APPARATUS FOR AUTO-PRETREATING SUGAR CHAIN

(75) Inventors: Shinichiro Nishimura, Hokkaido (JP); Yasuro Shinohara, Hokkaido (JP); Yoshiaki Miura, Hokkaido (JP); Hiroshi Yamazaki, Tokyo (JP); Michio Horiuchi, Tokyo (JP); Hiroaki Motoki, Tokyo (JP); Toshiharu Kuroda, Tokyo (JP); Yoko Kita, Hyogo (JP); Mika Nakano, Hyogo (JP)

(73) Assignees: National University Corporation Hokkaido University, Sapporo-Shi, Hokkaido (JP); Shionogi & Co., Ltd., Chuo-Ku, Osaka (JP)

(*) Notice: Subject to any disclaimer, the term of this patent is extended or adjusted under 35 U.S.C. 154(b) by 926 days.

(21) Appl. No.: 12/681,573

(22) PCT Filed: Oct. 3, 2008

(86) PCT No.: PCT/JP2008/068111
§ 371 (c)(1),
(2), (4) Date: Dec. 3, 2010

(87) PCT Pub. No.: WO2009/044900
PCT Pub. Date: Apr. 9, 2009

(65) Prior Publication Data
US 2011/0111443 A1 May 12, 2011

(30) Foreign Application Priority Data

Oct. 5, 2007 (JP) ................................. 2007-262680
Oct. 5, 2007 (JP) ................................. 2007-262771

(51) Int. Cl.
*C12Q 1/37* (2006.01)
*G01N 33/68* (2006.01)
*G01N 30/72* (2006.01)
*H01J 49/00* (2006.01)

(52) U.S. Cl.
CPC ........ *G01N 33/6848* (2013.01); *G01N 30/7233* (2013.01); *G01N 2400/00* (2013.01); *H01J 49/00* (2013.01)
USPC .................................... 435/23; 435/4; 435/22

(58) Field of Classification Search
CPC ................................................. G01N 30/7233
USPC ................................................. 435/4, 22, 23
See application file for complete search history.

(56) References Cited

FOREIGN PATENT DOCUMENTS

| JP | 2005291958 | 10/2005 |
|---|---|---|
| WO | WO-2006112771 | 10/2006 |
| WO | WO2007099856 | 9/2007 |

OTHER PUBLICATIONS

Uematsu et al. "High throughput quantitative glycomics and glycoform-focused proteomics of murine dermis and epidermis", Molecular & Cellular Proteomics, 2005, 4:1977-1989.*
Shimaoka et al "One-pot solid-phase glycoblotting and probing by transoximization for high-throughput glycomics and glycoproteomics", Chem. Eur. J., 2007, 13:1664-1673.*
Schlosser et al "Combination of solid-phase affinity capture on magnetic beads and mass spectrometry to study non-covalent interactions: example of minor groove binding drugs", Rapid Communications in Mass Spectrometry, 2005, 19:3307-3314.*
Powell et al. "Stabilization of sialic acids in N-linked oligosaccharides and gangliosides for analysis by positive ion matrix-assisted laser desorption/ionization mass spectrometry", Rapid Commun. in mass spectrometry, 1996, 10:1027-1032.*
Kita et al., "Quantitative glycomics of human whole serum glycoproteins based on the standardized protocol for liberating N-glycans," Molecular and Cellular Proteomics, 6(8):1437-1445 (2007).
Miura et al., "Rapid and simple solid-phase esterification of sialic acid residues for quantitative glycomics by mass spectrometry," Chemistry—A European Journal, 13(17):4797-4804 (2007).
Yu et al., "A rapid sample preparation method for mass spectrometric characterization of N-Linked glycans," *Rapid Communications in Mass Spectrometry*, 19(16):2331-2336 (2005).
Nishimura et al., "High-throughput protein glycomics: Combined Use of Chemoselective Glycoblotting and MALDI-TOF/TOF Mass Spectrometry," Angew. Chem. Int. Ed., 44(1):91-96 (2005).

* cited by examiner

*Primary Examiner* — Bin Shen
(74) *Attorney, Agent, or Firm* — Ropes & Gray LLP; James F. Haley, Jr.; Brian M. Gummow

(57) ABSTRACT

To provide an autoanalyzer for analyzing a sugar chain contained in a biological sample, in particular, serum. Namely, it is intended to provide a method of analyzing a sugar chain in a sample, which comprises the following steps: A) the sugar chain-releasing step of releasing the sugar chain in the sample; B) the detection sample-preparing step of preparing the released sugar chain for detection; and, in the case of conducting mass spectrometry using a plate, C) the step of forming a plate for the mass spectrometry having the captured sugar chain dotted thereon which comprises the step of providing the tagged sugar chain sample solution obtained in the step B) on a collection plate; and, if required, the step of conducting an operation in a solid phase support-enclosed plate to form the plate for mass spectrometry; and D) the step of analyzing the sugar chain to be assayed.

4 Claims, 42 Drawing Sheets

Prior Art

Prior Art

Fig.7
Injection from plate for recovery #1 to MALDI PLATE
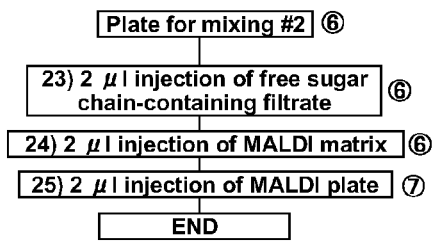
Injection to MALDI plate after SPE treatment
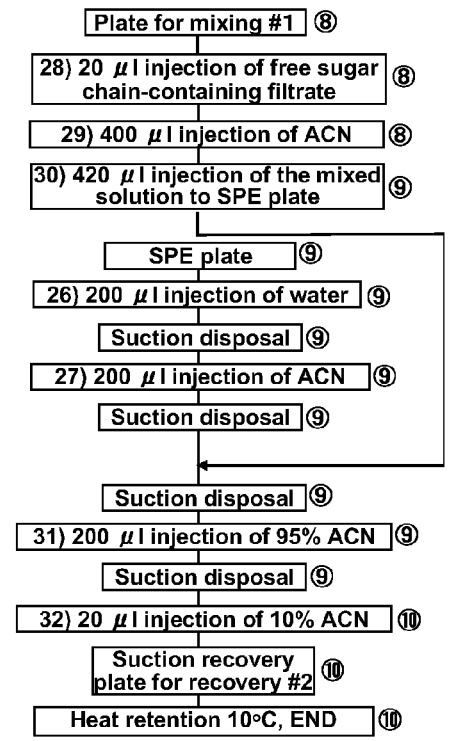
Injection from plate for recovery #2 to MALDI plate (after SPE treatment)
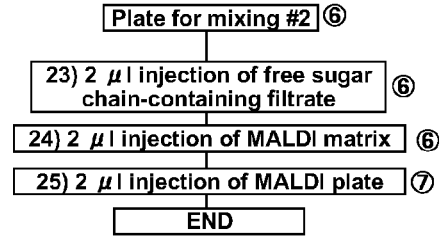

Flow chart for BlotGlycoABC

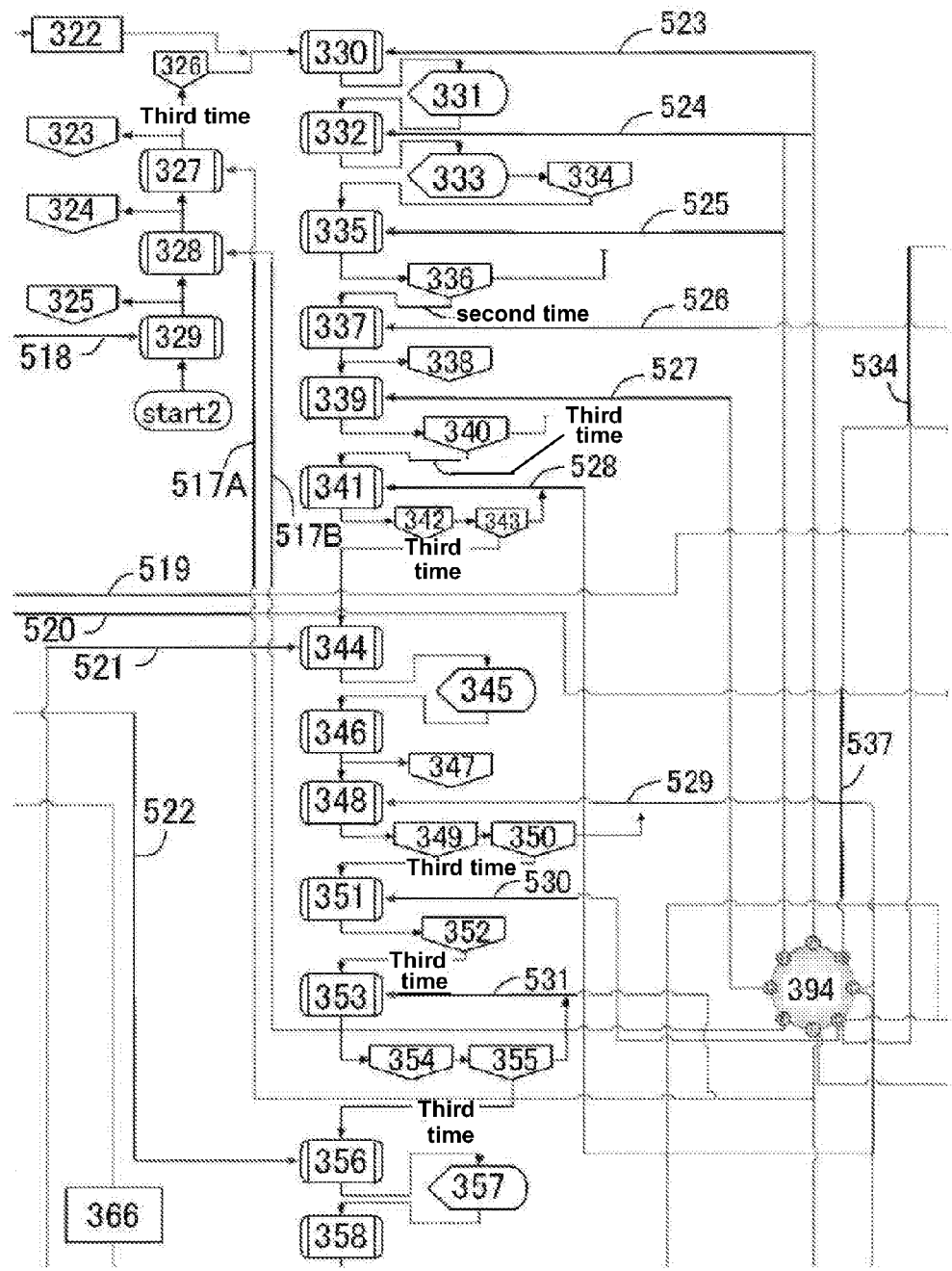

MALDI-TOFMS spectrum of serum sample (n=8)
prepared by the automatic glycoblotting protocol using
BlotGlycoABC™

APPARATUS FOR AUTO-PRETREATING SUGAR CHAIN

TECHNICAL FIELD

The present invention relates to an apparatus for sugar chain analysis. The present invention can be applied to the diagnosis of a disease, or the like. More particularly, the present invention relates to an automatic sugar chain pretreatment apparatus.

BACKGROUND ART

Pretreatment methods for quantitatively analyzing a sugar chain (Patent Document 1; Non-Patent Document 1). There has been reported a method of detecting a sugar chain rapidly with high sensitivity in order to rapidly analyze the sugar chain, by selectively capturing only a sugar chain released from a glycoprotein, immobilizing the sugar chain on beads, and washing the bead (Non-Patent Document 2). However, an apparatus or pretreatment apparatus that automatically performs a sugar chain analysis using a large amount of a sample such as a blood serum sample, is not known yet.

In the conventional art, purification of a sugar chain contained in a biologically derived mixture of a body fluid such as blood (serum) and a cell/tissue extract, is carried out according to the following steps.

A. A glycoprotein in a sample is reductively alkylated in the presence of a soluble product.

B. A proteolytic enzyme is added thereto to digest the protein moiety with the enzyme, and then the system is heated to deactivate the enzyme.

C. An enzymatic treatment or a chemical treatment which releases a sugar chain from a peptide is carried out to release the sugar chain.

D. Polymer beads displaying a functional group capable of capturing a sugar chain are contacted with a sample which has been finished with the treatment of item C., and thereby the released sugar chain is captured by the functional group of polymer beads.

E. The sample is washed and filtered to remove those impurities that are not captured by the functional group of the polymer beads.

F. The carboxylic acid of a sialic acid residue of the sugar chain captured by the functional group of the polymer beads, is protected by methyl esterifying the functional group.

G. The sugar chain captured by the functional group of the polymer beads is subjected to a reduction of the hydrazone bond to stabilize the binding thereof with the polymer beads.

H. The sugar chain is released from the polymer beads through a hydrazone-oxime exchange reaction, by cleaving the disulfide bond included in sugar chain capturing molecules on beads, or by dispensing an aminooxy-containing compound. In the case of the latter, the treatment of item G. is not carried out.

I. The released sugar chain is recovered in a filtrate.

J. A MALDI matrix is added to the sugar chain-containing filtrate, and then the mixture is added dropwise on a MALDI plate.

Patent Document 1: WO 2004/058687
Non-patent Literature 1: Mol. Cell. Proteomics. 2007; 6:1437-45. Quantitative glycomics of human whole serum glycoproteins based on the standardized protocol for liberating N-glycans. Kita Y, Miura Y, Furukawa J, Nakano M, Shinohara Y, Ohno M, Takimoto A, Nishimura S.
Non-patent Literature 2: Chem. Euro. J. 2007; 13:4797-804. Rapid and simple solid-phase esterification of sialic acid residues for quantitative glycomics by mass spectrometry. Miura Y, Shinohara Y, Furukawa J. Nagahori N, Nishimura S.

DISCLOSURE OF THE INVENTION

Problem to be Solved by the Invention

However, conventionally, such processes have been carried out mostly by hand, and thus these processes have required extensive time and labor, while it has been difficult to carry out purification with high accuracy.

The present invention was made under such circumstances, and is intended to provide an automatic sugar chain pretreatment apparatus which allows purification to be carried out at high speed with high accuracy by automating the treatment processes.

That is, it is an object of the present invention to provide an auto-analyzing apparatus for analyzing a sugar chain contained in a blood serum sample. It is an object to make it possible by the auto-analyzing apparatus to automatically analyze a large amount of sample simultaneously. In order to release a sugar chain quantitatively from a glycoprotein, cumbersome pretreatments such as a use of a solubilizing agent, reductive alkylation and digestion by trypsin, are required. Furthermore, a sugar chain that has been quantitatively released can be subjected to a rapid analysis of the sugar chain by performing chemoselective capturing and thereby easily removing troublesome foreign matters. However, it is difficult to treat multiple test samples all at a time. Thus, it is intended to optimize the various processes described above and to establish a system adaptable to automatic analysis.

Means for Solving Problem

The inventors of the present invention made a thorough investigation, and as a result, they found an apparatus that can automatically prepare a sample for mass spectrometry when a blood serum sample is applied. Thereafter, by performing mass spectrometry, an automatic analysis of sugar chain was made possible. The inventors have been able to develop an apparatus which is capable of carrying out all processes including from pretreatment to capturing of a sugar chain, modification of sialic acid, and to release of the sugar chain.

The present invention provides the following.

(1) A method for analyzing a sugar chain in a sample, the method comprising the following steps:

A) a sugar chain releasing step of releasing a sugar chain in a sample, the step comprising the following steps:

A-1) a step of providing the sample on a plate for reaction;
A-2) a step of adding a solubilizing agent to the sample to thereby place the sample under a reaction condition;
A-3) a step of adding a reducing agent to the sample to thereby place the sample under a reaction condition;
A-4) a step of adding an —SH protecting agent to the sample to thereby place the sample under a reaction condition;
A-5) a step of adding a proteolytic enzyme to the sample to thereby place the sample under a reaction condition;
A-6) a step of deactivating the proteolytic enzyme; and
A-7) a step of adding a sugar chain releasing enzyme to the sample to thereby release the sugar chain;

B) a detection sample preparing step of preparing the released sugar chain for use in detection, the step comprising the following steps:

B-1) a step of contacting the sample prepared in the step (A) with a sugar chain-capturing bead to thereby place the sample under the conditions allowing the released sugar chain in the sample to bind to the bead, and thus producing a captured sugar chain sample;

B-2) a step of adding a protein denaturing agent to the captured sugar chain sample to thereby place the captured sugar chain sample under a reaction condition;

B-3) a step of washing the captured sugar chain sample, and then discarding the residual washing liquid by suction;

B-4) a step of adding a salt releasing agent for the sugar chain capturing agent on beads to the captured sugar chain sample, and then discarding the salt releasing agent by suction;

B-5) a step of adding a protective agent to the captured sugar chain sample to thereby place the captured sugar chain under a reaction condition;

B-6) a step of adding an acid to the captured sugar chain sample, and discarding the acid by suction;

B-7) a step of adding an organic reaction solvent to the captured sugar chain sample;

B-8) a step of removing moisture and solvents in the bead;

B-9) a step of adding an alkyl esterifying agent to the captured sugar chain sample to thereby place the captured sugar chain sample under a reaction condition, and alkylating the carboxylic acid of sialic acid;

B-10) a step of adding the organic reaction solvent to the captured sugar chain sample, and discarding the organic reaction solvent by suction;

B-11) a step of washing the captured sugar chain sample, and subsequently discarding the residual washing liquid by suction;

B-12) a step of releasing a sugar chain sample from the captured sugar chain sample, wherein when an analysis requiring tagging is conducted, the sugar chain in the captured sugar chain sample is tagged with a labeling reagent and is released from the bead; and B-13) a step of dissolving the released sugar chain sample to produce a sugar chain sample solution;

C) when performing mass spectrometry using a plate, a step of producing a plate for mass spectrometry having the captured sugar chain dotted thereon, the step comprising:

C-1) a step of disposing the tagged sugar chain sample solution obtained in the step (B) on a plate for recovery; and the step also optionally comprising the steps (C-2) to (C-6):

C-2) a step of disposing the tagged sugar chain sample solution from the plate for recovery and the organic solvent, on a plate for mixing so as to obtain a concentration at which the sugar chain adsorbs to a solid phase;

C-3) a step of providing a solid phase carrier-enclosed plate;

C-4) a step of activating the solid phase carrier-enclosed plate according to the phase of the solid phase carrier-enclosed plate, and washing the solid phase carrier-enclosed plate;

C-5) a step of adding the tagged sugar chain sample solution to the solid phase carrier-enclosed plate, and conditioning the tagged sugar chain sample solution to a solvent having a polarity appropriate for the phase of the solid phase carrier-enclosed plate;

C-6) a step of recovering the tagged sugar chain sample solution by suction from the solid phase carrier-enclosed plate to a second plate for recovery; and when subjecting the tagged sugar chain sample solution to MALDI-TOF MS, comprising the following step (C-7):

C-7) a step of mixing the tagged sugar chain sample solution with a matrix for mass spectrometry, and dotting the mixture on a plate for determination; and D) a step of conducting an analysis of the sugar chain to be determined.

(2) The method according to item (1), the preceding steps are further characterized by at least any one of the following:

A) in the sugar chain releasing step of releasing a sugar chain in a sample to prepare a sugar chain sample for analysis:

A-1) the sample is a body fluid, a cell extract or a tissue extract;

A-2) the solubilizing agent is 1-propanesulfonic acid, 2-hydroxy-3-lauramide (PHL), 1-propanesulfonic acid, 2-hydroxy-3-myristamide (PHM), 2-hydroxy-3-sulfopropyl laurate (HSD) or an equivalent thereto, or the reaction condition is at 25° C. to 42° C.;

A-3) the reducing agent is dithiothreitol (DTT), TCEP (Tris(2-carboxyethyl)phosphine hydrochloride solution, 0.5 M), or an equivalent thereto, or the reaction condition is at room temperature to 80° C.;

A-4) the —SH protecting agent is iodoacetamide (IAA) or an equivalent thereto, or the reaction condition is at 20 to 37° C. in the dark;

A-5) the proteolytic enzyme is trypsin, chymotrypsin or an equivalent thereto, or the reaction condition is at 25 to 42° C.;

A-6) the condition for deactivating comprises heating to 65° C. or higher;

A-7) the sugar chain releasing enzyme is peptide-N-glycosidase F, peptide-N4-(acetyl-β-glucosaminyl)-asparagine amidase (PNGaseF), Endo H or an equivalent thereto, or the reaction conditions for the sugar chain releasing enzyme are at 25° C. to 42° C.;

with regard to the step (B),

B-1) the bead is a bead or magnetic bead having a sugar chain capturing group which includes an aminooxy group, an N-alkylaminooxy group, a hydrazide group, an azide group, a thiosemicarbazide group, a cysteine residue or a derivative thereof bound thereto, or the condition in which the released sugar chain in the sample binds to the bead is at 25 to 80° C.;

B-2) the denaturing agent is guanidine hydrochloride, urea, sodium dodecyl sulfate or an equivalent thereto, or the reaction condition involves adding at room temperature, and maintaining the temperature to allow the bead to sufficiently swell (from 10 seconds to 5 minutes);

B-3) the washing is performed using water;

B-4) the sugar chain capturing agent on the bead is an aminooxy group, an N-alkylaminooxy group, a hydrazide group, an azide group, a thiosemicarbazide group, a cysteine residue or a derivative thereof, and the salt releasing agent is triethylamine or an equivalent thereto in the case of hydrazide, and is triethylamine or an equivalent thereto in the case of an N-alkylaminooxy group;

B-5) the protective agent is acetic anhydride, succinic anhydride or another acid anhydride, or an equivalent thereto, or the reaction condition uses acetic anhydride/methanol at 15 to 37° C.;

B-6) the acid is hydrochloric acid or another inorganic acid, or an equivalent acid at pH2 to 3;

B-7) the step comprises a step for replacing with a hydrophilic organic solvent before replacing with the organic reaction solvent, and the hydrophilic organic solvent is a lower alcohol such as methanol or ethanol, acetonitrile, or acetone, while the organic reaction solvent is dioxane, acetonitrile, tetrahydrofuran or an equivalent thereto;

B-8) the step of removing the solvent and the moisture in the bead comprises wiping of the bottom with a filter paper, a blotting paper, a gauze, a towel, a hand towel, a tissue paper or a cotton sheet;

B-9) the alkyl esterifying agent is methyl-p-tolyl-triazene (MTT), ethyl-p-tolyl-triazene (ETT), butyl-p-tolyl-triazene (BTT) or an equivalent thereto, or the reaction condition uses 100 mM MTT/dioxane at 20 to 80° C. for 30 minutes to 5 hours;

B-10) the organic reaction solvent is dioxane, acetonitrile, tetrahydrofuran or an equivalent thereto;

B-11) the washing is performed using at least one selected from the group consisting of methanol, a NaCl solution and water;

B-12) the tagging is carried out, such that the tagging is performed using a chromophore capable of absorbing ultraviolet and visible rays, a tag having a structure emitting fluorescence, an affinity tag having a molecule capable of interacting with another molecule, a tag having a functional group capable of specifically reacting with a functional group, a tag having a functional group in a hydrophobic structure, or a tag having a metal ion ligand, and the tagging is conducted by adding acetic acid, acetonitrile, an acetate buffer or an equivalent thereto; and B-13) the dissolving of the tagged captured sugar chain sample is performed using water, an aqueous solution or an equivalent thereto;

C) in the step of producing a plate for mass spectrometry having the captured sugar chain sample dotted thereon;

C-1) the disposing on the plate for recovery is conducted under the conditions of removing the reagent for tagging;

C-2) the concentration at which the sugar chain adsorbs to the solid phase is 80 to 90% in an organic solvent;

C-3) the solid phase carrier-enclosed plate is of multi-well type and includes a surface of a resin or membrane suitable for solid phase extraction;

C-4) when the solid phase carrier-enclosed plate is in normal phase mode, washing is conducted sequentially with water and acetonitrile, and when the solid phase carrier-enclosed plate is in reverse phase mode, washing is conducted sequentially with a lower alcohol such as methanol and water;

C-5) the solvent having an opposite polarity is a hydrophobic organic solvent in the case of the normal phase mode, and is a hydrophilic solvent in the case of the reverse phase mode;

C-6) the second plate for recovery is of multi-well type and includes a surface of a resin or membrane suitable for solid phase extraction; and C-7) the matrix for mass spectrometry is 2,5-dihydroxybenzoic acid or an equivalent thereto, and the dotting of the tagged sugar chain sample solution on the matrix for mass spectrometry is conducted in mixture or in sequence, and is optionally diluted;

D) the analysis of the sugar chain to be determined is conducted by high performance liquid chromatography (HPLC), liquid chromatography-electrospray ionization mass spectrometry (LC-ESI MS), matrix assisted laser desorption ionization—Time-of-Flight (MALDI-TOF), or an equivalent thereto, while when using a coloring reagent or biotin in the tagging, a step of removing any excess coloring reagent is carried out as necessary, and when the beads are magnetic beads, the magnetic beads are beads having a modifiable functional group, a hydrazide group or an aminooxy group.

(3) The method according to item (1), further characterized by at least one step among comprising the following:

A) a sugar chain releasing step of releasing a sugar chain in a sample, the step comprising the following steps:

A-1) a step of providing blood serum as a sample on a filter plate;

A-2) a step of adding 1-propanesulfonic acid, 2-hydroxy-3-lauramide (PHL) or 1-propanesulfonic acid, 2-hydroxy-3-myristamide (PHM)/ammonium bicarbonate, and allowing the mixture to react for 5 to 60 minutes (for example, 10 min.) at 25 to 42° C. (for example, 37° C.);

A-3) a step of adding dithiothreitol (DTT) to the sample, allowing the mixture to react for 10 to 60 (for example, 30 min.) minutes at 50 to 80° C. (for example, 60° C.), and then cooling the reaction mixture to room temperature;

A-4) a step of adding iodoacetamide (IAA), and allowing the mixture to react for 0.5 to 2 hours (for example, 1 h) at room temperature in the dark;

A-5) a step of adding trypsin to the sample, and allowing the mixture to react for 30 to 120 minutes (for example, 60 min.) at 25 to 42° C. (for example, 37° C.);

A-6) a step of heating the sample to 80 to 100° C. (for example, 90° C.) for 1 to 10 minutes (for example, 5 min.), and then cooling the sample to room temperature; and A-7) a step of adding PNGaseF, and allowing the mixture to react for 6 to 24 hours (for example, 12 h) at 25 to 42° C. (for example, 37° C.);

B) a detection sample preparing step of preparing the released sugar chain for use in detection, the step comprising the following steps:

B-1) a step of contacting the captured sugar chain sample prepared in the step (A) with beads for capturing sugar chains, to thereby allow binding at 40 or higher (for example, 80° C.), and thus producing a captured sugar chain sample;

B-2) a step of adding guanidine hydrochloride to the captured sugar chain sample to thereby place the captured sugar chain sample under a reaction condition, and then discarding the reaction liquid by suction;

B-3) a step of washing the captured sugar chain sample with water, and then discarding the water by suction;

B-4) a step of washing the captured sugar chain sample with triethylamine, and then discarding the triethylamine by suction;

B-5) a step of adding acetic anhydride to the captured sugar chain sample to thereby place the captured sugar chain sample under the reaction conditions of using 10% acetic anhydride/methanol at room temperature for 10 minutes to 2 hours (for example, 30 min.), and then discarding the acetic anhydride by suction;

B-6) a step of adding hydrochloric acid to the captured sugar chain sample, and discarding the hydrochloric acid by suction;

B-7) a step of adding methanol to the captured sugar chain sample, discarding the methanol by suction, and then adding dioxane to the captured sugar chain sample;

B-8) a step of wiping the bottom with a cotton sheet;

B-9) a step of adding methyl-p-tolyl-triazene (MTT) to the captured sugar chain sample, and allowing the mixture to react for 30 to 120 minutes (for example, 60 min.) at 60° C. or higher (for example, 80° C.);

B-10) a step of adding dioxane to the captured sugar chain sample, and discarding the dioxane by suction;

B-11) a step of washing the captured sugar chain sample sequentially with methanol, a NaCl solution and water, and then discarding the water by suction;

B-12) a step of adding acetic acid and acetonitrile to the captured sugar chain sample, and tagging the sugar chain in the captured sugar chain sample using aminooxytryptophanyl arginine methyl ester/water, O-benzylhydroxylamine hydrochloride/water, or anthraniloyl hydrazine/water; and B-13) a step of adding water to the tagged captured sugar chain sample to produce a tagged sugar chain sample solution;

C) a step of producing a plate for mass spectrometry having the tagged captured sugar chain sample dotted thereon, the step comprising:

C-1) a step of disposing the tagged sugar chain sample solution obtained in the step (B) on a plate for recovery;

C-2) a step of disposing the tagged sugar chain sample solution from the plate for recovery and acetonitrile on a plate for mixing, so as to achieve a final concentration of acetonitrile of 80 to 90%;

C-3) a step of providing a solid phase carrier-enclosed plate which is in normal phase mode;

C-4) a step of washing the solid phase carrier-enclosed plate sequentially with water and acetonitrile, and discarding water and acetonitrile by suction;

C-5) a step of adding the tagged sugar chain sample solution to the solid phase carrier-enclosed plate, discarding the liquid, washing the plate with acetonitrile, and adding 1 to 20% (for example, 5%) acetonitrile thereto;

C-6) a step of recovering the bead by suction from the solid phase carrier-enclosed plate to the second plate for recovery; and C-7) a step of adding 2,5-dihydroxybenzoic acid in 20 to 40% (for example, 30%) acetonitrile, to the tagged sugar chain sample solution, and mixing and dotting the mixture; and D) a step of performing mass spectrometry by MALDI-TOF MS.

(4) The method according to item (3), wherein the sugar chain-capturing bead are magnetic beads, and separation is conducted by means of a magnetic field instead of the discarding by suction.

(5) A method for preparing a pretreatment sample for analyzing a sugar chain in a sample, the method comprising the following steps:

A) a sugar chain releasing step of releasing a sugar chain in a sample, the step comprising the following steps:

A-1) a step of providing the sample on a plate for reaction;

A-2) a step of adding a solubilizing agent to the sample to thereby place the sample under a reaction condition;

A-3) a step of adding a reducing agent to the sample to thereby place the sample under a reaction condition;

A-4) a step of adding an —SH protecting agent to the sample to thereby place the sample under a reaction condition;

A-5) a step of adding a proteolytic enzyme to the sample to thereby place the sample under a reaction condition;

A-6) a step of deactivating the proteolytic enzyme; and

A-7) a step of adding a sugar chain releasing enzyme to the sample to release the sugar chain; and B) a detection sample preparing step of preparing the release sugar chain for use in detection, the step comprising the following steps:

B-1) a step of contacting the sample prepared in the step (A) with beads to thereby place the sample under the conditions allowing the released sugar chain in the sample to bind to the bead, and thus producing a captured sugar chain sample;

B-2) a step of adding a protein denaturing agent to the captured sugar chain sample to thereby place the captured sugar chain sample under a reaction condition;

B-3) a step of washing the captured sugar chain sample, and then discarding the residual washing liquid by suction;

B-4) a step of adding a salt releasing agent for the sugar chain capturing agent on beads to the captured sugar chain sample, and then discarding the salt releasing agent by suction;

B-5) a step of adding a protective agent to the captured sugar chain sample to thereby place the captured sugar chain sample under a reaction condition;

B-6) a step of adding an acid to the captured sugar chain sample, and discarding the acid by suction;

B-7) a step of adding an organic reaction solvent to the captured sugar chain sample;

B-8) a step of removing the solvent and the moisture in the bead;

B-9) a step of adding an alkyl esterifying agent to the captured sugar chain sample to thereby place the captured sugar chain sample under a reaction condition, and alkylating the carboxylic acid of sialic acid;

B-10) a step of adding the organic reaction solvent to the captured sugar chain sample, and discarding the organic reaction solvent by suction;

B-11) a step of washing the captured sugar chain sample, and then discarding the residual washing liquid by suction;

B-12) a step of releasing a sugar chain sample from the captured sugar chain sample, wherein when an analysis requiring tagging is performed, the sugar chain in the captured sugar chain sample is tagged with a labeling reagent and is released from the bead; and B-13) a step of dissolving the released sugar chain sample to produce a sugar chain sample solution.

(6) The method according to item (5), further characterized by any of the features of item (2), (3) or (4).

(7) A sugar chain analyzing apparatus, comprising the following units:

1) a plate mounting stand, which is optionally heatable and/or movable;

2) a reagent storing unit that stores one or a plurality of prepared reagents at a temperature required for storage, wherein the reagent storing unit is a storage connected to a rack or a valve, and the reagent storing unit stores one or several reagents selected from the group consisting of a solubilizing agent, a reducing agent, an —SH protecting agent, a proteolytic enzyme, a sugar chain releasing enzyme, a sugar chain-capturing bead, a protein denaturing agent, a washing liquid, a salt releasing agent for a sugar chain capturing agent, a protective agent, an acid, an organic reaction solvent, an alkyl esterifying agent, a tagging agent, a solvent for the tagged sugar chain sample, an organic solvent for adsorbing to a solid phase, a solvent for acclimation, and a matrix for mass spectrometry;

3) a nozzle and/or a valve for dispensing each reagent from the reagent storing unit;

4) a plate moving unit;

5) optionally, a suction discarding unit or a magnetic field generating unit;
6) optionally, a shaking/stirring unit;
7) a plate storing unit; and
8) a unit that performs mass spectrometry.

(8) The apparatus according to item (7), characterized in that the features of any one of items (2) to (4) are manifested.

(9) An automatic sugar chain pretreatment apparatus, comprising the following units:
1) a plate mounting stand, which is heatable and/or movable as necessary;
2) a reagent storing unit that stores one or a plurality of prepared reagents at a temperature required for storage, wherein the reagent storing unit is a storage connected to a rack or a valve, and the reagent storing unit stores one or several reagents selected from the group consisting of a solubilizing agent, a reducing agent, an —SH protecting agent, a proteolytic enzyme, a sugar chain releasing enzyme, a sugar chain-capturing bead, a protein denaturing agent, a washing liquid, a salt releasing agent for a sugar chain capturing agent, a protective agent, an acid, an organic reaction solvent, an alkyl esterifying agent, a tagging agent, a solvent for the tagged sugar chain sample, an organic solvent for adsorbing to a solid phase, a solvent for acclimation, and a matrix for mass spectrometry;
3) a nozzle and/or a valve for dispensing each reagent from the reagent storing unit;
4) a plate moving unit;
5) optionally, a suction discarding unit or a magnetic field generating unit;
6) optionally, a shaking/stirring unit; and
7) a plate storing unit.

(10) The apparatus according to item (9), characterized in that the features of any one of items (2) to (4) are manifested.

Alternatively, the present invention provides the following in connection with the apparatus of item (9).

(11) An automatic sugar chain pretreatment apparatus, comprising:
a casing base provided with a cover capable of freely opening and closing; and a dispensing head moving mechanism that is installed inside the casing base and moves a dispensing head in longitudinal and transverse directions as described below;
a dispensing head that raises and lowers a plurality of dispensing needles arranged in a row, altogether by means of an elevating mechanism;
a first constant-temperature bath installed above the installation space for the casing base, which is equipped with a unit that conducts heating and cooling of a receiving stand that holds a microplate, and is provided with a lid having an inner lid to cover the upper part of the receiving stand;
a reagent rack and a plurality of microplates for mixing, which are installed above the installation space for the casing base;
a first low-pressure recovering device, being in a frame form, which depressurizes while having a filter plate mounted on the upper opening, and receives the liquid that has passed through the filter of the filter plate, into a microplate installed inside the recovering device; a first suction discarding device, being in a frame form, which depressurizes and suctions while having a filter plate mounted on the upper opening, and discards the liquid that has passed through the filter; and a second constant-temperature bath, which is equipped with a unit that conducts heating and cooling of a receiving stand that holds a filter plate, and is provided with an automatically opening and closing lid to cover the upper part of the receiving stand, all of these devices being disposed and arranged in a row along the longitudinal direction and above the installation space for the casing base;
a filter plate moving mechanism that retains a filter plate and moves the filter plate to each of the first low-pressure recovering device, the first suction discarding device and the second constant-temperature bath in sequence, as well as a second low-pressure recovering device, being in a frame form, which depressurizes while having an SPE plate mounted on the upper opening, and receives the liquid that has passed through the solid phase body of the SPE plate, into a microplate installed inside the recovering device; a second suction discarding device, being in a frame form, which depressurizes and suctions while having an SPE plate mounted on the upper opening, and discards the liquid that has passed through the solid phase body; and a target plate receiving stand, which holds a target plate that is dotted on the surface with the sample that has been finished with the final treatment step, all of these devices being disposed and arranged in a row along the longitudinal direction and above the installation space for the casing base;
an SPE plate moving mechanism that retains an SPE plate and moves the SPE plate between the second low-pressure recovering device and the second suction discarding device;
a control device that is installed in the casing base, and has been inputted with the operation protocol;
a microplate having a plurality of wells arranged in a matrix array, which is covered with a sheet while biological samples have been injected into each well; a filter plate having a plurality of filters arranged in a matrix array; and an SPE plate for sample in a trace amount, having a plurality of solid phase bodies arranged in a matrix array,
wherein the apparatus is made to operate each of the devices according to the operation protocol inputted to the control device.

(12) An automatic sugar chain pretreatment apparatus, comprising:
a casing base provided with a cover capable of freely opening and closing; and a dispensing head moving mechanism that is installed inside the casing base and moves a below-described dispensing head in longitudinal and transverse directions;
a dispensing head that raises and lowers a plurality of dispensing needles arranged in a row, altogether by means of an elevating mechanism;
a first constant-temperature bath installed above the installation space for the casing base, which is equipped with a unit that conducts heating and cooling of a receiving stand that holds a microplate, and is provided with a lid having an inner lid to cover the upper part of the receiving stand;
a reagent rack and a plurality of microplates for mixing, which are installed above the installation space for the casing base;
a first low-pressure recovering device, being in a frame form, which depressurizes while having a filter plate mounted on the upper opening, and receives the liquid that has passed through the filter of the filter plate, into a microplate installed inside the recovering device; a first suction discarding device, being in a frame form, which depressurizes and suctions while having a filter plate mounted on the upper opening, and discards the liquid that has passed through the filter; a bottom wiper, which is provide with a planar wiping material on the upper surface, and is intended to wipe out the liquid adhering to the lower surface of the bottom of the filter plate; and a second constant-temperature bath, which is equipped with a unit that conducts heating and cooling of a receiving stand that holds a filter plate, and is provided with an automatically opening and closing lid to cover the upper part of the receiving stand, all of these devices being disposed and arranged in a row along the longitudinal direction and above the installation space for the casing base;

a filter plate moving mechanism that retains a filter plate and moves the filter plate to each of the first low-pressure recovering device, the first suction discarding device, the bottom wiper and the second constant-temperature bath in sequence, as well as a second low-pressure recovering device, being in a frame form, which depressurizes while having an SPE plate mounted on the upper opening, and receives the liquid that has passed through the solid phase body of the SPE plate, into a microplate installed inside the recovering device;

a second suction discarding device, being in a frame form, which depressurizes and suctions while having an SPE plate mounted on the upper opening, and discards the liquid that has passed through the solid phase body; and a target plate receiving stand, which holds a target plate that is dotted on the surface with the sample that has been finished with the final treatment step, all of these devices being disposed and arranged in a row along the longitudinal direction and above the installation space for the casing base;

an SPE plate moving mechanism that retains an SPE plate and moves the SPE plate between the second low-pressure recovering device and the second suction discarding device;

a control device that is installed in the casing base, and has been inputted with the operation protocol;

a microplate having a plurality of wells arranged in a matrix array, which is covered with a sheet while biological samples have been injected into each well; a filter plate having a plurality of filters arranged in a matrix array; and an SPE plate for sample in a trace amount, having a plurality of solid phase bodies arranged in a matrix array, wherein the apparatus is made to operate each of the devices according to the operation protocol inputted to the control device.

(13) The automatic sugar chain pretreatment apparatus according to item (1) or (2), wherein the dispensing head is a dispensing head constituted to include a supporting frame; an elevator stand that slides in the vertical direction along a guide rod installed on the supporting frame in parallel with the dispensing needles; a driving motor fixed on the supporting frame; an elevator stand moving mechanism that has a ball screw connected to the rotating axis of the driving motor and moves the elevator stand in the vertical direction; and dispensing needles retained in a dispensing needle holder installed on the elevator stand.

(14) The automatic sugar chain pretreatment apparatus according to item (13), wherein a cylinder is fixed vertically downward at the lower part of the supporting frame in the dispensing head, and at the same time, a pressurizing plate is adhered at the tip of the piston rod of the cylinder.

(15) The automatic sugar chain pretreatment apparatus according to item (11), (12), (13) or (14), wherein the first constant-temperature bath is a first constant-temperature bath having a main body part that is constructed by including a cartridge heater built in at the internal center of the receiving stand formed from an aluminum block, and also by disposing a Peltier element and a heat sink at the lower part of the receiving stand, wherein the upper part of the receiving stand in the main body part is covered by a lid which has a silicone sheet pasted on the inside and has an inner lid with a built-in cartridge heater at the internal center, the inner lid being elastically supported via a spring.

(16) The automatic sugar chain pretreatment apparatus according to item (11), (12), (13) (14) or (15), wherein the filter plate moving mechanism and the SPE plate moving mechanism are moving mechanisms each having a pulley installed at both ends in the length direction of a supporting plate that is installed to stand along the longitudinal direction of the casing base, with one of the pulleys being made to be rotary driven by a step motor, wherein a horizontally moving plate is connected to a belt hung between the two pulleys and revolved, a vertical moving unit is installed on the horizontally moving plate, and the vertical moving unit is ascended and descended by a vertically moving rod that supports a receiving frame intended to receive an inner frame at the upper end, and slides in the vertical direction along a guide installed vertically inside the supporting frame, and by a ball screw connected to the rotating axis of a motor fixed inside the supporting frame, and wherein the mechanisms are each constituted to have an elevating rod connected to the vertically moving rod.

(17) The automatic sugar chain pretreatment apparatus according to item (11), (12), (13), (14), (15) or (16), wherein the second constant-temperature bath is a second constant-temperature bath having a main body part that is constructed by including a cartridge heater built in at the internal center of the receiving stand formed from an aluminum block, and also an air circulation path installed across from the internal center to the surface, and by disposing a Peltier element and a heat sink at the lower part of the receiving stand, wherein an air circulation path which is in communication with the above air circulation path is provided between the upper part of the receiving stand in the main body part and the filter plate located thereon, and a duct and a fan are further provided to let the air discharged out of the filter plate flow again into the receiving stand to thereby circulate, while the upper part of the receiving stand in the main body part is covered by a lid.

(A1)

A sugar chain releasing method for releasing a sugar chain in a sample, the method comprising the following steps:

A) a sugar chain releasing step of releasing a sugar chain in a sample, the step comprising the following steps:
  A-1) a step of providing the sample on a plate for reaction;
  A-2) a step of adding a solubilizing agent to the sample to thereby place the sample under a reaction condition;
  A-3) a step of adding a reducing agent to the sample to thereby place the sample under a reaction condition;
  A-4) a step of adding an —SH protecting agent to the sample to thereby place the sample under a reaction condition;
  A-5) a step of adding a proteolytic enzyme to the sample to thereby place the sample under a reaction condition;
  A-6) a step of deactivating the proteolytic enzyme; and
  A-7) a step of adding a sugar chain releasing enzyme to the sample to thereby release the sugar chain.

(A2)

The method according to item (A1), wherein the preceding steps are further characterized by at least any one of the following:

A) in the sugar chain releasing step of releasing a sugar chain in a sample to prepare a sugar chain sample for analysis:
  A-1) the sample is a body fluid, a cell extract or a tissue extract;
  A-2) the solubilizing agent is 1-propanesulfonic acid, 2-hydroxy-3-lauramide (PHL), 1-propanesulfonic acid, 2-hydroxy-3-myristamide (PHM), 2-hydroxy-3-sulfopropyl laurate (HSD) or an equivalent thereto, and the reaction condition is at 25° C. to 42° C.;
  A-3) the reducing agent is dithiothreitol (DTT), TCEP (Tris(2-carboxyethyl)phosphine hydrochloride solution, 0.5 M), or an equivalent thereto, and the reaction condition is at room temperature to 80° C.;

A-4) the —SH protecting agent is iodoacetamide (IAA) or an equivalent thereto, and
the reaction condition is at 20 to 37° C. in the dark;
A-5) the proteolytic enzyme is trypsin, chymotrypsin or an equivalent thereto, and
the reaction condition is at 25 to 42° C.;
A-6) the conditions for deactivating include heating to 65° C. or higher;
A-7) the sugar chain releasing enzyme is peptide-N-glycosidase F, peptide-N4-(acetyl-β-glucosaminyl)-asparagine amidase (PNGaseF), Endo H or an equivalent thereto, and
the reaction conditions for the sugar chain releasing enzyme are at 25° C. to 42° C.

(A3)

The method according to item (A1) or (A2), further comprising at least one of the following steps:

A) a sugar chain releasing step of releasing a sugar chain in a sample, the step comprising the following steps:
A-1) a step of providing blood serum as a sample on a filter plate;
A-2) a step of adding 1-propanesulfonic acid, 2-hydroxy-3-lauramide (PHL) or 1-propanesulfonic acid, 2-hydroxy-3-myristamide (PHM)/ammonium bicarbonate, and allowing the mixture to react for 5 to 60 minutes at 25 to 42° C.;
A-3) a step of adding dithiothreitol (DTT) to the sample, allowing the mixture to react for 10 to 60 minutes at 50 to 80° C., and then cooling the reaction mixture to room temperature;
A-4) a step of adding iodoacetamide (IAA), and allowing the mixture to react for 0.5 to 2 hours at room temperature in the dark;
A-5) a step of adding trypsin to the sample, and allowing the mixture to react for 30 to 120 minutes at 25 to 42° C.;
A-6) a step of heating the sample to 80 to 100° C. for 1 to 10 minutes, and then cooling the sample to room temperature; and
A-7) a step of adding PNGaseF, and allowing the mixture to react for 6 to 24 hours at 25 to 42° C.

(A4)

The method according to any one of items (A1) to (A3), which is used to prepare a pretreatment sample for an analysis of a sugar chain in a sample.

(B1)

A detection sample preparing method for preparing a released sugar chain for use in detection, the method comprising the following steps:
B-1) a step of contacting the sample with a sugar chain-capturing bead to thereby place the sample under the conditions allowing the released sugar chain in the sample to bind to the bead, and thus producing a captured sugar chain sample;
B-2) a step of adding a protein denaturing agent to the captured sugar chain sample to thereby place the captured sugar chain sample under a reaction condition;
B-3) a step of washing the captured sugar chain sample, and then discarding the residual washing liquid by suction;
B-4) a step of adding a salt releasing agent for the sugar chain capturing agent on beads to the captured sugar chain sample, and then discarding the salt releasing agent by suction;
B-5) a step of adding a protective agent to the captured sugar chain sample to thereby place the captured sugar chain under a reaction condition;
B-6) a step of adding an acid to the captured sugar chain sample, and discarding the acid by suction;
B-7) a step of adding an organic reaction solvent to the captured sugar chain sample;
B-8) a step of removing the solvent and the moisture in the bead;
B-9) a step of adding an alkyl esterifying agent to the captured sugar chain sample to thereby place the captured sugar chain sample under a reaction condition, and alkylating the carboxylic acid of sialic acid;
B-10) a step of adding the organic reaction solvent to the captured sugar chain sample, and discarding the organic reaction solvent by suction;
B-11) a step of washing the captured sugar chain sample, and subsequently discarding the residual washing liquid by suction;
B-12) a step of releasing a sugar chain sample from the captured sugar chain sample, wherein when an analysis requiring tagging is conducted, the sugar chain in the captured sugar chain sample is tagged with a labeling reagent and is released from the bead; and
B-13) a step of dissolving the released sugar chain sample to produce a sugar chain sample solution.

(B2)

The method according to item (B1), wherein the preceding steps are further characterized by at least any one of the following:
B-1) the bead is a bead or magnetic bead having a sugar chain capturing group which includes an aminooxy group, an N-alkylaminooxy group, a hydrazide group, an azide group, a thiosemicarbazide group, a cysteine residue or a derivative thereof bound thereto, or
the conditions in which the released sugar chain in the sample binds to the bead are at 25 to 80° C.;
B-2) the denaturing agent is guanidine hydrochloride, urea, sodium dodecyl sulfate or an equivalent thereto, or
the reaction conditions involve adding at room temperature, and maintaining the temperature to allow the bead to sufficiently swell (from 10 seconds to 5 minutes);
B-3) the washing is performed using water;
B-4) the sugar chain capturing agent on the bead is an aminooxy group, an N-alkylaminooxy group, a hydrazide group, an azide group, a thiosemicarbazide group, a cysteine residue or a derivative thereof, and the salt releasing agent is triethylamine or an equivalent thereto in the case of hydrazide, and is triethylamine or an equivalent thereto in the case of an N-alkylaminooxy group;
B-5) the protective agent is acetic anhydride, succinic anhydride or another acid anhydride, or an equivalent thereto, or
the reaction conditions use acetic anhydride/methanol at 15 to 37° C.;
B-6) the acid is hydrochloric acid or another inorganic acid, or an equivalent acid at pH2 to 3;
B-7) the step includes a step of replacing with a hydrophilic organic solvent before replacing with the organic reaction solvent, and the hydrophilic organic solvent is a lower alcohol such as methanol or ethanol, acetonitrile, or acetone, while the organic reaction solvent is dioxane, acetonitrile, tetrahydrofuran or an equivalent thereto;
B-8) the step of removing the solvent and the moisture in the bead includes wiping of the bottom with a filter paper, a blotting paper, a gauze, a towel, a hand towel, a tissue paper or a cotton sheet;

B-9) the alkyl esterifying agent is methyl-p-tolyl-triazene (MTT), ethyl-p-tolyl-triazene (ETT), butyl-p-tolyl-triazene (BTT) or an equivalent thereto, or
the reaction conditions use 100 mM MTT/dioxane at 20 to 80° C. for 30 minutes to 5 hours;
B-10) the organic reaction solvent is dioxane, acetonitrile, tetrahydrofuran or an equivalent thereto;
B-11) the washing is performed using at least one selected from the group consisting of methanol, a NaCl solution and water;
B-12) the tagging is carried out, such that the tagging is performed using a chromophore capable of absorbing ultraviolet and visible rays, a tag having a structure emitting fluorescence, an affinity tag having a molecule capable of interacting with another molecule, a tag having a functional group capable of specifically reacting with a functional group, a tag having a functional group in a hydrophobic structure, or a tag having a metal ion ligand, and the tagging is conducted by adding acetic acid, acetonitrile, an acetate buffer or an equivalent thereto; and
B-13) the dissolving of the tagged captured sugar chain sample is performed using water, an aqueous solution or an equivalent thereto.

(B3)
The method according to item (B1) or (B2), further comprising at least one of the following steps:
B-1) a step of contacting the captured sugar chain sample prepared in the step (A) with beads for capturing sugar chain, to thereby allow binding at 40 to 80° C., and thus producing a captured sugar chain sample;
B-2) a step of adding guanidine hydrochloride to the captured sugar chain sample to thereby place the captured sugar chain sample under a reaction condition, and then discarding the reaction liquid by suction;
B-3) a step of washing the captured sugar chain sample with water, and then discarding the water by suction;
B-4) a step of washing the captured sugar chain sample with triethylamine, and then discarding the triethylamine by suction;
B-5) a step of adding acetic anhydride to the captured sugar chain sample to thereby place the captured sugar chain sample under the reaction conditions of using 10% acetic anhydride/methanol at room temperature for 10 minutes to 2 hours, and then discarding the acetic anhydride by suction;
B-6) a step of adding hydrochloric acid to the captured sugar chain sample, and discarding the hydrochloric acid by suction;
B-7) a step of adding methanol to the captured sugar chain sample, discarding the methanol by suction, and then adding dioxane to the captured sugar chain sample;
B-8) a step of wiping the bottom with a cotton sheet;
B-9) a step of adding methyl-p-tolyl-triazene (MTT) to the captured sugar chain sample, and allowing the mixture to react for 30 to 120 minutes (for example, 60 min.) at 60° C. or higher;
B-10) a step of adding dioxane to the captured sugar chain sample, and discarding the dioxane by suction;
B-11) a step of washing the captured sugar chain sample sequentially with methanol, a NaCl solution and water, and then discarding the water by suction;
B-12) a step of adding acetic acid and acetonitrile to the captured sugar chain sample, and tagging the sugar chain in the captured sugar chain sample using aminooxytryptophanyl arginine methyl ester/water, O-benzylhydroxylamine hydrochloride/water, or anthraniloyl hydrazine/water; and
B-13) a step of adding water to the tagged captured sugar chain sample to produce a tagged sugar chain sample solution.

(B4)
The method according to item (B3), wherein the sugar chain-capturing bead are magnetic beads, and separation is conducted by means of a magnetic field instead of the discarding by suction.

(B5)
The method according to any one of items (B1) to (B4), which is used for preparing a pretreatment sample for an analysis of a sugar chain in a sample.

(C1)
A method for producing a plate for mass spectrometry having a captured sugar chain sample dotted thereon for performing mass spectrometry using a plate, the method comprising the following steps:
C-1) a step of disposing a tagged sugar chain sample solution on a plate for recovery; and, optionally comprising the steps (C-2) to (C-6):
C-2) a step of disposing the tagged sugar chain sample solution from the plate for recovery and the organic solvent, on a plate for mixing so as to obtain a concentration at which the sugar chain adsorbs to a solid phase;
C-3) a step of providing a solid phase carrier-enclosed plate;
C-4) a step of activating the solid phase carrier-enclosed plate according to the phase of the solid phase carrier-enclosed plate, and washing the solid phase carrier-enclosed plate;
C-5) a step of adding the tagged sugar chain sample solution to the solid phase carrier-enclosed plate, and conditioning the tagged sugar chain sample solution to a solvent having a polarity appropriate for the phase of the solid phase carrier-enclosed plate;
C-6) a step of recovering the tagged sugar chain sample solution by suction from the solid phase carrier-enclosed plate to a second plate for recovery; and
when subjecting the tagged sugar chain sample solution to MALDI-TOF MS, comprising the following step (C-7):
C-7) a step of mixing the tagged sugar chain sample solution with a matrix for mass spectrometry, and dotting the mixture on a plate for determination.

(C2)
The method according to item (C1), wherein the preceding steps are associated with at least any one of the following conditions:
C-1) the disposing on the plate for recovery is conducted under the conditions of removing the reagent for tagging;
C-2) the concentration at which the sugar chain adsorbs to the solid phase is 80 to 90% in an organic solvent;
C-3) the solid phase carrier-enclosed plate is of multi-well type and includes a surface of a resin or membrane suitable for solid phase extraction;
C-4) when the solid phase carrier-enclosed plate is in normal phase mode, washing is conducted sequentially with water and acetonitrile, and when the solid phase carrier-enclosed plate is in reverse phase mode, washing is conducted sequentially with a lower alcohol such as methanol and water;

C-5) the solvent having an opposite polarity is a hydrophobic organic solvent in the case of the normal phase mode, and is a hydrophilic solvent in the case of the reverse phase mode;

C-6) the second plate for recovery is of multi-well type and includes a surface of a resin or membrane suitable for solid phase extraction; and C-7) the matrix for mass spectrometry is 2,5-dihydroxybenzoic acid or an equivalent thereto, and the dotting of the tagged sugar chain sample solution on the matrix for mass spectrometry is conducted in mixture or in sequence, and is diluted as necessary.

(C3)

The method according to item (C1) or (C2), further comprising at least one of the following steps:

C) a step of producing a plate for mass spectrometry having the tagged captured sugar chain sample dotted thereon, the step comprising:

C-1) a step of disposing the tagged sugar chain sample solution obtained in the step (B) on a plate for recovery;

C-2) a step of disposing the tagged sugar chain sample solution from the plate for recovery and acetonitrile on a plate for mixing, so as to achieve a final concentration of acetonitrile of 80 to 90%;

C-3) a step of providing a solid phase carrier-enclosed plate which is in normal phase mode;

C-4) a step of washing the solid phase carrier-enclosed plate sequentially with water and acetonitrile, and discarding water and acetonitrile by suction;

C-5) a step of adding the tagged sugar chain sample solution to the solid phase carrier-enclosed plate, discarding the liquid, washing the plate with acetonitrile, and adding 1 to 20% acetonitrile thereto;

C-6) a step of recovering the bead by suction from the solid phase carrier-enclosed plate to the second plate for recovery; and C-7) a step of adding 2,5-dihydroxybenzoic acid in 20 to 40% acetonitrile, to the tagged sugar chain sample solution, and mixing and dotting the mixture.

(C4)

The method according to item (C3), wherein the sugar chain-capturing bead are magnetic beads, and separation is conducted by means of a magnetic field instead of the discarding by suction.

(C5)

The method according to any one of items (C1) to (C4), which uses the method for preparing a pretreatment sample for an analysis of a sugar chain in a sample.

(18) A kit for producing a plate for a reaction comprising a sugar chain derived from a sample and a sugar chain-capturing bead, the kit comprising:

A-1) the sample;
A-2) 1-propanesulfonic acid, 2-hydroxy-3-lauramide (PHL) or 1-propanesulfonic acid, 2-hydroxy-3-myristamide (PHM)/ammonium bicarbonate;
A-3) dithiothreitol (DTT);
A-4) iodoacetamide (IAA);
A-5) trypsin;
A-6) a heating unit;
A-7) PNGaseF;
B-1) a sugar chain-capturing bead;
B-2) guanidine hydrochloride:
B-3) water;
B-4) triethylamine;
B-5) 10% acetic anhydride/methanol;
B-6) hydrochloric acid;
B-7) methanol;
B-8) cotton sheet;
B-9) methyl-p-tolyl-triazene (MTT);
B-10) dioxane;
B-11) methanol, a NaCl solution and water;
B-12) acetic acid and acetonitrile, and aminooxytryptophanyl-arginine methyl ester/water, O-benzylhydroxylamine hydrochloride/water or anthraniloyl hydrazine/water;
B-13) water;
C-1) a plate for recovery;
C-2) acetonitrile and a plate for mixing;
C-3) a solid phase carrier-enclosed plate;
C-4) water and acetonitrile;
C-5) acetonitrile and 1 to 20% acetonitrile;
C-6) a second plate for recovery; and
C-7) 2,5-dihydroxybenzoic acid in 20 to 400 acetonitrile.

(18A) A kit for producing a plate for a reaction comprising a sugar chain derived from a sample and a sugar chain-capturing bead, the kit comprising the means for realizing any operations of items (1) to (5).

(19) A plate for analysis comprising a sugar chain derived from a sample and a sugar chain-capturing bead, wherein the sugar chain-capturing bead bound by the sugar chain released from the sample are dotted on at least one well of the plate, and the sugar chain is tagged with aminooxytryptophanyl-arginine methyl ester/water, O-benzylhydroxylamine hydrochloride/water or anthraniloyl hydrazine/water.

(20) A plate for analyzing a sugar chain in a sample, wherein the plate has at least one compartment for analysis, and a sugar chain-capturing bead having been dispensed in advance to said at least one compartment.

Therefore, these and other advantages of the present invention will be made clear to the readers when they read the following detailed description with reference to the appended drawings.

Effect of the Invention

It was made successful by the present invention to provide an auto-analyzing apparatus for analyzing a sugar chain contained in a sample such as a blood serum sample. Thereby, it was made possible to automatically analyze a large amount of sample simultaneously. The cumbersome pretreatments such as a use of a solublizing agent, reductive alkylation and digestion by trypsin, which were required to release a sugar chain quantitatively from a glycoprotein, were automated. Furthermore, a sugar chain that has been quantitatively released can be subjected to a rapid analysis of the sugar chain by performing chemoselective capturing and thereby easily removing troublesome foreign matters, and it was made possible to treat multiple test samples all at a time. The various processes described above were optimized, and a system adaptable to automatic analysis was established.

Since the present invention can automate the treatment processes of sugar chain purification, the processes can be carried out much more efficiently as compared to the conventional processes carried out manually, and purification can be conducted at high speed with high accuracy.

Since the apparatus of the present invention makes it possible to perform an analysis of multiple samples, a search for sugar chain biomarkers is anticipated, and it is conceived that the apparatus of the present invention may be used in diagnosis and the like, and in early diagnosis of a disease or the like.

BEST MODE(S) FOR CARRYING OUT THE INVENTION

Hereinafter, the present invention will be described. It will be understood as a matter of course that throughout the present specification, unless otherwise particularly stated, a singular expression encompasses the concept of plurality as well. Therefore, it will be understood as a matter of course that, unless otherwise particularly stated, a singular article or adjective (for example, "a", "an", "the" or the like in English) encompasses the concept of plurality as well. Furthermore, it will be understood as a matter of course that, unless otherwise particularly stated, the terms used in the present specification are used in the meaning as conventionally used in the related art. Therefore, unless defined otherwise, all of the jargons and technical terms used in the present specification have the same meanings as generally understood by those skilled in the art to which the present invention is pertained. In the case of contradiction, the present specification (including the definitions) dominates.

DEFINITIONS OF TERMS AND EXPLANATION OF FUNDAMENTAL TECHNOLOGY (Sugar Chain)

The term "sugar chain" as used herein means a compound formed by one or more unit sugars (monosacchrides and/or derivatives thereof) linked together. When two or more unit sugars are linked, the respective unit sugars are linked by dehydration condensation based on glycoside bond. Examples of such a sugar chain include polysaccharides present in the living body (glucose, galactose, mannose, fucose, xylose, N-acetylglucosamine, N-acetylgalactosamine, sialic acid, and complexes and derivatives thereof), as well as a wide variety of sugar chains that have been degraded or derived from complex biomolecules such as degraded polysaccharides, glycoproteins, proteoglycans, glycosaminoglycans and glycolipids, but examples are not limited to those. As used herein, the term sugar chain can be used interchangeably with "polysaccharide," "sugar," or "carbohydrate." Unless otherwise particularly stated, the "sugar chain" as used herein may include both a sugar chain and a sugar chain-containing substance.

The term "sugar chain-containing substance" as used herein means a substance containing a sugar chain and a substance other than a sugar chain. Such a sugar chain-containing substance are abundant in the living body, and examples thereof include polysaccharides present in the living body, as well as a variety of substances such as sugar chains degraded or derived from complex biomolecules such as degraded polysaccharides, glycoproteins, proteoglycans, glycosaminoglycan and glycolipids, but are not limited to those.

The term "monosaccharide" as used herein means polyhydroxyaldehyde or polyhydroxyketone and derivatives thereof, which are not hydrolyzed into molecules simpler than these, and include at least one hydroxyl group and at least one aldehyde group or ketone group. Monosaccharides are conventionally represented by the formula: $C_nH_{2n}O_n$, without being limited thereto, and also include fucose (deoxyhexose), N-acetylglucosamine and the like. Here, compounds of the above formula, in which n=2, 3, 4, 5, 6, 7, 8, 9 and 10, are respectively called diose, triose, tetraose, pentose, hexose, heptose, octose, nonose and decose. In general, these compounds correspond to aldehydes or ketones of chain-type polyhydric alcohols, and the former are called as aldoses, while the latter being called as ketoses.

When particularly mentioned herein, the term "derivative of monosaccharide" means a substance generated as a result of substitution of one or more hydroxyl groups on an unsubstituted monosaccharide, with another substituent. Derivatives of such a monosaccharide include, but are not limited to, a sugar having a carboxyl group (for example, aldonic acid in which the C-1 position has been oxidized to carboxylic acid (for example, D-gluconic acid obtained from oxidized D-glucose), uronic acid in which the terminal C atom has been converted to carboxylic acid (D-glucuronic acid obtained from oxidized D-glucose); a sugar having an amino group or a derivative of amino group (for example, acetylated amino group) (for example, N-acetyl-D-glucosamine, N-acetyl-D-galactosamine, or the like); a sugar having both an amino group and a carboxyl group (for example, N-acetylneuraminic acid (sialic acid), N-acetylmuraminic acid, and the like); a deoxidized sugar (for example, 2-deoxy-D-ribose); a sulfated sugar containing a sulfuric acid group; a phosphated sugar containing a phosphoric acid group; and the like. As used herein, when a compound is called as monosaccharide, the derivatives mentioned above are also included. Alternatively, in regard to sugars forming a hemiacetal structure, glycosides forming an acetal structure by reacting with alcohol, also fall in the scope of monosaccharide.

The term "interaction" as used herein means that, upon mentioning about two objects, the two objects exert force onto each other. Examples of such interaction include, but are not limited to, covalent bonding, hydrogen bonding, van der Waals force, ionic interaction, nonionic interaction, hydrophobic interaction, electrostatic interaction, and the like. Preferably, the interaction is hydrogen bonding, hydrophobic interaction, or the like. The term "covalent bonding" as used herein is used in the meaning as conventionally used in the related art, and means a chemical bonding formed by a pair of electrons that are shared by two atoms. The term "hydrogen bonding" as used herein is used in the meaning as conventionally used in the related art, and means a bonding generated when the only extranuclear electron of a hydrogen atom is attracted to an atom having high electronegativity, so that the nucleus of the hydrogen atom is exposed, and this nucleus attracts in turn another atom having high electronegativity. For example, the hydrogen bonding is generated between a hydrogen atom and an atom having high electronegativity (such as fluorine, oxygen or nitrogen).

The term "capturing of a sugar chain or a sugar chain-containing substance" as used herein means that a sugar chain or a sugar chain-containing substance is captured using the sugar chain-capturing bead used in the present invention. The sugar chain-capturing site or sugar chain-capturing group of the bead according to the present invention preferably includes an aminooxy group, an N-alkylaminooxy group, a hydrazide group, an azide group, a thiosemicarbazide group, a cysteine residue, and derivatives thereof.

The term "sugar chain-capturing carrier" as used herein means a carrier for capturing a sugar chain. The term "sugar chain-capturing bead" as used herein means a bead for capturing a sugar chain. Such a carrier or bead includes a part that captures a sugar chain and a part that serves as a carrier or a bead. The part that captures a sugar chain can be formed using a substance which specifically interacts with the sugar chain of the present invention. For the carrier, a support can be used, and the substance which specifically interacts with the sugar chain of the present invention may function as a carrier per se. Such a carrier includes a carrier having "X" in the formula (I) described above. For the bead, any products can be used, and magnetic beads are preferred. Examples of the magnetic beads include those marketed by Dynabead, but are not limited thereto.

The term "captured sugar chain sample" as used herein means a sugar chain sample captured by a sugar chain-capturing carrier or a sugar chain-capturing bead such as described above (for example, beads bound by a sugar chain).

Specifically, such a carrier includes a carrier having "X", "X—Y" and "X—Y—Z" bound to a support, and a carrier resulting from polymerization of compounds represented by formula (I) and formula (II). In general, such a carrier includes, for example, a carrier having a group shown below.

(Sugar Chain-Capturing Functional Group)-(Spacer)-(Polymerizable Functional Group)

Here, the sugar chain-capturing functional group can also be described as, for example, a functional group capable of reacting with the aldehyde group of the sugar chain in a fluid, and has a structure as illustrated in FIG. 2. R in FIG. 2 means the substituent group defined above, but preferably, a substituent group which is not likely to adversely affect the polymerization reaction and the interaction with the sugar chain, is preferred. More specifically, a substance that can specifically interact with the sugar chain of the present invention is a compound which can be represented by the following formula:

X—Y—Z    Formula (I)

Wherein, X is a group represented by the formula:

[Chem 1]

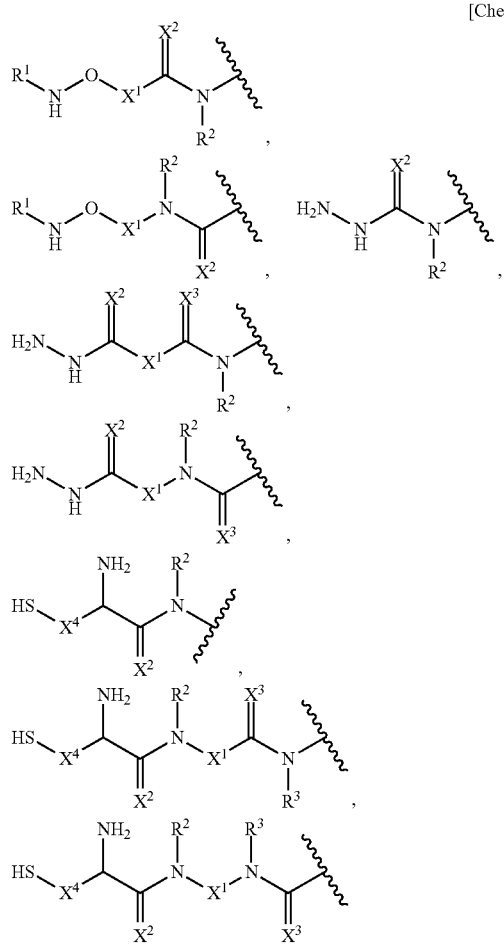

(wherein $X^1$ is an alkylene which may be substituted or an alkenylene which may be substituted; $X^2$ is an oxygen atom or a sulfur atom; $X^3$ is an oxygen atom or a sulfur atom; $X^4$ is methylene or ethylene; $R^1$ is a hydrogen atom or an alkyl; $R^2$ and $R^3$ are each independently a hydrogen atom or an alkyl); Y (the length of Y is equivalent to C0 to C25) is a single bond; an alkylene which may be substituted and may be interrupted by at least one group selected from the group consisting of —O—, —S—, —S—S—, —N($R^a$)—C(=O)—, —C(=O)—N($R^b$)—, and phenylene which may be substituted; or an alkenylene which may be substituted and may be interrupted by at least one group selected from the group consisting of —O—, —S—, —S—S—, —N($R^a$)—C(=O)—, —C(=O)—N($R^b$)—, and phenylene which may be substituted (wherein $R^a$ and $R^b$ are each independently a hydrogen atom or an alkyl); and Z is a group represented by the formula:

[Chem 2]

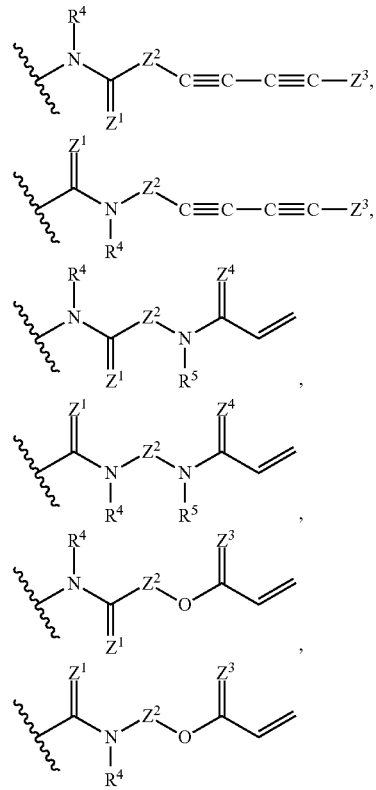

(wherein $Z^1$ is an oxygen atom or a sulfur atom; $Z^2$ and $Z^3$ are each independently an alkylene which may be substituted and may be interrupted by phenylene, or an alkenylene which may be substituted and may be interrupted by phenylene; $Z^4$ is an oxygen atom or a sulfur atom; $R^4$ and $R^5$ are each independently a hydrogen atom or an alkyl). In the compound of formula (I) of the present invention, $X^1$ is preferably a C1-C10 alkylene or a C2-C10 alkenylene, and the chain length of Y is preferably a chain length equivalent to C1-C25 alkyl. Preferred examples of Y include —(CH$_2$CH$_2$—O)$_n$—CH$_2$CH$_2$— (wherein, n=1 to 8 is preferred, and particularly, n=1 to 6 is preferred), and $Z^2$ and $Z^3$ are preferably each independently a C1-C10 alkylene or a C2-C10 alkenylene. Furthermore, specific examples of the phenylene which may be substituted include the following:

[Chem 3]

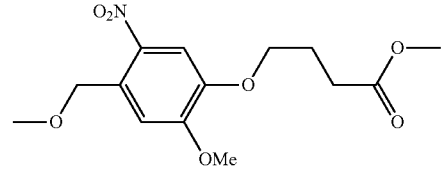

According to a preferred embodiment, a polymer obtainable by polymerizing the compound of the formula (I) is used. Thereby, when various films are formed from a substance that is capable of specifically interacting with the sugar chain of the present invention, the strength and stability of the film itself are enhanced, and furthermore, there is obtained an effect that the film can be fixed to a support such as a substrate. Upon fixing a film to a support, it is preferable to use a technique of polymerizing a monolayer film that is obtainable by physically adsorbing the Z moiety of the compound represented by the formula (I) onto the support. Thereby, a support having a film fixed thereto can be directly used as the sugar chain-capturing carrier of the present invention. Furthermore, the polymerization may be thermopolymerization or may be photopolymerization; however, preferably, an advantage that radical polymerization between diacetylene groups or between vinyl groups in the Z moiety can be made to smoothly proceed, and polymerization can be carried out by a relatively simple operation, is taken into consideration, and photopolymerization by irradiation with ultraviolet (UV) radiation near 254 nm, which is a characteristic absorption wavelength of the diacetylene group or vinyl group, is employed. Furthermore, a substance in which "X" in the formula (I) and a support are directly bound, and a substance in which "X—Y" and a support are directly bound are also employed. As the substituent group for the "alkylene which may be substituted" and the "alkenylene which may be substituted" in $X^1$, absence of substituent is preferred. As the substituent group for the "alkylene which may be substituted" and the "alkenylene which may be substituted" in Y, absence of substituent is preferred. As the substituent group for the "alkylene which may be substituted" and the "alkenylene which may be substituted" in $Z^2$ and $Z^3$, absence of substituent is preferred.

According to another preferred embodiment, the substance that is capable of specifically interacting with the sugar chain of the present invention is a copolymer that is obtained by polymerizing a compound represented by the formula (I):

X—Y—Z    (I):

[wherein, X is a group represented by the formula:

[Chem 4]

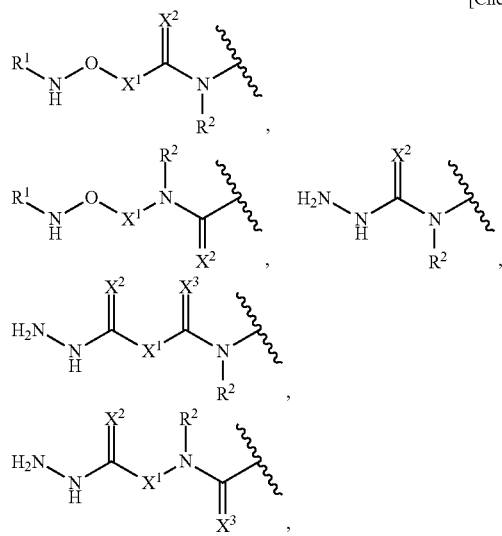

-continued

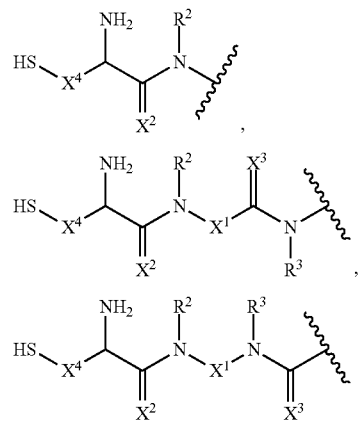

(wherein, $X^1$ is an alkylene which may be substituted or an alkenylene which may be substituted; $X^2$ is an oxygen atom or a sulfur atom; $X^3$ is an oxygen atom or a sulfur atom; $X^4$ is methylene or ethylene; $R^1$ is a hydrogen atom or an alkyl; $R^2$ and $R^3$ are each independently a hydrogen atom or an alkyl); Y (the length of Y is equivalent to C0 to C25) is a single bond; an alkylene which may be substituted and may be interrupted by at least one group selected from the group consisting of —O—, —S—, —S—S—, —N($R^a$)—C(=O)—, —C(=O)—N($R^b$)—, and phenylene which may be substituted; or an alkenylene which may be substituted and may be interrupted by at least one group selected from the group consisting of —O—, —S—, —S—S—, —N($R^a$)—C(=O)—, —C(=O)—N($R^b$)—, and phenylene which may be substituted (wherein, $R^a$ and $R^b$ are each independently a hydrogen atom or an alkyl); and Z is a group represented by the formula:

[Chem 5]

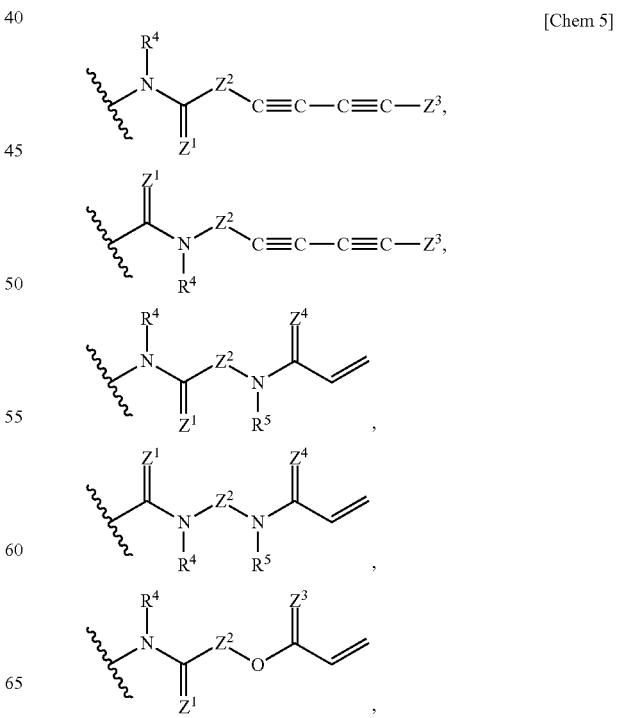

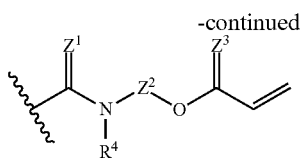

(wherein, $Z^1$ is an oxygen atom or a sulfur atom; $Z^2$ and $Z^3$ are each independently an alkylene which may be substituted and may be interrupted by phenylene, or an alkenylene which may be substituted and may be interrupted by phenylene; $Z^4$ is an oxygen atom or a sulfur atom; $R^4$ and $R^5$ are each independently a hydrogen atom or an alkyl)]; and a compound represented by the formula (II): $A^1$-$A^2$ (II): [wherein, $A^1$ is a group represented by $H(OCH_2CH_2)_nO$— (wherein, n is an integer from 1 to 5) or the formula:

[Chem 6]

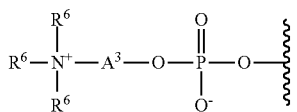

(wherein $A^3$ is an alkylene; and $R^6$ is uniformly an alkyl); and $A^2$ is a group represented by the formula:

[Chem 7]

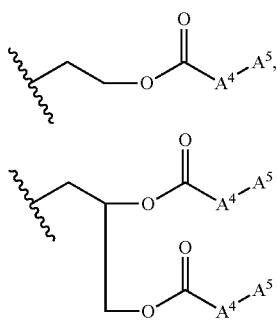

(wherein $A^4$ is uniformly an alkylene; and $A^5$ is uniformly a group represented by the formula:

[Chem 8]

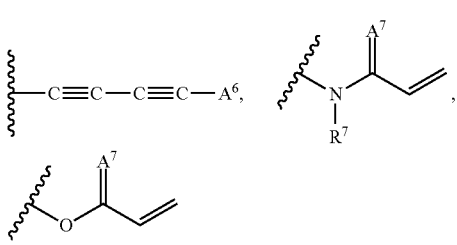

($A^6$ is an alkylene; $A^7$ is an oxygen atom or a sulfur atom; $R^7$ is a hydrogen atom or an alkyl)]. In regard to the copolymer of the compounds of the formulas (I) and (II) of the present invention, $X^1$ is preferably a C1-C10 alkylene or a C2-C10 alkenylene, and the chain length of Y is preferably a chain length equivalent to C1-25 alkyl. Preferred examples of Y include —$(CH_2CH_2$—$O)_n$—$CH_2CH_2$— (wherein, n=1 to 8 is preferred, and particularly, n=1 to 6 is preferred). $Z^2$ and $Z^3$ are preferably each independently a C1-C10 alkylene or a C2-C10 alkenylene, $A^3$ is preferably a C1-C5 alkylene, and particularly preferably a C2 alkylene, and $A^4$ and $A^6$ are each independently a C1-C10 alkylene. Furthermore, specific examples of the phenylene which may be substituted include the following:

[Chem 9]

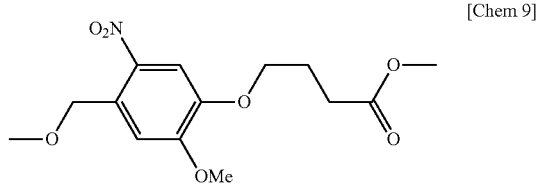

The polymerization may be thermopolymerization, or may be photopolymerization; however, for the same reason as described above, photopolymerization by irradiation with ultraviolet (UV) radiation near 254 nm, which is a characteristic absorption wavelength of the diacetylene group or vinyl group, is preferred.

(Pretreatment Technology for Sugar Chain Analysis)

As used herein, the term "release" of a sugar chain means that the sugar chain is released from a complex containing the sugar chain, which is found in biological materials and the like.

The "sample" as used herein means any sample intended for an analysis of sugar chain. Preferably, the sample is a sample derived from a biological material (for example, a body fluid, a cell extract, or a tissue extract), more preferably a body fluid, a cell extract, a tissue extract or the like, and even more preferably a body fluid containing blood components (for example, serum and plasma). The sample is still more preferably blood, and most preferably blood serum.

The "plate for reaction" as used herein means any plate on which a chemical reaction of a sample containing a sugar chain is carried out. The plate is constituted of a material that does not react or is difficult to react with biological materials, such as plastic. The plate may be coated or may not be coated. As the plate, a generally used experimental plate, such as a multi-well plate, can be used.

The term "solubilizing agent" as used herein means an agent that can solubilize a protein. Examples of the solubilizing agent that can be used include 1-propanesulfonic acid, 2-hydroxy-3-lauramide (PHL), 1-propanesulfonic acid, 2-hydroxy-3-myristamide (PHM), 2-hydroxy-3-sulfopropyl laurate (HSD), or an equivalent thereof. Preferably, 1-propanesulfonic acid, 2-hydroxy-3-lauramide (PHL)/ammonium bicarbonate can be used.

As used herein, the "reaction conditions" for the solubilizing agent mean any reaction conditions that cause a solubilization reaction of the solubilizing agent, including, for example, conditions at 25° C. to 42° C., and preferably at 37° C., for 10 minutes.

The term "reducing agent" as used herein means any substance that adds hydrogen to an element or a compound. As used herein, the reducing agent is used to cleave an —S—S— bond in a protein. The reducing agent may be dithiothreitol (DTT), TCEP (Tris(2-carboxyethyl)phosphine hydrochloride solution, 0.5 M) or an equivalent thereof. Preferably, dithiothreitol (DTT) is used.

As used herein, the term "reaction condition" for the reducing agent means any reaction conditions under which the reduction reaction of the reducing agent proceeds. As used herein, for example, conditions at 50° C. to 80° C. can be used, and preferably, the reaction can be carried out at 60° C. for 30 minutes. Since the temperature is high, the temperature may be returned to room temperature in order to carry out the subsequent reaction.

The term "—SH protective agent" as used herein means any agent that protects the —SH group after an —S—S— bond in a protein is cleaved. As used herein, for example, an agent that is capable of acetylation may be exemplified, and the agent may be, for example, iodoacetamide (IAA) or an equivalent thereof.

As used herein, the term "reaction condition" for the —SH protective agent means any conditions under which the protection reaction of the —SH protective agent proceeds, including, for example, conditions under which the reaction is carried out at 20 to 37° C. in the dark, and preferably at room temperature in the dark, for one hour.

The term "protein digestive enzyme" as used herein means any enzyme that can degrade any polymer of amino acids linked by peptide bond, such as a protein, a polypeptide or a peptide. As used herein, for example, trypsin, chymotrypsin or an equivalent can be used, and preferably trypsin is used.

As used herein, the term "reaction condition" for the protein digestive enzyme means any condition under which the protein degradation reaction by the protein digestive enzyme proceeds, including, for example, the conditions for carrying out the reaction at 25 to 42° C., and preferably at 37° C., for 60 minutes.

The term "deactivation" of the protein digestive enzyme as used herein means that the enzymatic activity of the protein digestive enzyme is lost. Usually, since a protein digestive enzyme is also a protein, "deactivation" can be achieved by denaturing the protein itself at high temperature, but is not limited to this.

The term "sugar chain releasing enzyme" as used herein means any enzyme that can release a sugar chain from a sugar chain complex. As used herein, for example, PNGaseF, Endo H or an equivalent, and preferably PNGaseF, can be used.

As used herein, the term "reaction conditions" for the sugar chain releasing enzyme mean any conditions under which the release of a sugar chain by the sugar chain releasing enzyme proceed. As used herein, such a condition includes, for example, the conditions for carrying out the reaction at 25° C. to 42° C., and preferably at 37° C., for 60 minutes to 12 hours.

The term "a sugar chain-capturing bead" as used herein means any beads having a chemically reactive functional group for the sugar chain capturing as described in the present specification. Such beads are exemplified in, for example, Patent Document 1. Among commercially available products, BlotGlyco (Sumitomo Bakelite), AffiGel Hz (BioRad), CarboLink Coupling Resin (PIERCE), Surface-activated Dynabeads (registered trademark) (Invitrogen) and the like can be used.

As used herein, the phrase "conditions for binding to the sugar chain-capturing bead" mean any conditions under which binding of a sugar chain-capturing group (including, for example, an aminooxy group, an N-alkylaminooxy group, a hydrazide group, an azide group, a thiosemicarbazide group, a cysteine residue, and derivatives thereof) present on a sugar chain-capturing bead (for example, beads or magnetic beads) with the sugar proceeds. For example, such a condition includes, for example, a reaction at 25 to 80° C., and preferably at 80° C.

The term "protein denaturing agent" as used herein means changing properties such as solubility by altering the molecular structure of the protein and the peptide. For example, proteins denature by heating, alkali treatment, acid treatment or the like. Therefore, any of those causing these factors can be exemplified as protein denaturing agents. As used herein, such an agent includes, for example, guanidine hydrochloride, urea, sodium dodecyl sulfate or an equivalent. Preferably, guanidine hydrochloride can be used.

As used herein, the term "reaction condition" for the protein denaturing agent means any conditions under which denaturation of proteins and peptides proceed. As used herein, for example, the conditions may be at room temperature from 10 seconds to 10 minutes, but the time may be even longer than that.

The "residual washing liquid" as used herein means a residual liquid occurring after washing with a washing liquid such as water. Since the residual washing liquid can pose an impediment to the subsequent reactions, it is usually preferable to discard the residual washing liquid.

The term "salt releasing agent" of the sugar chain-capturing group on beads as used herein means any agent that releases a salt (for example, in the case of hydrazide, the salt conjugated to hydrazide) formed with the sugar chain-capturing group (including, for example, an aminooxy group, an N-alkylaminooxy group, a hydrazide group, an azide group, a thiosemicarbazide group, a cysteine residue, and derivatives thereof) on the sugar chain-capturing bead (for example, beads or magnetic beads). In the case of hydrazide, the salt releasing agent is triethylamine or an equivalent, and in the case of aminooxy group, the salt releasing agent is triethylamine or an equivalent. In other cases, the salt releasing agent can be detached by protecting the group using a technology that is known in the related art.

The term "discarding ( . . . ) by suction" as used herein means that a liquid is removed by suction using a film to which liquid is absorbed under reduced pressure or negative pressure (for example, a commercially available multi-well filter plate).

The term "protective agent" as used herein means an agent that protects excess functional groups of the bead. According to the present invention, for example, acetic anhydride, succinic anhydride, other acid anhydrides or equivalents can be used, and preferably acetic anhydride can be used. In this case, protection using an acetyl group (acetylation) is carried out.

As used herein, the term "reaction condition" of the protective agent mean any conditions under which excess functional groups of the bead can be protected. As used herein, conditions using 10% acetic anhydride/methanol at room temperature for 30 minutes, preferably at 37° C., can be employed.

As used herein, the "acid" is used to remove and free the salt from the carboxyl group of sialic acid in the captured sugar chain. Since it is expected that the yield of the methyl esterification reaction would be lowered in the absence of acid treatment, it is preferable to perform an acid treatment. Here, in addition to hydrochloric acid, inorganic acids at pH2 to 3 such as dilute sulfuric acid can be used.

The term "organic reaction solvent" as used herein means any organic solvent used in a reaction such as an alkyl esterification reaction. For example, dioxane, as well as acetonitrile and tetrahydrofuran can be used. The preference for either dioxane or acetonitrile may vary with the bead.

The term "hydrophilic organic solvent" as used herein means any organic solvent that is used intermediately when a hydrophobic organic solvent is exchanged with water (that is, mediates between a water-based system and an organic solvent). For example, a lower alcohol such as methanol or ethanol, acetonitrile, acetone or the like can be used.

The term "removal" of "moisture and solvent" as used herein means any process capable of removing moisture and solvent. Alternatively, the removal also includes exclusion of a water-based solvent after a use of the water-based solvent, by purging the solvent environment of the bead with an organic solvent. For example, bottom wiping with a filter paper, a blotting paper, gauze, a towel, a hand towel, a tissue paper, a cotton sheet or the like, may be exemplified. The means used in the "removal" of "moisture and solvent" (also referred to as "solvent absorbent sheet" in the present specification) is a material which is used to absorb the solvent that has adhered to the low side of the plate, such as water, acetonitrile (ACN) or methanol, after the plate has been subjected to suctioning under reduced pressure. The means is not limited to a specific material such as cotton, as long as it is made of a material capable of absorbing moisture and solvent. If not wiped out, the solvent penetrates back onto the filter, and the bead on the filter happen to contain more moisture and solvent. Thus, it is preferable to prevent this.

The term "bottom wiping at . . . " as used herein means that a means for absorbing moisture and solvent (for example, a solvent absorbent sheet such as cotton sheet) is spread out at the bottom, and the plate which has been filtered by suction is placed thereon and pressed from the top, so as to remove the filtration solvent adhering to the bottom of the plate, by absorbing the filtration solvent into the absorbent sheet.

The term "alkyl esterifying agent" as used herein means any agent that can achieve alkyl esterification. For example, in the case of methylation, the reaction is called methyl esterification. When the carboxylic acid of sialic acid is methylated, there is obtained an effect of making the detection of sugar chain easier. This technology is described in WO 2007/099856, the disclosure of which is incorporated to the present specification by reference as necessary. As used herein, for example, methyl-p-tolyl-triazene (MTT), ethyl-p-tolyl-triazene (ETT), butyl-p-tolyl-triazene (BTT), or an equivalent can be used.

As used herein, the term "reaction condition" for the alkyl esterifying agent means any conditions under which an alkyl esterification reaction using an alkyl esterifying agent proceeds. As used herein, for example, conditions using 100 mM MTT/dioxane at 60° C. for 60 minutes can be employed.

The term "tagging" as used herein means that a material for mass spectrometry, such as a sugar chain, is bound to an additional molecule such as a label in order to prepare for detection. Such tagging is carried out using a chromophore capable of absorbing ultraviolet and visible rays, a tag having a structure emitting fluorescence, an affinity tag having a molecule capable of interacting with other molecules (His tag, biotin, or the like), a tag having a functional group capable of specifically reacting with a functional group (a photoreactive molecule (for crosslinking), an azide group, an SH group, an amino group, carboxylic acid), a tag having a functional group in a hydrophobic structure, or a tag having a metal ion ligand. Tagging may be carried out in the additional presence of acetic acid, acetonitrile, an acetate buffer solution, or an equivalent.

The term "reagent" for tagging as used herein means any reagent capable of tagging, including, for example, a chromophore capable of absorbing ultraviolet and visible rays, a tag having a structure emitting fluorescence, an affinity tag having a molecule capable of interacting with other molecules (His tag, biotin, or the like), a tag having a functional group capable of specifically reacting with a functional group (a photoreactive molecule (for crosslinking), an azide group, an SH group, an amino group, carboxylic acid), a tag having a functional group in a hydrophobic structure, or a tag having a metal ion ligand.

The term "chromophore capable of absorbing ultraviolet and visible rays" as used herein means any chromophore that absorbs ultraviolet and visible rays, including, for example, an aromatic compound such as p-nitrobenzyloxylamine.

The term "tag having a structure emitting fluorescence" as used herein means any tag that has a structure emitting fluorescence, including, for example, anthraniloyl hydrazine.

The term "affinity tag having a molecule capable of interacting with another molecule" as used herein means any tag having a molecule that can interact with another molecule, including, for example, His tag, biotin, biotin hydrazide and the like.

The term "tag having a functional group capable of specifically reacting with a functional group" as used herein means any tag having a functional group that specifically reacts with a functional group, and for example, a photoreactive molecule (for crosslinking), an azide group, an SH group, an amino group, carboxylic acid, N-aminooxyglycine, including, for example, a compound having the compound structure in the molecule.

The term "tag having a functional group in a hydrophobic structure" as used herein means any tag having a functional group in a hydrophobic structure, and for example, a hydrazide compound having a hydrophobic aromatic or hydrophobic aliphatic chain; including, for example, Girard Reagent P.

The term "tag having a metal ion ligand" as used herein means any tag having a metal ion ligand, including, for example, a histidine tag or a tag that can adsorb to a metal ion-carrying resin.

The term "tagged sugar chain sample solution" as used herein means any sample that has been prepared to contain a tagged sugar chain. This solution can be directly subjected to analysis by HPLC, or liquid chromatography-mass spectrometry (LC-MS) or the like, but can also be fixed on a plate for MALDI-TOF mass spectrometry and subjected to MALDI-TOF mass spectrometry.

The term "detection sample" as used herein means a sample for detection in mass spectrometry or the like.

The term "plate for mass spectrometry" as used herein means any plate used for mass spectrometry. The plate is constituted of a material that does not react or is difficult to react with biological materials, such as plastic or metal. The plate may be coated, or may not be coated. For example, a sample-dotted plate that depends on the MALDI apparatus can be used.

The term "plate for recovery" as used herein means any plate used for the recovery of sample. The plate is constituted of a material that does not react or is difficult to react with biological materials, such as plastic. The plate may be coated, or may not be coated. As the plate, a generally used experimental plate such as a multi-well plate can be used.

The term "multi-well" as used herein means a large number of wells, and a multi-well plate means a plate having a large number of wells. For example, a multi-well plate having 96 wells, a multi-well plate having 384 wells, a multi-well plate having 1536 wells, and the like can be mentioned as examples.

The term "resin or membrane suitable for solid phase extraction" as used herein means any resin or membrane used for solid phase extraction. In the present specification, such a resin or membrane includes, for example, C18 silica gel, solid phase carrier for normal phase, amino-functionalized silica resin and the like.

The term "solid phase" as used herein means a solid state.

The term "concentration at which the sugar chain adsorbs to a solid phase" as used herein means any concentration at which adsorption of a sample (for example, sugar chain) to a substrate or the like in the solid state is accelerated.

The term "plate for mixing" as used herein means any plate used for mixing two or more reagents or samples. The plate is constituted of a material that does not react or is difficult to react with biological materials, such as plastic. The plate may be coated, or may not be coated. As the plate, a generally used experimental plate such as a multi-well plate can be used.

The term "solid phase carrier-enclosed plate" or "SPE plate" as used herein means a column type plate for multiple sample treatment, which encloses a carrier for solid phase extraction. The plate is constituted of a plate material that does not react or is difficult to react with biological materials, such as plastic; microbeads made of silica or styrene having a functional group such as aminopropyl or octadecyl, which are enclosed as a carrier for solid phase extraction; and a filter for retaining the carrier for solid phase extraction. The plate may be coated, or may not be coated. As the plate, a generally used experimental plate such as a multi-well plate can be used. One of example products includes "MassPREP HILIC μElution Plate" manufactured by Waters Corp.

The phrase "conditioning to a solvent having a polarity appropriate for the phase" as used herein means that a certain material is made compatible with a solvent having an opposite polarity (if water, a hydrophobic material; if a hydrophobic organic solvent, a hydrophilic material). For the acclimation, it is preferable to immerse the material in the solvent for a long time, or to exchange the solvent several times.

The term "second plate for recovery" as used herein means a plate which is intended for conducting recovery again after an operation in which a plate for recovery is used, and then purification operation is carried out with the solid phase carrier-enclosed plate.

The term "matrix for mass spectrometry" as used herein means any matrix for preparing a sample for mass spectrometry. The matrix will be described in detail in other part of the present specification.

The term "analysis of mass of a sugar chain" as used herein means any technique for analyzing the mass of a sugar chain. The methods described in the present specification, such as high performance liquid chromatography (HPLC), an LC-ESI-TOFMS method or a MALDI-TOF method, and any techniques known in the related art can be used.

The term "process of removing excess" reagent as used herein means any process of removing the reagent used in a reaction. For example, for the purpose of removal, such a process includes, for example, washing several times with a solvent only, or the like.

The term "pretreatment sample for analyzing a sugar chain in a sample" as used herein means a sample used for analyzing a sugar chain in a sample. Usually, in mass spectrometry or the like, it is impossible to carry out analysis with a fresh sample as received. Thus, it is necessary to carry out a pretreatment such as removing impurities or tagging, and a sample that has been subjected to such pretreatment is called as such in the present specification.

(Method for Mass Spectrometry)

The term "mass spectrometry" as used herein means that particles such as atoms, molecules or clusters are converted into gaseous ions (that is, ionized) and are allowed to move about in a vacuum, and those ions are separated and detected using an electromagnetic force in accordance with the mass charge ratio (m/z). A spectrum obtained based on the ions separated and detected in accordance with m/z, representing m/z on the horizontal axis and the relative intensity of ions on the vertical axis, is a mass spectrum. The ions that give information on the molecular weight are generally referred to as molecular weight-related ions (there are available $M^+$ resulting from a loss of one electron from a neutral molecule M; $M^-$ resulting from addition of one electron; $[M+H]^+$ resulting from addition of a proton; $[M-H]^-$ resulting from a loss of a proton; $[M-H]^+$ resulting from a loss of a hydride; $[M+Na]^+$ resulting from addition of an alkali metal (such as Na); and the like). Depending on the sample or the ionization method (especially, in the EI method), the molecular weight-related ions may never appear; however, in that case, the molecular weight-related ions can be confirmed by using a mild ionization method. Those ions appearing on the lower mass side than molecular ions are called fragment ions, and these fragment ions are degradation products of molecular ions and give information on the structure of the sample molecule. The ion with the highest ion intensity in the spectrum is called a base peak, and this is used to normalize the spectrum by taking the relative intensity as 100%.

The "ionization" according to the present invention is carried out by appropriately selecting one among the following 7 methods.

1) Electron Ionization Method (EI Method)

The electron ionization method is a method of ionizing by contacting hot electrons to a gasified sample, and is the most popularized ionization method. Since ionization is conducted after gasifying the sample, it is necessary to gasify a liquid or solid sample in advance. Because heat is applied for the process of gasification, measurement of a heat-unstable substance or a sparingly volatile substance is impossible. However, in the case of a substance which can attain volatility and thermal stability by derivatization such as methylation, silylation or acylation, measurement can be made. Since ionization is usually carried out with energy of 70 eV, fragment ions are generated by excess energy, along with the generation of molecular ions (the ionization energy for a general organic compound is about a dozen eV). Structural analysis of the compound is made possible from the information on these fragment ions. However, because it is difficult to obtain molecular ions, the molecular weight information is often unobtainable. In this case, it is necessary to drop the ionization energy to about 20 eV, or to select a milder ionization method (CI, DEI, DCI, FAB or ESI).

2) Chemical Ionization Method (CI Method)

It is a method of ionizing a gasified sample by sending the sample into a previously ionized reaction gas (reagent gas). Since this method achieves ionization using an ion-molecule reaction, the ionization energy is close to the ionization energy of organic compounds, and thus the amount of fragment ions is very small, while ions having the molecular weight information (($M+H)^+$, $(M+NH_4)^+$, $(M-H)^-$, and the like) appear as base ions. As the reaction gas, generally methane, isobutane or ammonia is used.

3) Desorption Electron Ionization Method (DEI Method)

This is a method of conducting instantaneous heating near an electron beam, and thereby gasifying and ionizing the sample before the sample undergoes thermal degradation. Measurement of heat-unstable substance or a sparingly volatile substance is made possible. Furthermore, since molecular ions appear with stronger intensity as compared to the EI method as a conventional method of direction introduction, it is easier to obtain the molecular weight information. The measurement method involves attaching a sample solution at the tip of a point filament (platinum wire having a diameter of 100 μm), inserting the point filament into an ion source, and then rapidly heating the filament to gasify the sample.

4) Desorption Chemical Ionization Method (DCI Method)

When the operation of DEI is carried out, with the ion source being put in the CI state, this operation is the DCI.

5) Fast Atom Bombardment Method (FAB Method)

This is a method of thoroughly mixing the sample and matrix molecules, applying the mixture on a target, and bombarding fast neutral atoms such as Xe thereon to ionize the sample. Unlike the EI and CI, it is not needed to gasify the sample, and therefore, the method is adequate for the measurement of a heat-unstable substance or a sparingly volatile substance. However, since intense matrix-derived background peaks appear in the lower mass region, measurement of a low molecular weight sample may be difficult in some cases. In that case, measurement by FRIT-FAB is effective.

6) FRIT-Fast Atom Bombardment Method (FRIT-FAB Method)

This method is also called as Continuous-flow FAB, and is a method of making the sample dissolved in a matrix solution to flow continuously, and bombarding the eluent outlet with fast neutral atoms to ionize the sample.

7) Electrospray Ionization Method (ESI Method)

This is an atmospheric pressure ionization method that makes use of the phenomenon in which when high voltage is applied on a capillary, the sample solution spontaneously undergoes spraying and ionization. Just like FAB, there is no need to gasify the sample, and therefore, the method is adequate for the measurement of a heat-unstable substance or a sparingly volatile substance. This makes it possible to measure a peptide or protein having a large molecular weight, even for the quadrupole type with a small mass range. In the conventional ESI measurement, because fragment ions having the structural information are not obtained, in-source CID occurs as a voltage slightly higher than usual is applied to Capillary/Skimmer-1, and thus measurement of fragment ions having the structural information is made possible.

The term "MALDI-TOF MS" as used herein is an abbreviation for Matrix Assisted Laser Desorption Ionization-Time-of-Flight (Mass Spectrometer). MALDI is a technique discovered by Tanaka et al., and developed by Hillenkamp et al. (Karas M., Hillenkamp, F., Anal. Chem. 1988, 60, 2299-2301). In this method, the sample and a matrix solution are mixed at a molar ratio of $(10^{-2}$ to $5 \times 10^{-4})$:1, and then the mixed solution is dried to solid on a target to bring it to a crystalline state. Large energy can be applied on the matrix by pulse laser irradiation, and sample-derived ions such as $(M+H)^+$ and $(M+Na)^+$, and matrix-derived ions are desorbed. Analysis can be still made even if the sample is contaminated with a trace amount of phosphate buffer solution, Tris buffer solution, guanidine or the like. MALDI-TOF (MS) allows measurement of mass using MALDI, based on the time of flight. When ions are accelerated at a constant accelerating voltage V, and when the mass of the ion is designated as m, the velocity of the ion as v, the charge number of the ion as z, the elementary electric charge as e, and the time of flight of the ion as t, the m/z of the ion can be represented by:

$$m/z = 2 \, eVt^2/L^2$$

In the measurement of MALDI-TOF as such, KOMPACT MALDI II/III by Shimadzu/Kratos, or the like can be used. At the time of measurement, reference can be made to the pamphlet produced by the manufacturer. The irradiation energy of the laser irradiation used upon the measurement of MALDI-TOF is referred to as "dissociation energy" in the present specification.

The term "LDI-TOF MS" as used herein means a method of desorbing and ionizing intended molecules by laser irradiation without using a low molecular weight matrix reagent, contrastingly to the "MALDI-TOF MS".

The term "identical entity" as used herein means that an entity that is expressed in plurality for convenience in the present specification, is the same individual itself.

The "metal" as used herein means a metal element or a metal composite containing a metal capable of binding, at least partially, to a sulfur atom-containing substance (for example, thiol, disulfide or the like). Representative types of the metal capable of binding to a sulfur atom-containing substance include gold, silver, cadmium, selenium and the like. The metal may also be a magnetic substance.

The term "metal microparticles" as used herein mean particles of metal defined as having an average particle diameter size of 10 nm to 1 μm, and the microparticles may be of monodisperse type or polydisperse type. The bead may be constituted of such metal microparticles. When the metal microparticles constitute a metal composite, the surface of the particles which serve as the core of the complex, takes a structure covered by a layer of a metal to which the sulfur atom-containing substance can bind. Representative metal microparticles used in the present invention include microparticles of elemental gold or silver metal, or microparticles of a metal composite formed from magnetic particles of iron, nickel, cobalt, iron oxide ($Fe_3O_4$) or the like having the surface covered with gold or silver. The "metal microparticles" of the present invention form a colloid in a solution. In addition to the examples of the metal microparticles listed above, Quantum Dots (trade name) (Quantum Dot Corporation, Hayward, Calif., USA; hereinafter, referred to as "QDs") can also be used. Examples of the type of metal used in the QDs include ZnSe, CdS, CdSe, CdTe and the like. A typical example is nanoparticles having CdSe in the core, and ZnS surrounding the core. An —SH compound can be presented at the QDs surface through the bond between Zn, which is emerging from the surface, and —SH (this bond is of the same type as Au—S). In regard to the production of gold microparticles and applications thereof, descriptions are found in JACS 125, 7790-7791 (2003); Angew Chem Int Ed 40(12), 2257-2261 (2001); and Chem Eur J 9, 1909-1921 (2003).

(Application of Apparatus of Present Invention)

A proteome analysis combining an analysis method for sugar chain, which is based on the mass spectrometric method realized by the present invention, and a two-dimensional electrophoresis method, also makes research aimed for rapid identification of a protein marker engaged in a disease, or high-throughput search for a target protein which serves as a target of genomic drug discovery, to be actively carried out.

Sugar chain modification is a very important and fundamental biosynthesis process in the protein dynamic structure/function controlling mechanism, together with phosphorylation, acylation, prenylation reactions and the like. Such various modification reactions for protein are broadly called "post-translational modification of genetic information," which is a phenomenon deeply involved in many diseases including cancer and immunity. Therefore, sugar chain modification is useful in the development of new diagnosis support technologies or research and development of medicines, and even in the field of clinical practice.

When the present invention is used, it is also possible to carry out high throughput quantitative glycomics as well as an analysis of peptide sequence information of the carrier protein of those sugar chains, and a study of making a search for a new disease biomarker, which adopts, as a basic strategy, "glycoform-focused reverse genomics" which further traces back to identification of genomic data.

By using the present invention, glycoform-focused reverse genomics (GFRG) can be carried out, which is a method of catching a glycopeptide fragment while considering the sugar chain as a tag, thereby proceeding a proteomic analysis as well as obtainment of genomic data all at one time, and thus implementing identification of glycoproteins, profiling of heterogeneity of sugar chains, and the like. "High throughput quantitative glycomics" is possible, in which sugar chains obtainable from various types of glycoproteins contained in biological samples of blood serum, cells, tissues and organs by N-glycanase digestion or the like, are selectively or comprehensively captured and labeled, and all of sugar chain structures and their quantitative distribution state are analyzed by high performance liquid chromatography (HPLC), an LC-ESI-TOFMS method or the like. Partially digested glycopeptide fragments obtainable from the same sample by a peptidase treatment, are captured for each of the respective intended sugar chain structural groups, the respective peptide sequences are determined by MALDI-TOFMS and MALDI-TOF/TOFMS analyses, and the like, and the results are combined with the results of the above-described high throughput quantitative glycomics analysis. Thereby, "Glycoform-focused proteomics" that confirms the individual glycopeptide structures can be carried out. In this case, for example, if a protein containing the peptide structure can be picked up by using the MASCOT algorithm (Matrix Science, Ltd., the total image of the glycoprotein containing genetic information can be instantaneously analyzed and identified. The GFRG method which traces back in the reverse direction and analyzes the structures of a carrier protein, and even a gene, from a sugar chain tag, is one of high throughput search methods for new disease markers, and is expected to be a promising strategy.

In the GFRG method, two types of trace amount sugar chain structural analysis technologies such as (1) high throughput quantitative structural analysis of sugar chains and (2) structural analysis of glycopeptides, are used.

There, a glycoblotting method can be used.

A sugar chain released from a complex glycoconjugates such as a glycoprotein, a proteoglycan or a glycolipid, necessarily has a hemiacetal group equivalent to an aldehyde group at a reduced terminus in the molecule. Thus, perfect chemical differentiation from other biomolecules such as amino acids and peptides which constitute proteins, nucleotides which constitute DNA/RNA, and lipids, is realized by a specific and selective nucleophilic addition reaction to this hemiacetal group. Various substances (irrespective of high molecular weight or low molecular weight) containing a functional group that reacts comprehensively with the reduced termini of all sugar chains (an aminooxy group, a hydrazide group, or the like) are used to perform sugar chain capturing, probe labeling using a high sensitizing reagent or the like, and structural analysis of the substances according to the mass spectrometric methods, continuously at high speed (Patent Document 1; FIG. 3).

By using the present technique, the process for quantitative structural analysis of an asparagine-binding type sugar chain released from various glycoproteins included in a serum sample (about 50 microliters) can be simplified and shortened to a large extent. In the conventional methods only of combining various chromatographic operations, even those processes of sugar chain purification from a test sample containing a large amount of foreign materials or pretreatment of a fluorescence label only require cumbersome operation taking about 2 to 3 weeks (N. Tomiya, et al. Anal. Biochem. 171, (1988)), but according to this new method, a series of processes from sugar chain capturing to comprehensive structural analysis according to various mass spectrometric methods such as MALDI-LIFT-TOF/TOF or nanoLC/ESI-TOFMS, can be completed within half a day. Furthermore, when a selective oxidation reaction (functional group conversion) in galactose with non-reducing termini or in sialic acid residue is carried out, followed by an oxime formation reaction at this position, glycopeptide fragments can be blotted. Thus, a scheme as shown in FIG. 3 can be applied to the structural analysis of a glycopeptide.

Fragment ions of a sugar chain can be detected before being destroyed.

Mass spectrometric methods are being used already widely in various aspects as very effective analytic methods for the proteome research. This is because the methods are highly advantageous in that all of the peptide fragments produced by enzymatic digestion or the like can be easily ionized without depending on their structures, and that selective fragmentation from their stable primary ion peaks is also simple, so that when MS/MS spectrum patterns are collated using the above-described MASCOT algorithm analysis or the like, candidate proteins including those peptide sequences can be easily conjectured.

Furthermore, MALDI-TOF MS (for example, REFLEX III and BIFLEX III by Bruker Daltonics, Ltd., or the like) can be used as a simple and general-purpose method of monitoring the reactions for enzymatic or chemical sugar chain modification performed on peptides or proteins. In these apparatuses, optimization of reaction conditions, evaluation of the reaction yield, and the like can be carried out by simply identifying the molecular weight of a reaction product, mainly from the information on monovalent molecular ion peaks only. Ultraflex, which is a higher-end model than the two apparatuses, can detect and analyze unstable fragment ions with high sensitivity at high speed by the LIFT-TOF/TOF method. It is thought that similar measurement in the TOF/TOF mode can also be made with MALDI type mass analyzing apparatuses of other companies, but the basic principle is such that, as shown in FIG. 4, in TOF-1, an accelerating voltage is selectively applied to precursor ions subsequently to laser irradiation, thereby generating fragment ions. Then, each of these fragment ions is rapidly subjected to instantaneous accelerating voltage again at the stage where the fragment ions have reached a region called TOF-2, and the fragment ions move directly to the detector through a reflector at a certain voltage so that the respective masses are identified. The most important point herein is that all of the fragment ions which have been accelerated in the TOF-2 region and made to move at respectively different speeds, begin to be detected from after several microseconds and are successively detected during a period up to several hundred microseconds thereafter. For comparison, the measurement in the PSD mode is presented on the same time axis, but in this case, since all the fragment ions come toward the detector all at a time by uniform linear motion, a process of sorting and then detecting each of the fragment ions by appropriately changing the voltage at the reflector in the middle, is required. Consequently, all of the fragment ions take about 1 millisecond after ionization to reach the detector. Upon detecting and structurally analyzing those unstable fragment ions observed in the sugar chain rapidly with high sensitivity, the "time-differential attack" of this several hundred microseconds is important. As such, when various methods are attempted for use, the automatic analysis method of the present invention is applicable.

By using the LIFT-TOF/TOF method, it has been made possible to observe with good reproducibility the molecular ion peaks or fragment ion peaks of various mucin type glycopeptides including these structures, without cleaving the O-glycoside bond with serine or threonine (faster than cleaving). Since the TOF/TOF mass spectra of relatively large sugar chains including sialic acid or fucose can also be obtained with good reproducibility through a simple operation, it is now possible to identify structural isomers or to analyze the composition ratio of isomers in an unknown sample, through a combination with the TOF/TOFMS spectra of a so-called known compound (spectrum matching method). In regard to the spectrum matching of sugar chains, for example, a method for prediction of unique MS/MS patterns by GlycosidiQ™, which is loaded in the GlycoSuite DB developed by Proteome Systems, Inc., has been already reported. In this method, the spectrum pattern of actually observed fragment ions and the calculated database of the fragment ions obtained by a theoretical simulation based on the characteristics of the disintegration behavior of the sugar chain, are automatically collated, and from the homologousness, a candidate structure is speculated. By using an MS/MS database of more various and complicated sugar chain-related compounds, spectrum matching with high accuracy can be achieved.

The sonic spray ionization (SSI) method, which is excellent in the ionization of unstable molecules of natural substances, metabolic intermediates and the like, can be said to be one of optimal methods for non-destructive direct ionization of sugar chain. In Hitachi M-8000 3DQ type mass analyzing apparatus (manufactured by Hitachi High-Technologies Corp.) loaded with this SSI method, stable molecular ion peaks are detected with high sensitivity even for various oligosaccharide samples including neutral sugar chains as well as sialic acid when measurement is made in the negative ion mode, and even the four kinds of structural isomers of sialic acid produced as a result of the difference in the bonding mode can be perfectly discriminated by $MS^n$ spectrum matching obtainable from CID (collision induced dissociation) of helium gas. Since the MS, $MS^2$ and $MS^3$ spectra of these isomers are available, and the position of branch in $MS^2$ has been identified, when the $MS^3$ spectrum is compared, discrimination of the $\alpha 2,6$ bond and the $\alpha 2,3$ bond, which link sialic acid with galactose residue, can be simply carried out. However, when conducting an analysis of sugar peptides which closely resemble in the molecular weight and structure, a throughput enhancement combined with an excellent separation method such as nanoLC technology is being expected.

Matrix Dependent Selective Fragmentation (MDSF) Method 2,5-Dihydroxybenzoic acid (DHB) and α-cyano-4-hydroxycinnamic acid (CHCA) are two typical matrices frequently used in the MALDI method. When TOF/TOFMS measurement is made on molecular ions which have been produced each independently using these 2 kinds of matrices, even though a completely same accelerating voltage is applied to TOF-2 for the molecular ions having the same mass, completely different fragment ion patterns are observed. This is conceived to be due to the difference in the distribution mode of charges in the activated molecular ions. While in the fragmentation from the molecular ions produced with DHB, most of the disintegration patterns are of exo type in which monosaccharides are dissociated one by one from the end, on the contrary, in the case of the production with CHCA, disintegration of endo type in which relatively large sugar chain fragment ions are conspicuously observed dominates. When molecular ions produced with DHB, having a value of m/z 1862.79 ($M+H^+$) are selected and fragmentation is carried out, satisfactory fragmentation occurs at the peptide area, in addition to the exo type disintegration of sugar chains from the terminus. On the other hand, three types of compounds which have sugar chains of the same structure and differ in the aglycone moiety (glycopeptide, glycoamino acid and fluorescent-labeled sugar chain) were ionized, this time using CHCA as the matrix. When the molecular ions ($M+Na^+$) produced thereby, which respectively have definitely different mass numbers, are fragmentized, it is also possible to perform structural analysis of the sugar chain moiety through spectrum matching. This matrix-dependent selective fragmentation (MDSF) method is a method effective for selective fragmentation of glycopeptides in which glycoside bond and amide bond co-exist in a same molecule.

For the GFRG method, there is a need to receive the results of high throughput quantitative glycomics and to perform a systematic analysis for each of the target sugar chain structures, including the root peptide structure (glycoform focused proteomics). Therefore, it is preferable to use, in connection with MALDI-TOFMS, a selective $MS^3$ spectrum in the MDSF method or ESI (SSI) ion trap MS method, and to use a technology intended for more selective and accurate fragmentation such as electron capture dissociation (ECD) method.

(Constitution of Analyzing Apparatus)

As an example of the apparatus of the present invention, the constitution proposed in FIG. 9 can be used.

The following processes can be carried out at the respective position numerals in FIG. 9.

Position Numeral

Reaction, Treatment Carried Out at the Position (1) A glycoprotein is treated with a proteolytic enzyme and a sugar chain releasing enzyme to thereby release a sugar chain.

(2) to (5) The sugar chain is captured using BLOTGLY-COABC beads, and the reduced terminus of the sugar chain is labeled.

Impurities that are not captured by the bead are removed by filtration.

The carboxylic acid of the sialic acid residue is protected by methyl esterification.

The hydrazone bond is reduced to thereby stabilize the bond with the bead.

The S—S bond is cleaved to release the sugar chain from the bead.

The sugar chain is filtered.

(6) to (7) A MALDI matrix is added to the sugar chain-containing filtrate/sugar chain effluent, and then the mixture is dropped on a MALDI plate.

(8) to (10) When having a small sugar content, or when performing HPLC analysis, this operation is carried out.

A liquid prepared by mixing ACN with the filtrate containing the sugar chain, is flowed over an SPE plate which has been washed with ACN, and the sugar chain is adsorbed to the SPE plate.

The SPE plate is washed with 95% ACN, and excess reagents are removed.

10% ACN is flowed to effuse the sugar chain from the SPE plate.

Another exemplary embodiment is shown in FIG. 5 to FIG. 6. In these diagrams, the positions in the apparatus as shown in FIG. 1 are presented with numerals. FIG. 7 shows an example of dispensing. FIG. 8 shows a bird's-eye view of this embodiment.

The washing valves A to H in FIG. 8 are as follows.

A more preferred embodiment is shown in FIG. 1.

In this FIG. 1, the following process is carried out.

A method for analyzing a sugar chain in a sample, the method comprising the following steps:

A) a sugar chain releasing step of releasing a sugar chain in a sample, the step comprising the following steps:

- A-1) a step of providing blood serum as a sample on a filter plate;
- A-2) a step of adding 1-propanesulfonic acid, 2-hydroxy-3-lauramide (PHL) or 1-propanesulfonic acid, 2-hydroxy-3-myristamide (PHM)/ammonium bicarbonate, and allowing the mixture to react for 10 minutes at 37° C.;
- A-3) a step of adding dithiothreitol (DTT) to the sample, allowing the mixture to react for 30 minutes at 60° C., and then cooling the reaction mixture to room temperature;
- A-4) a step of adding iodoacetamide (IAA), and allowing the mixture to react for 1 hour at room temperature in the dark;
- A-5) adding trypsin to the sample, and allowing the mixture to react for 60 minutes at 37° C.;
- A-6) heating the sample to 90° C. for 5 minutes, and then cooling the sample to room temperature; and
- A-7) adding PNGaseF, and allowing the mixture to react for 12 hours at 37° C.;

B) a detection sample preparing step of preparing the released sugar chain for use in detection, the step comprising the following steps:

- B-1) a step of contacting the captured sugar chain sample prepared in the step (A) with beads for capturing sugar chain, to thereby allow binding at 37° C., and thus producing a captured sugar chain sample;
- B-2) a step of adding guanidine hydrochloride to the captured sugar chain sample to thereby place the captured sugar chain sample under a reaction condition, and then discarding the reaction liquid by suction;
- B-3) a step of washing the captured sugar chain sample with water, and then discarding the water by suction;
- B-4) a step of washing the captured sugar chain sample with triethylamine, and then discarding the triethylamine by suction;
- B-5) a step of adding acetic anhydride to the captured sugar chain sample to thereby place the captured sugar chain sample under the reaction conditions, and then discarding the acetic anhydride by suction;
- B-6) a step of adding hydrochloric acid to the captured sugar chain sample, and discarding the hydrochloric acid by suction;
- B-7) a step of adding methanol to the captured sugar chain sample, discarding the methanol by suction, and then adding dioxane to the captured sugar chain sample;
- B-8) a step of wiping the bottom with a cotton sheet;
- B-9) a step of adding methyl-p-tolyl-triazene (MTT) to the captured sugar chain sample, and allowing the mixture to react for 60 minutes at 80° C.;
- B-10) a step of adding dioxane to the captured sugar chain sample, and discarding the dioxane by suction;
- B-11) a step of washing the captured sugar chain sample with methanol, discarding the methanol by suction, washing the sample with a NaCl solution, discarding the NaCl solution by suction, washing the sample sequentially with water, and then discarding the water by suction;
- B-12) a step of adding acetic acid and acetonitrile to the captured sugar chain sample, and tagging the sugar chain in the captured sugar chain sample using aminooxytryptophanyl arginine methyl ester/water, benzylhydroxylamine hydrochloride/water, or anthraniloyl hydrazine/water; and
- B-13) a step of adding water to the tagged captured sugar chain sample to produce a tagged sugar chain sample solution;

C) a step of producing a plate for mass spectrometry having the tagged captured sugar chain sample dotted thereon, the step comprising:

- C-1) a step of disposing the tagged sugar chain sample solution obtained in the step (B) on a plate for recovery;
- C-2) a step of disposing the tagged sugar chain sample solution from the plate for recovery and acetonitrile on a plate for mixing, so as to achieve a final concentration of acetonitrile of 80 to 90%;
- C-3) a step of providing a solid phase carrier-enclosed plate which is in normal phase mode;
- C-4) a step of washing the solid phase carrier-enclosed plate sequentially with water and acetonitrile, and discarding water and acetonitrile by suction;
- C-5) a step of adding the tagged sugar chain sample solution to the solid phase carrier-enclosed plate, discarding the liquid, and adding 5% acetonitrile thereto;
- C-6) a step of recovering the bead by suction from the solid phase carrier-enclosed plate to the second plate for recovery; and
- C-7) a step of adding 2,5-dihydroxybenzoic acid in 30% acetonitrile, to the tagged sugar chain sample solution, and mixing and dotting the mixture; and D) a step of performing mass spectrometry by MALDI-TOF MS.

The numerals in FIG. 1 are as described in the section EXPLANATIONS FOR LETTERS AND NUMERALS.

The following are deployed for the reagent rack 4° C., reagent rack, and washing valve.

TABLE 1

|  | mL |
|---|---|
| Reagent rack 4° C. | |
| Trypsin | 0.48 |
| PNGaseF | 0.48 |
| Reagent rack | |
| PHL | 1.92 |
| DTT | 0.48 |
| IAA | 0.96 |
| 10% Ac2O | 9.6 |
| MTT | 9.6 |
| 20 mM reagent | 1.92 |
| 5% ACN | 9.6 |
| Washing valve | |
| 2% AcOH in ACN | 34.56 |
| 2M guanidine hydrochloride | 38.4 |
| water | 86.4 |
| 1% TEA | 38.4 |
| 10 mM HCl | 38.4 |
| MeOH | 38.4 |
| Dioxane | 57.6 |
| 95% ACN | 72.96 |

It should be understood that the process described above is subject to modification according to necessity.

DETAILED DESCRIPTION

Hereinafter, a preferred embodiment of the present invention will be described. The embodiment provided in the following is provided for the purpose of better understanding of the present invention, and it should be understood that the scope of the present invention is not intended to be limited to the following description. Therefore, it is obvious that a person ordinarily skilled in the art can make reference to the descriptions in the present specification, and to appropriately modify the invention within the scope of the present invention.

(Sugar Chain Analysis Method)

According to one aspect, the present invention provides a method for analyzing a sugar chain in a sample. This method includes A) a sugar chain releasing step of releasing a sugar chain in a sample; B) a detection sample preparing step of preparing the released sugar chain for use in detection; when performing mass spectrometry using a plate, the following step C) a step of producing a plate for mass spectrometry having the captured sugar chain sample dotted thereon; and a step of performing an analysis of the sugar chain to be determined.

In the A) sugar chain releasing step of releasing a sugar chain in a sample, the following processes may be carried out.

A sugar chain releasing step, comprising
- A-1) a step of providing the sample on a plate for reaction;
- A-2) a step of adding a solubilizing agent to the sample to thereby place the sample under a reaction condition;
- A-3) a step of adding a reducing agent to the sample to thereby place the sample under a reaction condition;
- A-4) a step of adding an —SH protecting agent to the sample to thereby place the sample under a reaction condition;
- A-5) a step of adding a proteolytic enzyme to the sample to thereby place the sample under a reaction condition;
- A-6) a step of deactivating the proteolytic enzyme; and
- A-7) a step of adding a sugar chain releasing enzyme to the sample to thereby release the sugar chain.

In sub-processes of the step (A), it is preferable to use the conditions shown below, but the invention is not intended to be limited thereto. For the following conditions, any one may be employed, or a plurality of them may be employed.

A-1) The step of providing the sample on a plate for reaction may be manually carried out, or may be automated. Representative examples of the sample include a body fluid, a cell extract and a tissue extract, and a more representative example is blood serum. Typically, the sample is provided on a filter plate.

In regard to A-2), the solubilizing agent is 1-propanesulfonic acid, 2-hydroxy-3-lauramide (PHL), 1-propanesulfonic acid, 2-hydroxy-3-myristamide (PHM), 2-hydroxy-3-sulfopropyl laurate (HSD), or an equivalent thereto, and these can be represented by the formula: R—OCOO—CH$_2$CH(OH)CH$_2$—SO$_2$—ONa (wherein, R represents an alkyl group). For example, it is preferable to use 1-propanesulfonic acid, 2-hydroxy-3-lauramide (PHL), or 1-propanesulfonic acid, 2-hydroxy-3-myristamide (PHM)/ammonium bicarbonate. As such a solubilizing agent, those listed in WO 2008/001888 (PCT/JP2007/063100) can be used.

The reaction conditions described above are typically 25° C. to 42° C., and preferably 37° C., and the reaction time is typically 5 to 60 minutes, and preferably about 10 minutes.

A-3) The reducing agent is dithiothreitol (DTT), TCEP (Tris(2-carboxyethyl)phosphine hydrochloride solution 0.5 M), or an equivalent, the reaction condition is usually room temperature to 80° C., preferably 50° C. to 80° C., and typically 60° C., and the reaction time is typically 30 minutes to 2 hours, and preferably about one hour.

A-4) The —SH protective agent is iodoacetamide (IAA) or an equivalent, and the reaction condition is 20 to 37° C. (typically, room temperature) in the dark. The reaction time is typically 0.5 to 2 hours, and for example, one hour.

A-5) The proteolytic enzyme is typically trypsin, chymotrypsin, or an equivalent, and preferably trypsin, and the reaction condition is 25 to 42° C., and typically 37° C. The reaction time is typically 30 to 120 minutes, and for example, about 60 minutes.

A-6) The conditions for the deactivation include heating to typically 65° C. or higher, and preferably 80 to 100° C. (for example, 90° C.). Here, the heating time is typically 1 to 10 minutes (for example, 5 minutes), and the system is optionally cooled to room temperature.

A-7) The sugar chain releasing enzyme is peptide-N-glycosidase F, peptide-N4-(acetyl-β-glucosaminyl)-asparagine amidase (PNGaseF), Endo H, or an equivalent, and it is preferable not to have evaporation of the solvent during the step. A countermeasure can be taken by a heating treatment at the ceiling.

The reaction conditions for the sugar chain releasing enzyme are 25° C. to 42° C. (for example, 37° C.), and the reaction time is typically 2 to 24 hours, and for example, 12 hours.

In the B) detection sample preparing step of preparing the released sugar chain for use in detection, the following processes may be carried out:
- B-1) a step of contacting the sample prepared in the step (A) with a sugar chain-capturing bead to thereby place the sample under the conditions allowing the released sugar chain in the sample to bind to the bead, and thus producing a captured sugar chain sample;
- B-2) a step of adding a protein denaturing agent to the captured sugar chain sample to thereby place the captured sugar chain sample under a reaction condition;
- B-3) a step of washing the captured sugar chain sample, and then discarding the residual washing liquid by suction;
- B-4) a step of adding a salt releasing agent for the sugar chain capturing agent on beads to the captured sugar chain sample, and then discarding the salt releasing agent by suction;
- B-5) a step of adding a protective agent to the captured sugar chain sample to thereby place the captured sugar chain under a reaction condition;
- B-6) a step of adding an acid to the captured sugar chain sample, and discarding the acid by suction;
- B-7) a step of adding an organic reaction solvent to the captured sugar chain sample;
- B-8) a step of removing the solvent and the moisture in the bead;
- B-9) a step of adding an alkyl esterifying agent to the captured sugar chain sample to thereby place the captured sugar chain sample under a reaction condition, and alkylating the carboxylic acid of sialic acid;
- B-10) a step of adding the organic reaction solvent to the captured sugar chain sample, and discarding the organic reaction solvent by suction;
- B-11) a step of washing the captured sugar chain sample, and subsequently discarding the residual washing liquid by suction;
- B-12) a step of releasing a sugar chain sample from the captured sugar chain sample, wherein when an analysis requiring tagging is conducted, the sugar chain in the captured sugar chain sample is tagged with a labeling reagent and is released from the bead; and B-13) a step of dissolving the released sugar chain sample to produce a sugar chain sample solution.

In the sub-processes in the step (B), it is preferable to use processes characterized by one or a plurality of the conditions as shown below, but the invention is not intended to be limited thereto.

In regard to B-1), the bead is a bead or magnetic bead having a sugar chain-capturing group containing an aminooxy group, an N-alkylaminooxy group, a hydrazide group, an azide group, a thiosemicarbazide group, a cysteine residue, or a derivative thereof, and the conditions in which the sugar chain in the sample binds to the bead are typically 25 to 80° C., and more typically 40 to 80° C., and for example, 80° C. is used.

B-2) The denaturing agent is guanidine hydrochloride, urea, sodium dodecyl sulfate or an equivalent, and the reaction conditions involve adding at room temperature, and maintaining the temperature to allow the bead to sufficiently swell (from 10 seconds to 5 minutes).

B-3) The washing is performed using water, and then the water is discarded by suction.

B-4) The sugar chain capturing agent on the bead is an aminooxy group, an N-alkylaminooxy group, a hydrazide group, an azide group, a thiosemicarbazide group, a cysteine residue or a derivative thereof, and the salt releasing agent is triethylamine or an equivalent thereto in the case of hydrazide, and is triethylamine in the case of an N-alkylaminooxy group. Thereafter, the triethylamine is optionally discarded by suction.

B-5) The protective agent is acetic anhydride, succinic anhydride, another acid anhydride or an equivalent, and the reaction conditions include (for example, 10%) acetic anhydride/methanol at 15 to 37° C. (for example, room temperature) for 10 minutes to 2 hours (for example, 30 minutes). Thereafter, the acetic anhydride is optionally discarded by suction.

B-6) The acid is hydrochloric acid, another inorganic salt acid, or an equivalent acid at pH 2 to 3, and the acid is optionally discarded by suction.

B-7) Prior to the purging with the organic reaction solvent, a step of purging with a hydrophilic organic solvent is included. This hydrophilic organic solvent is typically a lower alcohol such as methanol or ethanol, acetonitrile or acetone, and the organic reaction solvent is dioxane, acetonitrile, tetrahydrofuran or an equivalent. The methanol or the like is optionally discarded by suction, and then dioxane is added to the captured sugar chain sample.

B-8) The step of removing the solvent and moisture in the bead typically includes wiping the bottom with a cotton sheet, a paper, a blotting paper, gauze, a towel, a hand towel, a tissue paper or the like.

B-9) The alkyl esterifying agent is typically methyl-p-tolyl-triazene (MTT), ethyl-p-tolyltriazene (ETT), butyl-p-tolyl-triazene (BTT), or an equivalent, and methyl-p-tolyl-triazene (MTT) is preferred.

The reaction conditions include 100 mM MTT/dioxane at 60 to 80° C. for 30 to 120 minutes (for example, 60 minutes).

B-10) The organic reaction solvent is typically dioxane, acetonitrile, tetrahydrofuran or an equivalent, and dioxane is preferred. The dioxane or the like is optionally discarded by suction.

B-11) The washing is performed using at least one selected from the group consisting of methanol, a NaCl solution and water, and thereafter, the methanol, NaCl solution and water are optionally discarded by suction. An amount sufficient for washing may be used, and for example, an amount of 100 µl to 1 ml, for example, 200 µl, may be used but is not limited thereto. The NaCl solution can be used at any concentration, but for example, a solution at 10 to 100 mM may be used, and a solution at 20 mM for example, may be used.

B-12) Tagging is carried out. Typically, the tagging is carried out using a chromophore capable of absorbing ultraviolet and visible rays, a tag having a structure emitting fluorescence, an affinity tag having a molecule capable of interacting with another molecule (His tag, biotin, or the like), a tag having a functional group capable of specifically reacting with a functional group (a photoreactive molecule (for crosslinking), an azide group, an SH group, an amino group, carboxylic acid, or the like), a tag having a functional group in a hydrophobic structure, or a tag having a metal ion ligand, and the tagging is conducted by adding acetic acid, acetonitrile, an acetate buffer solution or an equivalent. It is preferable to subject the sample to MALDI-TOF MS. Even for mass spectrometry, another ionization method can be used. For example, multi-stage mass spectrometry such as MS/MS can be carried out by ESI-MS (electrospray ionization mass spectrometry), and the respective mass spectrometric methods (LC-MS/MS, or the like). In addition to that, recovering the sugar chain using a fluorescent dye tag and performing LC-ESI-MS (/MS) is contemplated. For example, acetic acid and acetonitrile are added to the captured sugar chain sample, and the sugar chain in the captured sugar chain sample can be tagged using aminooxytryptophanyl-arginine methyl ester/water, O-benzylhydroxylamine hydrochloride/water, or anthraniloyl hydrazine/water. The sugar chain can also be recovered using a biotin tag and be subjected to an interaction analysis based on SPR such as BIACORE, or to the production of a microarray plate. When the sugar chain is recovered using a fluorescent dye tag, it is not that MALDI-TOF analysis cannot be performed, and the analysis can be carried out by selecting appropriate conditions.

B-13) The dissolution of the tagged captured sugar chain sample is typically carried out using water, an aqueous solution or an equivalent.

When performing mass spectrometry using a plate, the following process C can be carried out, and C) the step of producing a plate for mass spectrometry having the captured sugar chain sample dotted thereon, can have at least one feature among those described below:

C-1) a step of disposing the tagged sugar chain sample solution obtained in the step (B) on a plate for recovery; and, the step optionally comprises the steps (C-2) to (C-6):

C-2) a step of disposing the tagged sugar chain sample solution from the plate for recovery and the organic solvent, on a plate for mixing so as to obtain a concentration at which the sugar chain adsorbs to a solid phase;

C-3) a step of providing a solid phase carrier-enclosed plate;

C-4) a step of activating the solid phase carrier-enclosed plate according to the phase of the solid phase carrier-enclosed plate, and washing the solid phase carrier-enclosed plate;

C-5) a step of adding the tagged sugar chain sample solution to the solid phase carrier-enclosed plate, and conditioning the tagged sugar chain sample solution to a solvent having a polarity appropriate for the phase of the solid phase carrier-enclosed plate;

C-6) a step of recovering the tagged sugar chain sample solution by suction from the solid phase carrier-enclosed plate to a second plate for recovery; and when subjecting the tagged sugar chain sample solution to MALDI-TOF MS, the following step (C-7) is carried out:

C-7) a step of dotting the tagged sugar chain sample solution on a matrix for mass spectrometry.

In the sup-processes for the step (C), it is preferable to use processes characterized by one or a plurality of conditions as shown below, but the invention is not intended to be limited thereto.

C-1) The disposing on the plate for recovery is conducted under the conditions of removing the reagent for tagging.

C-2) The concentration at which the sugar chain adsorbs to the solid phase is typically 80 to 90% in an organic solvent, and preferably, the tagged sugar chain sample solution from the plate for recovery and acetonitrile are disposed on a plate for mixing, so as to obtain a final concentration of acetonitrile of 80 to 90%.

C-3) The solid phase carrier-enclosed plate is typically of multi-well type and includes a surface of a resin or membrane suitable for solid phase extraction.

C-4) When the solid phase carrier-enclosed plate is in normal phase mode, washing is conducted sequentially with water and acetonitrile, and when the solid phase carrier-enclosed plate is in reverse phase mode, washing is conducted sequentially with a lower alcohol such as methanol and water.

C-5) The solvent having an opposite polarity is a hydrophobic organic solvent in the case of the normal phase mode, and is a hydrophilic solvent in the case of the reverse phase mode. Here, for example, the tagged sugar chain sample solution is added to the solid phase carrier-enclosed plate, the liquid is discarded, and typically, the plate is washed with acetonitrile. Furthermore 1 to 20% (for example, 5%) acetonitrile can be added thereto.

C-6) The second plate for recovery is of multi-well type and includes a surface of a resin or membrane suitable for solid phase extraction.

C-7) the matrix for mass spectrometry is typically 2,5-dihydroxybenzoic acid or an equivalent, and the dotting of the tagged sugar chain sample solution on the matrix for mass spectrometry is conducted in mixture or in sequence, and is diluted as necessary. Furthermore, preferably, 2,5-dihydroxybenzoic acid in 20 to 40% (for example, 30%) acetonitrile can be added to the tagged sugar chain sample solution, and the mixture can be dotted.

In the D) step of conducting an analysis of the sugar chain to be determined, any mass spectrometric method, typically MADLI-TOF can be used. Upon conducting MALDI-TOF in the step (D), it is preferable to carry out the overall step (C). The mass spectrometry of the sugar chain to be determined is carried out by high performance liquid chromatography (HPLC), liquid chromatography-electrospray ionization mass spectrometry (LC-ESI MS), Matrix Assisted laser Desorption Ionization-Time-of-Flight (MALDI-TOF), or an equivalent. When using a coloring reagent or biotin in the tagging, it is preferable to carry out a step of removing any excess coloring reagent. When the bead are magnetic beads, the magnetic beads are preferably beads having a modifiable functional group (for example, a carboxyl group, an amino group, an epoxy group, a tosyl group, or streptavidin-bound magnetic beads).

If there is no problem in the subsequent analysis such as MALDI-TOF MS while the sample has been recovered to the plate for recovery 1, the process using the SPE plate can be omitted. When MALDI-TOF MS is carried out under that situation, the sample is transferred from the plate for recovery 1 to an MP2 plate for mixing and is mixed with the matrix, and then the mixture is dotted on the MALDI plate. When using the sample directly with HPLC, LC-ESI MS or the like, the step can be omitted.

When using a coloring reagent, if it is necessary to remove any excess coloring reagent, it is preferable to carry out reverse phase or normal phase extraction, or solid phase extraction such as ion exchange. Therefore, although the type of the SPE plate and the solvent for activation and washing depend on the properties of the reagent, it is preferable to carry out a similar procedure. If the excess reagent does not cause any problem (for example, if the reagent emits fluorescence for the first time by binding to the sugar chain), the sample can be subjected to analysis while being retained in an autosampler as received. In the case of biotin tag as well, it is preferable to remove any free (not bound to the sugar chain) reagent. It is preferable to implement the SPE plate operation.

The respective features of the above preferred embodiment are such that one may be included, or two or more may be combined.

(Sugar Chain Releasing Method for Releasing Sugar Chain in Sample)

The present invention provides a sugar chain releasing method for releasing a sugar chain in a sample. This method comprises the following steps:

A-1) a step of providing the sample on a plate for reaction;

A-2) a step of adding a solubilizing agent to the sample to thereby place the sample under a reaction condition;

A-3) a step of adding a reducing agent to the sample to thereby place the sample under a reaction condition;

A-4) a step of adding an —SH protecting agent to the sample to thereby place the sample under a reaction condition;

A-5) a step of adding a proteolytic enzyme to the sample to thereby place the sample under a reaction condition;

A-6) a step of deactivating the proteolytic enzyme; and

A-7) a step of adding a sugar chain releasing enzyme to the sample to thereby release the sugar chain.

According to a preferred embodiment, a method further having at least any one of the following features for the above-described steps is provided:

A) in the sugar chain releasing step of releasing a sugar chain in a sample to prepare a sugar chain sample for analysis:
  A-1) the sample is a body fluid, a cell extract or a tissue extract;
  A-2) the solubilizing agent is 1-propanesulfonic acid, 2-hydroxy-3-lauramide (PHL), 1-propanesulfonic acid, 2-hydroxy-3-myristamide (PHM), 2-hydroxy-3-sulfopropyl laurate (HSD) or an equivalent thereto, or the reaction condition is at 25° C. to 42° C.;
  A-3) the reducing agent is dithiothreitol (DTT), TCEP (Tris(2-carboxyethyl)phosphine hydrochloride solution, 0.5 M), or an equivalent thereto, or the reaction condition is at room temperature to 80° C.;
  A-4) the —SH protecting agent is iodoacetamide (IAA) or an equivalent thereto, or the reaction condition is at 20 to 37° C. in the dark;
  A-5) the proteolytic enzyme is trypsin, chymotrypsin or an equivalent thereto, or the reaction condition is at 25 to 42° C.;
  A-6) the conditions for deactivating include heating to 65° C. or higher;
  A-7) the sugar chain releasing enzyme is peptide-N-glycosidase F, peptide-N4-(acetyl-β-glucosaminyl)-asparagine amidase (PNGaseF), Endo H or an equivalent thereto, or the reaction conditions for the sugar chain releasing enzyme are at 25° C. to 42° C.

According to a more preferred embodiment, a method further having at least one among the following steps is provided:

A-1) a step of providing blood serum as a sample on a filter plate;

A-2) a step of adding 1-propanesulfonic acid, 2-hydroxy-3-lauramide (PHL) or 1-propanesulfonic acid, 2-hydroxy-3-myristamide (PHM)/ammonium bicarbonate, and allowing the mixture to react for 5 to 60 minutes at 25 to 42° C.;

A-3) a step of adding dithiothreitol (DTT) to the sample, allowing the mixture to react for 10 to 60 minutes at 50 to 80° C., and then cooling the reaction mixture to room temperature;

A-4) a step of adding iodoacetamide (IAA), and allowing the mixture to react for 0.5 to 2 hours at room temperature in the dark;

A-5) a step of adding trypsin to the sample, and allowing the mixture to react for 30 to 120 minutes at 25 to 42° C.;

A-6) a step of heating the sample to 80 to 100° C. for 1 to 10 minutes, and then cooling the sample to room temperature; and A-7) a step of adding PNGaseF, and allowing the mixture to react for 6 to 24 hours at 25 to 42° C.

According to a certain embodiment, the method is used for the preparation of a pretreatment sample for analyzing a sugar chain in a sample.

In the above preferred embodiments, the respective features may be included singly or in combination or two or more.

(Detection Sample Preparing Method for Preparing Released Sugar Chain for Use in Detection)

The present invention also provides a detection sample preparing method for preparing the released sugar chain for use in detection. This method includes the following steps:

B-1) a step of contacting a sample with a sugar chain-capturing bead to thereby place the sample under the conditions allowing the released sugar chain in the sample to bind to the bead, and thus producing a captured sugar chain sample;

B-2) a step of adding a protein denaturing agent to the captured sugar chain sample to thereby place the captured sugar chain sample under a reaction condition;

B-3) a step of washing the captured sugar chain sample, and then discarding the residual washing liquid by suction;

B-4) a step of adding a salt releasing agent for the sugar chain capturing agent on beads to the captured sugar chain sample, and then discarding the salt releasing agent by suction;

B-5) a step of adding a protective agent to the captured sugar chain sample to thereby place the captured sugar chain under a reaction condition;

B-6) a step of adding an acid to the captured sugar chain sample, and discarding the acid by suction;

B-7) a step of adding an organic reaction solvent to the captured sugar chain sample;

B-8) a step of removing the solvent and the moisture in the bead;

B-9) a step of adding an alkyl esterifying agent to the captured sugar chain sample to thereby place the captured sugar chain sample under a reaction condition, and alkylating the carboxylic acid of sialic acid;

B-10) a step of adding the organic reaction solvent to the captured sugar chain sample, and discarding the organic reaction solvent by suction;

B-11) a step of washing the captured sugar chain sample, and subsequently discarding the residual washing liquid by suction;

B-12) a step of releasing a sugar chain sample from the captured sugar chain sample, wherein when an analysis requiring tagging is conducted, the sugar chain in the captured sugar chain sample is tagged with a labeling reagent and is released from the bead; and B-13) a step of dissolving the released sugar chain sample to produce a sugar chain sample solution.

According to a preferred embodiment, a method further having at least any one of the following features for the above-described steps is provided:

In regard to B-1), the bead is a bead or magnetic bead having bound thereto a sugar chain capturing group which includes an aminooxy group, an N-alkylaminooxy group, a hydrazide group, an azide group, a thiosemicarbazide group, a cysteine residue or a derivative thereof, or the conditions in which the released sugar chain in the sample binds to the bead are at 25 to 80° C.;

B-2) the denaturing agent is guanidine hydrochloride, urea, sodium dodecyl sulfate or an equivalent, or the reaction conditions involve adding at room temperature, and maintaining the temperature to allow the bead to sufficiently swell (from 10 seconds to 5 minutes);

B-3) the washing is performed using water;

B-4) the sugar chain capturing agent on the bead is an aminooxy group, an N-alkylaminooxy group, a hydrazide group, an azide group, a thiosemicarbazide group, a cysteine residue or a derivative thereof, and the salt releasing agent is triethylamine or an equivalent in the case of hydrazide, and is triethylamine or an equivalent in the case of an N-alkylaminooxy group;

B-5) the protective agent is acetic anhydride, succinic anhydride or another acid anhydride, or an equivalent, or the reaction conditions use acetic anhydride/methanol at 15 to 37° C.;

B-6) the acid is hydrochloric acid or another inorganic salt acid, or an equivalent acid at pH 2 to 3;

B-7) the step includes a step of replacing with a hydrophilic organic solvent before replacing with the organic reaction solvent, and the hydrophilic organic solvent is a lower alcohol such as methanol or ethanol, acetonitrile, or acetone, while the organic reaction solvent is dioxane, acetonitrile, tetrahydrofuran or an equivalent;

B-8) the step of removing the solvent and the moisture in the bead includes wiping of the bottom with a filter paper, a blotting paper, a gauze, a towel, a hand towel, a tissue paper or a cotton sheet;

B-9) the alkyl esterifying agent is methyl-p-tolyltriazene (MTT), ethyl-p-tolyltriazene (ETT), butyl-p-tolyltriazene (BTT) or an equivalent thereto, or the reaction conditions use 100 mM MTT/dioxane at 20 to 80° C. for 30 minutes to 5 hours;

B-10) the organic reaction solvent is dioxane, acetonitrile, tetrahydrofuran or an equivalent thereto;

B-11) the washing is performed using at least one selected from the group consisting of methanol, a NaCl solution and water;

B-12) tagging is carried out, such that the tagging is performed using a chromophore capable of absorbing ultraviolet and visible rays, a tag having a structure emitting fluorescence, an affinity tag having a molecule capable of interacting with another molecule, a tag having a functional group capable of specifically reacting with a functional group, a tag having a functional group in a hydrophobic structure, or a tag having a metal ion ligand, and the tagging is conducted by adding acetic acid, acetonitrile, an acetate buffer or an equivalent; or B-13) the dissolving of the tagged captured sugar chain sample is performed using water, an aqueous solution or an equivalent.

According to a more preferred embodiment, a method further having at least one among the following steps is provided:

B-1) a step of contacting a captured sugar chain sample with beads for capturing sugar chain, to thereby allow binding at 40 to 80° C., and thus producing a captured sugar chain sample;

B-2) a step of adding guanidine hydrochloride to the captured sugar chain sample to thereby place the captured sugar chain sample under a reaction condition, and then discarding the reaction liquid by suction;

B-3) a step of washing the captured sugar chain sample with water, and then discarding the water by suction;

B-4) a step of washing the captured sugar chain sample with triethylamine, and then discarding the triethylamine by suction;

B-5) a step of adding acetic anhydride to the captured sugar chain sample to thereby place the captured sugar chain sample under the reaction conditions of using 10% acetic anhydride/methanol at room temperature for 10 minutes to 2 hours, and then discarding the acetic anhydride by suction;

B-6) a step of adding hydrochloric acid to the captured sugar chain sample, and discarding the hydrochloric acid by suction;

B-7) a step of adding methanol to the captured sugar chain sample, discarding the methanol by suction, and then adding dioxane to the captured sugar chain sample;

B-8) a step of wiping the bottom with a cotton sheet;

B-9) a step of adding methyl-p-tolyltriazene (MTT) to the captured sugar chain sample, and allowing the mixture to react for 30 to 120 (60) minutes at 60° C.;

B-10) a step of adding dioxane to the captured sugar chain sample, and discarding the dioxane by suction;

B-11) a step of washing the captured sugar chain sample sequentially with methanol, a NaCl solution and water, and then discarding the water by suction;

B-12) a step of adding acetic acid and acetonitrile to the captured sugar chain sample, and tagging the sugar chain in the captured sugar chain sample using aminooxytryptophanyl-arginine methyl ester/water, O-benzylhydroxylamine hydrochloride/water, or anthraniloyl hydrazine/water; and B-13) a step of adding water to the tagged captured sugar chain sample to produce a tagged sugar chain sample solution.

According to another preferred embodiment, the sugar chain-capturing bead are magnetic beads, and separation is carried out using a magnetic field instead of discarding by suction as described above.

According to a certain embodiment, the method is used for the preparation of a pretreatment sample for analyzing a sugar chain in a sample.

In the above preferred embodiments, the respective features may be included singly or in combination or two or more.

(Method for Producing Plate for Mass Spectrometry Having Captured Sugar Chain Sample Dotted Thereon, for Mass Spectrometry Using Plate)

According to another aspect, the present invention provides a method for producing a plate for mass spectrometry having the captured sugar chain sample dotted thereon, for mass spectrometry using a plate. This method comprises the following step(s):

C-1) a step of disposing a tagged sugar chain sample solution on a plate for recovery; and, optionally comprises the steps (C-2) to (C-6):

C-2) a step of disposing the tagged sugar chain sample solution from the plate for recovery and the organic solvent, on a plate for mixing so as to obtain a concentration in the organic solvent at which the sugar chain adsorbs to a solid phase;

C-3) a step of providing a solid phase carrier-enclosed plate;

C-4) a step of activating the solid phase carrier-enclosed plate according to the phase of the solid phase carrier-enclosed plate, and washing the solid phase carrier-enclosed plate;

C-5) a step of adding the tagged sugar chain sample solution to the solid phase carrier-enclosed plate, and conditioning the tagged sugar chain sample solution to a solvent having a polarity appropriate for the phase of the solid phase carrier-enclosed plate;

C-6) a step of recovering the tagged sugar chain sample solution by suction from the solid phase carrier-enclosed plate to a second plate for recovery; and when subjecting the tagged sugar chain sample solution to MALDI-TOF MS, the method includes the following step (C-7):

C-7) a step of mixing the tagged sugar chain sample solution with a matrix for mass spectrometry, and dotting the mixture on a plate for determination.

According to a preferred embodiment, a method further having at least any one of the following features for the above-described steps is provided:

C-1) the disposing on the plate for recovery is conducted under the conditions of removing the reagent for tagging;

C-2) the concentration at which the sugar chain adsorbs to the solid phase is 80 to 90% in an organic solvent;

C-3) the solid phase carrier-enclosed plate is of multi-well type and includes a surface of a resin or membrane suitable for solid phase extraction;

C-4) when the solid phase carrier-enclosed plate is in normal phase mode, washing is conducted sequentially with water and acetonitrile, and when the solid phase carrier-enclosed plate is in reverse phase mode, washing is conducted sequentially with a lower alcohol such as methanol and water;

C-5) the solvent having an opposite polarity is a hydrophobic organic solvent in the case of the normal phase mode, and is a hydrophilic solvent in the case of the reverse phase mode;

C-6) the second plate for recovery is of multi-well type and includes a surface of a resin or membrane suitable for solid phase extraction; and C-7) the matrix for mass spectrometry is 2,5-dihydroxybenzoic acid or an equivalent, and the dotting of the tagged sugar chain sample solution on the matrix for mass spectrometry is conducted in mixture or in sequence, and is diluted as necessary.

According to a more preferred embodiment, a method for producing a plate for mass spectrometry, further having at least one among the following steps, is provided:

C-1) a step of disposing a tagged sugar chain sample solution on a plate for recovery;

C-2) a step of disposing the tagged sugar chain sample solution from the plate for recovery and acetonitrile on a plate for mixing, so as to achieve a final concentration of acetonitrile of 80 to 90%;

C-3) a step of providing a solid phase carrier-enclosed plate which is in normal phase mode;

C-4) a step of washing the solid phase carrier-enclosed plate sequentially with water and acetonitrile, and discarding water and acetonitrile by suction;

C-5) a step of adding the tagged sugar chain sample solution to the solid phase carrier-enclosed plate, discarding the liquid, washing the plate with acetonitrile, and adding 1 to 20% acetonitrile thereto;

C-6) a step of recovering the bead by suction from the solid phase carrier-enclosed plate to the second plate for recovery; and C-7) a step of adding 2,5-dihydroxybenzoic acid in 20 to 40% acetonitrile, to the tagged sugar chain sample solution, and mixing and dotting the mixture.

According to another preferred embodiment, the sugar chain-capturing bead are magnetic beads, and separation is carried out using a magnetic field instead of discarding by suction as described above.

According to a certain embodiment, the method is used for the preparation of a pretreatment sample for analyzing a sugar chain in a sample.

In the above preferred embodiments, the respective features may be included singly or in combination or two or more.

(Kit for Production of Plate for Reaction Comprising Sample-Derived Sugar Chain and a Sugar Chain-Capturing Bead)

The present invention provides a kit for production of a plate for reaction comprising a sample-derived sugar chain and a sugar chain-capturing bead, which kit is provided with a means for realizing any of the operations of the method of the present invention for analyzing a sugar chain in a sample. An example of such a kit, includes a kit comprising the following:

A-1) the sample;
A-2) 1-propanesulfonic acid, 2-hydroxy-3-lauramide (PHL) or 1-propanesulfonic acid, 2-hydroxy-3-myristamide (PHM)/ammonium bicarbonate;
A-3) dithiothreitol (DTT);
A-4) iodoacetamide (IAA);
A-5) trypsin;
A-6) a heating unit;
A-7) PNGaseF;
B-1) a sugar chain-capturing bead;
B-2) guanidine hydrochloride;
B-3) water;
B-4) triethylamine;
B-5) 10% acetic anhydride/methanol;
B-6) hydrochloric acid;
B-7) methanol;
B-8) cotton sheet;
B-9) methyl-p-tolyltriazene (MTT);
B-10) dioxane;
B-11) methanol, a NaCl solution and water;
B-12) acetic acid and acetonitrile, and aminooxytryptophanyl-arginine methyl ester/water, O-benzylhydroxylamine hydrochloride/water or anthraniloyl hydrazine/water;
B-13) water;
C-1) a plate for recovery;
C-2) acetonitrile and a plate for mixing;
C-3) a solid phase carrier-enclosed plate;
C-4) water and acetonitrile;
C-5) acetonitrile and 1 to 20% acetonitrile;
C-6) a second plate for recovery; and
C-7) 2,5-dihydroxybenzoic acid in 20 to 40% acetonitrile.

In regard to the respective features shown above, the respective features for the above preferred embodiments described in the present specification may be included singly, or two or more of the features may be combined.

(Plate for Analysis Comprising Sample-Derived Sugar Chain and a Sugar Chain-Capturing Bead)

The present invention also provides a plate produced in connection with the method for analyzing a sugar chain in a sample of the present invention. Such a plate can also be said to be a plate for analysis comprising a sample-derived sugar chain and a sugar chain-capturing bead, in which the sugar chain-capturing bead bound with the sugar chain released from the sample are dotted on at least one hole of the plate, and the sugar chain has been tagged using a tagging reagent such as aminooxytryptophanyl-arginine methyl ester/water, O-benzylhydroxylamine hydrochloride/water or anthraniloyl hydrazine/water.

In regard to the respective features shown above, the respective features for the above preferred embodiments described in the present specification may be included singly, or two or more of the features may be combined.

(Plate for Analyzing Sugar Chain in Sample)

The present invention also provides a plate for analyzing a sugar chain in a sample, the plate having at least one compartment for analysis, and at least one of the compartment having a sugar chain-capturing bead previously dispensed therein. As the plate, for example, a multi-well plate such as a 96-well plate, or a filter plate is used. In regard to 121 (BlotGlyco H) in FIG. 1 and Start2 (BlotGlyco ABC) in FIG. 8, instead of manually dispensing a sugar chain-capturing bead by hand, a plate having such a sugar chain-capturing bead previously dispensed, can be used. Analysis can be carried out more conveniently with such a plate, by combining the plate with an auto-analyzing apparatus for sugar chain.

In regard to the respective features shown above, the respective features for the above preferred embodiments described in the present specification may be included singly, or two or more of the features may be combined.

(Exemplary Specific Embodiment of Automatic Sugar Chain Pretreatment Apparatus)

Hereinafter, the best embodiment for implementing the automatic sugar chain pretreatment apparatus according to the present invention will be described with reference to the drawings.

FIG. 15 is a plane view showing the automatic sugar chain pretreatment apparatus according to an embodiment of the present invention, with some parts being omitted from the diagram; FIG. 16 is a frontal view of the dispensing head; FIG. 17 is a cross-sectional view of FIG. 2, dissected along the line A-A; FIG. 18 is a central vertical cross-sectional view of the first constant-temperature bath; FIG. 19 is an exploded perspective view showing the first low-pressure recovering device and the filter plate moving mechanism; FIG. 20 is a plane view showing the filter plate moving mechanism, with some parts being omitted from the diagram; FIG. 21 is a vertical cross-sectional view showing the vertical moving unit in the filter plate moving mechanism, with some parts being omitted from the diagram; FIG. 22 is a perspective view of the filter plate moving mechanism and the second constant-temperature bath; FIG. 23 is a central vertical cross-sectional view of the second constant-temperature bath; FIG. 24 and FIG. 25 are flow diagrams of the treatment operation.

The present invention allows the sugar chain purification treatment to be carried out at high speed with high accuracy by automating the treatment, and provides, inside a casing base 1, a dispensing head 2 to move in longitudinal and transverse directions by means of a moving mechanism 11. Dispensing needles 10, 10, 10, . . . are retained in the dispensing head 2 so as to move up and down. A first and second constant-temperature baths 12 and 29 are provided, which are equipped with a means to conduct heating and cooling of a receiving stand, with the upper part of the receiving stand being covered with a lid. A reagent rack 22, and microplates for mixing 23 and 24 are provided. In front of the second constant-temperature bath 29, a first low-pressure recovering device 26, a first suction discarding device 27, and a bottom wiper 28 are disposed in a row. In front of a target plate receiving stand 59, a second low-pressure recovering device 56 and a second suction discarding device 57 are disposed. The operation process inputted into the control device 60 disposed in the casing base 1, operates the respective units mentioned above.

The automatic sugar chain pretreatment apparatus according to the present embodiment is equipped with a casing base 1 provided with a cover capable of freely opening and closing (not depicted); a dispensing head moving mechanism 11 that is installed inside the casing base 1 and moves a below-described dispensing head in longitudinal and transverse directions; a dispensing head 2 that raises and lowers a plurality of dispensing needles arranged in a row, all at the same time by means of an elevating mechanism; a first constant-temperature bath 12 installed above the installation space 1a for the casing base 1, which is equipped with a unit that conducts heating and cooling of a receiving stand 13 that holds a microplate, and is provided with a lid 21 having an inner lid 19 to cover the upper part of the receiving stand 13; a reagent rack 22 and a plurality of microplates for mixing 23 and 24, which are installed above the installation space for the casing base 1; a first low-pressure recovering device 26, being in a frame form, which depressurizes while having a filter plate mounted on the upper opening, and receives the liquid that has passed through the filter of the filter plate, into a microplate 25 installed inside the recovering device; a first suction discarding device 27, being in a frame form, which depressurizes and suctions while having a filter plate mounted on the upper opening, and discards the liquid that has passed through the filter; a second constant-temperature bath 29, which is equipped with a unit that conducts heating and cooling of a receiving stand 30 that holds a filter plate, and is provided with an automatically opening and closing lid 38 to cover the upper part of the receiving stand 30, all of these devices being disposed and arranged in a row along the longitudinal direction and above the installation space 1a for the casing base 1; a filter plate moving mechanism 39 that retains a filter plate and moves the filter plate to each of the first low-pressure recovering device 26, the first suction discarding device 27 and the second constant-temperature bath 29 in sequence; a second low-pressure recovering device 56, being in a frame form, which depressurizes while having an SPE plate mounted on the upper opening, and receives the liquid that has passed through the solid phase body of the SPE plate, into a microplate 55 installed inside the recovering device; a second suction discarding device 57, being in a frame form, which depressurizes and suctions while having an SPE plate mounted on the upper opening, and discards the liquid that has passed through the solid phase body; a target plate receiving stand 59, which holds a target plate 58 that is dotted on the surface with the sample that has been finished with the final treatment step, all of these devices 56, 57 and 59 being disposed and arranged in a row along the longitudinal direction and above the installation space 1a for the casing base 1; an SPE plate moving mechanism 39 that retains an SPE plate and moves the SPE plate between the second low-pressure recovering device and the second suction discarding device; a control device 60 that is installed in the casing base 1 and has been inputted with the operation protocol; a microplate 61 having a plurality of wells arranged in a matrix array, which is covered with a sheet while biological samples have been injected into each well; a filter plate 62 having a plurality of filters arranged in a matrix array; and an SPE plate (not depicted) for sample in a trace amount, having a plurality of solid phase bodies arranged in a matrix array, wherein the apparatus is made to operate each of the devices according to the operation protocol inputted to the control device 60.

Furthermore, in regard to the above constitution, a bottom wiper 28 which is provided with a planar wiping material on the surface, and is intended to wipe out the liquid adhering to the lower surface of the bottom of the filter plate, may be installed between the first suction discarding device 27 and the second constant-temperature bath 29, as necessary.

Furthermore, the dispensing head moving mechanism 11 in the constitution described above may employ a well known moving mechanism making use of a motor or a rail.

The dispensing head 2 is a dispensing head constituted to have a supporting frame 3; an elevator stand 5 that slides in the vertical direction along a guide rod installed on the supporting frame 3 in parallel with the dispensing needles; a driving motor 6 fixed on the supporting frame 3; an elevator stand moving mechanism 8 that has a ball screw 7 connected to the rotating axis of the driving motor 6 and moves the elevator stand 5 in the vertical direction; and dispensing needles 10, 10, 10, . . . retained in a dispensing needle holder 9 installed on the elevator stand 5.

According to the present embodiment, a cylinder 2A is fixed vertically downward at the lower part of the supporting frame 3 in the dispensing head 2, and at the same time, a pressurizing plate 2B is adhered at the tip of the piston rod of the cylinder 2A. If constituted as such, when suctioning under reduced pressure is carried out for the first and second low-pressure recovering devices 26 and 56, and the first and second suction discarding devices 27 and 57, airtightness can be increased by suppressing the filter plate or the SPE plate from above, and thus the efficiency is enhanced.

The first constant-temperature bath 12 is a first constant-temperature bath having a main body part 12A that is constructed by including a cartridge heater 14 built in at the internal center of the receiving stand 13 formed from an aluminum block, and also by disposing a Peltier element 15 and a heat sink 16 at the lower part of the receiving stand 13, wherein the upper part of the receiving stand 13 in the main body part 12A is covered by a lid 21 which has a silicone sheet pasted on the inside and has an inner lid 19 with a built-in cartridge heater 18 at the internal center, the inner lid being elastically supported via a spring 20. Furthermore, for this first constant-temperature bath 12, while opening and closing of the lid is operated manually in the present embodiment, the opening and closing may also be operated automatically. Furthermore, the silicone sheet 17 is intended to prevent evaluation of the sample inside when an aluminum sheet 61a of the microplate 61 has been perforated by dispensing needles 10, 10, 10, . . . .

The filter plate moving mechanism 39 is a moving mechanism having pulleys 41 and 42 installed at both ends in the length direction of a supporting plate 40 that is installed to stand along the longitudinal direction of the casing base 1, with one of the pulleys 41 and 42 being made to be rotary driven by a step motor 43, wherein a horizontally moving plate 45 is connected to a belt 44 hung between the two pulleys 41 and 42 and revolved, a vertical moving unit 46 is installed on the horizontally moving plate 45, and the vertical moving unit 46 is ascended and descended by a vertically moving rod 51 that supports a receiving frame 48 intended to receive an inner frame 47 at the upper end, and slides in the vertical direction along a guide 50 installed vertically inside the supporting frame 49, and by a ball screw 53 connected to the rotating axis 52a of a motor 52 fixed inside the supporting frame 49, and wherein the mechanism is constituted to have an elevating rod 51 connected to the vertically moving rod 54.

Furthermore, gaskets 47a and 48a for maintaining airtightness are installed between the inner frame 47 and the receiving frame 48.

The SPE plate moving mechanism 39 has the same constitution as that of the filter plate moving mechanism, and therefore, explanation will be omitted.

The second constant-temperature bath 29 is a second constant-temperature bath having a main body part 29A that is constructed by including a cartridge heater 31 built in at the internal center of the receiving stand 30 formed from an aluminum block, and also an air circulation path 32 installed across from the internal center to the surface, and by disposing a Peltier element 33 and a heat sink 34 at the lower part of the receiving stand 30, wherein an air circulation path 32 which is in communication with the above air circulation path 32 is provided between the upper part of the receiving stand 30 in the main body part 29A and the filter plate located thereon, and a duct 36 and a fan 37 are further provided to let the air discharged out of the filter plate flow again into the receiving stand 30 to thereby circulate, while the upper part of the receiving stand 30 in the main body part 29A is covered by a lid 38. Furthermore, in the second constant-temperature bath 29, the lid 38 is made to open and close automatically.

Next, the treatment operation of the automatic sugar chain pretreatment apparatus related to the embodiments described above will be explained according to the flow diagrams shown in FIG. 24 and FIG. 25.

<Hereinafter, Corresponding Step Numbers Will Also be Described.>

1. The cover of the casing base 1 is opened, the first constant-temperature bath 12 is opened, and the microplate 61, covered with an aluminum sheet while having a biological sample injected in each well, is placed on the receiving stand 13.

(The process up to this point corresponds approximately to the step (A-1).)

2. The dispensing head 2 is moved to suction 15 µl of 0.33 M ammonium bicarbonate from a container of the reagent rack 22, and is moved to perform dispensing to each well of the microplate 61.

3. In the same manner as in 2., 30 µl of a 0.4% solubilizing agent is dispensed.

4. The first constant-temperature bath 12 is closed and is heated at 37° C. for 10 minutes.

(The process up to this point corresponds approximately to the step (A-2).)

5. The lid is opened, and 5 µl (CV (Coefficient of Variation) 5%) of 120 mM dithiothreitol (DTT) is dispensed.

6. The lid is closed, and the first constant-temperature bath is heated at 60° C. for 30 minutes.

7. The lid is opened, and the first constant-temperature bath is cooled at room temperature.

(The process up to this point corresponds approximately to the step (A-3).)

8. 123 mM iodoacetamide (IAA) is dispensed in an amount of 10 µl (CV 5%).

9. The first constant-temperature bath is cooled at room temperature for 60 minutes in the dark.

(The process up to this point corresponds approximately to the step (A-4).)

10. Trypsin (400 U) is dispensed in an amount of 5 µl to each well of the microplate 61 which has been set up again in the first constant-temperature bath 12, with the lid open.

11. The lid is closed, and the first constant-temperature bath is heated at 37° C. for 60 minutes.

12. The first constant-temperature bath is further heated at 90° C. for 5 minutes.

13. The lid is opened, and the constant-temperature bath is cooled at room temperature.

(The process up to this point corresponds approximately to the step (A-5).)

14. Peptide-N-glycosidase F and peptide-N4-(acetyl-β-glucosaminyl)-asparagine amidase (PNGaseF) (2 U) are dispensed in an amount of 5 µl to each well of the microplate 61.

15. The lid is closed, and the first constant-temperature bath is heated at 37° C. for 12 hours.

(The process up to this point corresponds approximately to the step (A-6).)

16. 1 M acetic acid (AcOH) is dispensed in an amount of 200 µl to each well of the filter plate 62 containing polymer beads, which is set up in the suction discarding device 27.

17. The acetic acid is discarded by suction.

(The process up to this point corresponds approximately to the step (B-1).)

18. 50% ACN is dispensed in an amount of 300 µl.

19. Acetonitrile is discarded by suction.

20. ACN is dispensed in an amount of 300 µl.

21. ACN is discarded by suction.

(The process up to this point corresponds approximately to the step (B-2,3).)

22. The filter plate 62 containing polymer beads is moved to the position of the bottom wiper 38, and bottom wiping is performed. The filter plate is moved to the second constant-temperature bath 29 (the constant temperature bath opens automatically).

23. The second constant-temperature bath 29 is opened, and the enzymatically treated sample is dispensed in an amount of 20 µl to the filter plate 62 containing polymer beads, which is placed on the receiving stand 30.

(The process up to this point corresponds approximately to the step (B-4).)

24. 20 AcOH/ACN is dispensed in an amount of 200 µl.

25. The lid is closed, and the second constant-temperature bath is heated at 80° C. for 60 minutes.

26. 6 M guanidine hydrochloride is dispensed in an amount of 300 µl.

27. The second constant-temperature bath is cooled at room temperature for 10 minutes, with the lid open.

28. The filter plate 62 is moved to the suction discarding device 27.

29. Guanidine hydrochloride is discarded by suction.

(The process up to this point corresponds approximately to the step (B-5).)

30. 6 M guanidine hydrochloride is dispensed in an amount of 300 µl.

31. Guanidine hydrochloride is discarded by suction.

32. Water is dispensed in an amount of 300 µl.

33. Water is discarded by suction.

34. 10 M hydrochloric acid is dispensed in an amount of 300 µl.

35. Hydrochloric acid is discarded by suction.

(The process up to this point corresponds approximately to the step (B-6).)

36. MeOH is dispensed in an amount of 300 µl.

37. MeOH is discarded by suction.

(The process up to this point corresponds approximately to the step (B-7).)

38. The filter plate 62 is moved to the position of the bottom wiper 28, and bottom wiping is performed.

39. The filter plate 62 is moved to the second constant-temperature bath 29.

(The process up to this point corresponds approximately to the step (B-8).)

40. A reducing reagent is dispensed in an amount of 200 µl.

41. Light is shielded, and the second constant-temperature bath is cooled at room temperature for 30 minutes.

42. The filter plate 62 is moved to the suction discarding device 27.

43. The reducing reagent is discarded by suction.

44. MeOH is dispensed in an amount of 300 μl.

45. MeOH is discarded by suction.

46. The filter plate 62 is moved to the position of the bottom wiper 28, and bottom wiping is performed.

47. Water is dispensed in an amount of 300 μl.

48. Water is discarded by suction.

49. ACN is dispensed in an amount of 300 μl.

50. ACN is discarded by suction.

51. Bottom wiping is performed.

52. The filter plate 62 is moved to the second constant-temperature bath 29.

53. 100 mM MTT in DMSO/ACN is dispensed in an amount of 100 μl.

54. The lid is closed, and the second constant-temperature bath is heated at 60° C. for 60 minutes.

(The process up to this point corresponds approximately to the step (B-9).)

55. The filter plate 62 is moved to the suction discarding device 27.

56. MTT is discarded by suction.

57. ACN is dispensed in an amount of 300 μl.

58. ACN is discarded by suction.

(The process up to this point corresponds approximately to the step (B-10).)

59. The filter plate 62 is moved to the position of the bottom wiper 28, and bottom wiping is performed.

60. The filter plate 62 is moved to the suction discarding device 27.

61. Water is dispensed in an amount of 300 μl.

(The process up to this point corresponds approximately to the step (B-11).)

62. Water is discarded by suction.

63. 50 mM DTT is dispensed in an amount of 50 μl.

64. The filter plate 62 is moved to the second constant-temperature bath 29.

65. The lid is closed, and the second constant-temperature bath is heated at 60° C. for 5 minutes.

66. The lid is opened, and the second constant-temperature bath is cooled at room temperature for 15 minutes.

67. The filter plate 62 is moved to the low-pressure recovering device 26.

68. Pressure is reduced, and the sample is withdrawn into the microplate 25 and recovered.

(The process up to this point corresponds approximately to the first half of the step (B-12).)

69. The sample is cooled to 10° C., and the process is completed.

Thereafter, the treatment procedure is divided depending on the amount of the sample.

[When the Sample is Sufficient]

70. The sample in the microplate 25 is dispensed to the microplate for mixing 24.

71. MALDI matrix is dispensed in an amount of 2 μl to the microplate for mixing 24.

72. The sample in the microplate for mixing 24 is dotted in an amount of 2 μl on the target plate 58 on the target plate receiving stand 59.

(The process up to this point corresponds approximately to the second half of the step (B-12).)

73. End.

(The process up to this point corresponds approximately to the step (B-13).)

[When the Sample is in a Trace Amount]

74. The sample in the microplate 25 is dispensed in an amount of 20 μl to the microplate for mixing 23.

75. ACN is dispensed in an amount of 400 μl to the microplate for mixing 23.

76. Water is dispensed in an amount of 200 μl to the SPE plate positioned in the suction discarding device 57.

77. Water is discarded by suction.

78. ACN is dispensed in an amount of 200 μl to the SPE plate.

79. ACN is discarded by suction.

The sample in the microplate for mixing 23 is dispensed in an amount of 420 μl to the SPE plate.

81. The sample is discarded by suction.

82. 95% ACN is dispensed in an amount of 200 μl to the SPE plate.

83. ACN is discarded by suction.

84. 10% ACN is dispensed in an amount of 20 μl to the SPE plate.

85. The SPE plate is moved to the low-pressure recovering device 56.

86. Pressure is reduced, and the sample is withdrawn into the microplate 55 and recovered.

87. The sample in the microplate 55 is dispensed in an amount of 2 μl to the microplate for mixing 24.

88. MALDI matrix is dispensed in an amount of 2 μl to the microplate for mixing 24.

89. The sample in the microplate for mixing 24 is dotted in an amount of 2 μl on the target plate 58 on the target plate receiving stand 59.

90. End.

C) When performing mass spectrometry using a plate, the process of producing a plate for mass spectrometry having the captured sugar chain sample dotted thereon is carried out.

91. A process of disposing the tagged sugar chain sample solution obtained by the processes up to 73. on a plate for recovery; and optionally, 92. to 93. are carried out.

92. The tagged sugar chain sample solution from the plate for recovery and the organic solvent are disposed on the plate for mixing, so as to obtain a concentration of the organic solvent at which the sugar chain adsorbs to a solid phase.

93. The solid phase carrier-enclosed plate is provided.

94. The solid phase carrier-enclosed plate is activated in accordance with the phase of the solid phase carrier-enclosed plate, and the plate is washed.

95. The tagged sugar chain sample solution is added to the solid phase carrier-enclosed plate, and the sample solution is conditioned to a solvent having a polarity appropriate for the phase of the solid phase carrier-enclosed plate.

96. The tagged sugar chain sample solution is recovered by suction from the solid phase carrier-enclosed plate to the second plate for recovery.

When subjecting the tagged sugar chain sample solution to MALDI-TOF MS, the following processes are carried out.

97. The tagged sugar chain sample solution is mixed with a matrix for mass spectrometry, and the mixture is dotted on a plate for measurement.

98. Analysis of the sugar chain to be determined is carried out. This analysis can be performed using any known method, as described in the present specification.

The reference documents such as scientific articles, patents and patent applications that are cited in the present invention have been incorporated in their entirety by reference to the same extent as they are respectively described in detail.

As discussed above, the present invention has been illustrated using preferred embodiments of the present invention, but the present invention is not intended to be interpreted as being limited to these embodiments. It should be understood that the scope of the present invention is definitely interpreted based only on the scope of claims. Those skilled in the art will understand, from the specific descriptions of the preferred embodiments of the present invention, that an equivalent scope of invention can be carried out based on the descriptions of the present invention and common technical knowledge. It is to be understood that the disclosures of the patents, patent applications and documents cited in the present specification have been definitely incorporated in the present specification by reference, in the same manner as that the disclosures are specifically described per se in the present specification.

EXAMPLES

Hereinafter, the present invention will be described in more detail by way of Examples, but this invention is not intended to be limited to the following examples.

Example 1

BLOTGLYCOABC™ Beads: Integrated Type Glycoblotting Technology for Rapid, Large-Scale Clinical Glycomics The following abbreviations will be used as necessary.
CDG: Congenital disorders of glycosylation
DTT: Dithiothreitol
HCC: Hepatic cell cancer
HPLC: High performance liquid chromatography
MALDI-TOF: Matrix-assisted laser desorption ionization-Time-of-flight
(Order of Experiment)
(Materials)

The clinical study of the present Example was approved by the Ethics Committee of Hokkaido University Hospital. Explanation was offered to and consent was obtained from all of serum donors. Peptide-N-glycosidase F (PNGase F) was purchased from Roche (Mannheim, Germany). 3-Methyl-1-p-tolyltriazene (MTT), 8 M borane-pyridine complex and dithiothreitol (DTT) were obtained from Sigma-Aldrich, Inc. (St. Louis, Mo.). BLOTGLYCOABC™ beads were prepared as will be described additionally. This is now commercially available from Sumitomo Bakelite Co., Ltd. (Tokyo, Japan). Other reagents and solvents were obtained, unless stated otherwise, from Wako Pure Chemical Industries, Ltd. (Tokyo, Japan). The blood serum of CDG patients was kindly supplied by Professor H. H. Freeze of Burnham Institute for Medical Research (La Jolla, Calif.).

Release of N-Glycans from Human Blood Serum)

Whole human blood serum was treated according to the conditions previously reported by the group of the present inventors (Kita, Y., Miura, Y., Furukawa, J. I., Nakano, M., Shinohara, Y., Ohno, M., Takimoto, A., and Nishimura, S. I. (2007) Mol. Cell. Proteomics 6, 1437-1445), to release reducing type N-glycans. Briefly speaking, 10 µl of a serum aliquot was diluted 6-fold in 83 mM ammonium hydrogen carbonate containing a surfactant and 10 mM DTT. After incubating the mixture at 60° C. for 30 minutes, one volume (10 µl) of 123 mM iodoacetamide was added thereto, and the mixture was incubated for one hour at room temperature in the dark. 400 Units of trypsin (Sigma-Aldrich) was added to this solution, and the mixture was incubated for one hour at 37° C. Trypsin was thermally deactivated, and then 2 units of PNGase F was added to the mixture. The resulting mixture was incubated overnight at 37° C. The entirety of released N-glycans (neutral glycans and sialylglycans) in the digestion mixture was directly used for glycoblotting using BLOTGLYCOABC™ beads as follows.

(The General Protocol of Glycoblotting by BLOTGLYCO-ABC™ Beads)

40 µl BLOTGLYCOABC™ beads (50% suspension) was dispersed on the wells of a filter plate MultiScreen Solvinert (Millipore). Those beads were rinsed with 1M of aqueous acetic acid (AcOH), 50% aqueous acetonitrile and acetonitrile (ACN) using a reduced pressure manifold in order. 20 µl of whole serum (equivalent to 2.5 µl of serum) digested with trypsin and PNGase F was transferred to the wells and then, 200 µl of 2% AcOH in acetonitrile was added thereto. The plate was incubated at 80° C. in a TurboVap 96 concentrator (Caliper Life Sciences, Inc., Hopkinton, Mass.) without using nitrogen gas flow and dried. It took usually 30 min. The plate was rinsed three times with 300 µl of 6M guanidine hydrochloride in 50 mM of ammonium carbohydrate and then, rinsed three times with 300 µl of water. After methyl esterification on beads (Miura, Y., Shinohara, Y., Furukawa, J. I., Nagahori, N., and Nishimura, S. I. (2007) Chem. Eur. J. 13, 4797-4804), the beads were rinsed using 300 µl of 10 mM of HCl, 50% aqueous acetonitrile and acetonitrile in order. The wells were incubated at 60° C. for 60 min together with 100 µl of 100 mM 3-methyl-1-p-tolyl triazene in dimethylsulfoxide-ACN (1:1). The solution was removed by applying reduced pressure and then, the beads were rinsed with ACN, water and MeOH (3×300 µl) in order. Hydrazone bonding between oligosaccharide and fluorescent probe on the bead was stabilized by incubation with a reducing agent (0.8 M borane-pyridine) according to a process previously reported (Lohse, A., Martins, R., Jorgensen, M. R., and Hindsgaul, O. (2006) Solid-phase oligosaccharide tagging (SPOT):Validation on glycolipid-derived structures. Angew. Chem. Int. Ed. Engl. 45, 4167-4172). The reduction was carried out at room temperature in dark for 30 minutes. After removing the mixture, the bead were rinsed with MeOH, CAN and water (3×300 µl) in order. On the wells, 50 µl of 50 mM DTT in 5 mM ammonium carbohydrate was added, the plate was incubated at 60° C. for 5 min and further incubated at room temperature for 15 min. The concentrated N-glycan treated as described above was collected from the bead in the DTT solution.

(Mass Spectrometry)

The collected N-glycan (0.5 µl) in the DTT solution was directly arranged on Anchor Chip 400/384 (Bruker Daltonics, Germany), mixed with the equal volume of matrix solution (the 9:1 mixture of DHB and DHB sodium salt (respectively 10 mg/ml in 30% ACN)) and dried under reduced pressure to obtain analyte crystal. Its mass spectrum was obtained representatively summarizing 100×5 shots using UltraFlex II TOF/TOF (Bruker Daltonics) in reflector positive ion mode.

(Statistical Analysis)

In the present research, the maximum 44 N-glycan peaks in MALDI-TOF MS spectrum were selected using a software called FlexAnalysis version 3 (Bruker Daltonics, German). All statistical analyses were carried out using those originally developed with MATLAB (Version 7.4) (The Mathworks, Inc.) language using Statistics Toolbox unless otherwise noted.

(CDG Case)

Respective subtypes were repeatedly measured (n=6). The reason was that only one for respective samples was available for these subtypes. The isotopic areas of respective glycans were normalized against the known amount of internal standard. In order to identify N-glycans that may be used for discrimination between CDG-I subtype and normal control, the present inventors carried out classification using algorism for expected value maximization. The algorism separates the mixtures of various data distributions in the repeating steps of maximum evaluation method (Redner, R. A., and Walker, H. F. (1984) Soc. Indust. Appl. Math. Rev. 26, 195-239.) Preclinical component analysis (PCA) was carried out using Spotfire DecisionSite (version 9.0 Somerville, Mass.). The present inventors plotted initial two principal components.

(HCC Case)

Cut-off line for calculation was regulated as 0.3% among total area. The statistical difference of disorder condition against normal condition was calculated using student t calibration. The difference was regarded as statistically significant in case of P<0.001. In order to identify essential characteristics for optimally classifying serum between the two conditions of disorder condition and normal condition, the present inventors applied successively progressive selection algorism. The algorism selected the better combination of N-glycan peaks in order based on the error rate of the one extract method (LOO) of k-proximal discriminator (k=3).

(Result)

(The Principal Illustration of Clinical Glycomics at BLOT-GLYCOABC™ Beads Base)

The novel method described in the present specification can provides extremely simple and convenient approach for the concentration analysis of composite glyco-adelphus without any special training (FIG. 10a). The present inventors designed N-(2-aminobenzoyl)cysteine hydrazide (ABCh) in order to establish "all in one" protocol, bonded the adelphus with thiopropyl Sepharose 6B and used it in order to obtain stable hydrazide-functionalized polymer support (namely, BLOTGLYCOABC™ beads) (FIG. 10b, refer to the synthesis of BLOTGLYCOABC™ beads and illustration after the characterization, and the following scheme 1).

(Table 2) The synthesis route of ABCh (N-(2-aminobenzoyl)cysteine hydrazide) and the preparation of BLOTGLYCOABC™ beads.

TABLE 2

Supplementery Scheme 1

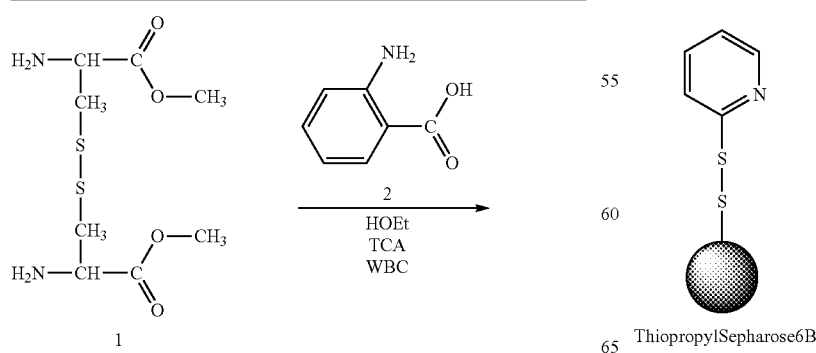

TABLE 2-continued

Supplementery Scheme 1

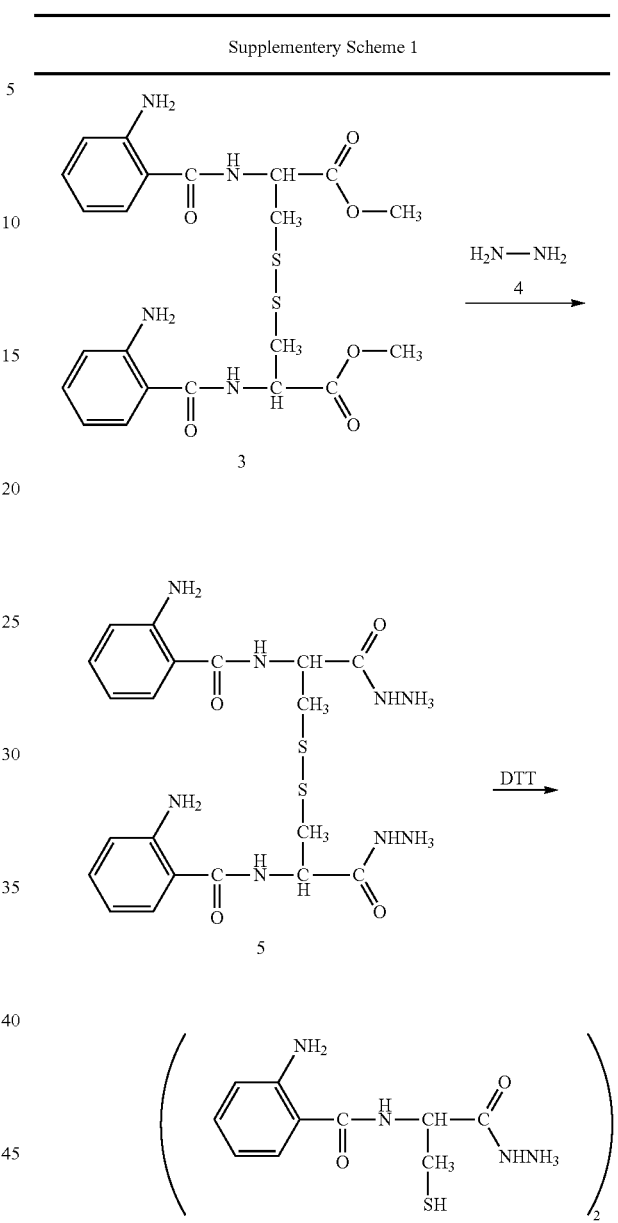

TABLE 2-continued

Supplementery Scheme 1

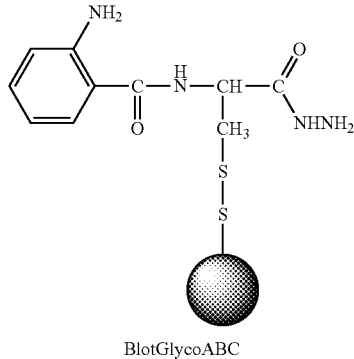 [SMILES: CSSCC(NC(=O)c1ccccc1N)C(=O)NN]

BlotGlycoABC

The synthesis route of ABCh (N-(2-aminobenzoyl)cysteine hydrazide) and the preparation of BLOTGLYCOABC™ beads.

The hydrazide group reacts with an aldehyde group or a ketone group that is very rare in a general biological sample, excepting glycans having reductive hemiacetal terminal. The formation of the hydrazone bond between BLOTGLYCO-ABC™ beads and glycan is reversible and enables the discharge of partially reducing sugar. Otherwise, it can be reduced for converting stable C—N bond (Lohse, A., Martins, R., Jorgensen, M. R., and Hindsgaul, O. (2006) Angew. Chem. Int. Ed. Engl. 45, 4167-4172). The chemical property includes various reagents (for example, dithiothreitol (DTT), iodoacetamide, surfactant, etc.). It is suitable for enriching glycans from complex biological materials even in the presence of various amines and reagents that are used in the preparation of proteomics sample. The quantitative ligation of general N bond type oligosaccharide is generated by the method of the present inventors without losing sialic acid at all. Disulfide bond bonding thiopropyl Sepharose 6B with ABCh probe enabled the quantitative collection of N-glycan enriched by being treated with DTT in eluate buffer. The collected sample contains neutral and acidic glycans and can be immediately used for the following quantitative analysis, using some of HPLC and MS analysis application.

Although intact neutral glycan and sialylated glycan are collected by the above-mentioned method, it is known that sialylated oligosaccharide is decomposed by their minus charge in general MS analysis. Since the stabilization of sialic acid is essential for the quantitative MS analysis of sialic oligosaccharide, the simple O-methyl esterification of sialic acid residue by 3-methyl-1-p-tolyltriazene (MTT) was incorporated in the protocol. In the capture of whole N-glycan by the intervention of stable hydrazone bond by BLOTGLYCO-ABC™ beads, methyl esterification on the bead of sialic acid and the reduction of hydrazone bond on the bead were carried out in order to enable mass measurement that is high in reliability and high in reproducibility for both of neutral glycoform and acidic glycoform in positive reflector mode in MALDI-TOF.

In order to exemplify a novel method, the present inventors provided human serum (2.5 µl) for optimal protocol that used BLOTGLYCOABC™ beads. The portion of sample solution equivalent to 25 nl serum that "can be immediately analyzed" was directly deposited on a target plate to be provided for MALDI-TOF analysis (positive reflector mode). The present inventors quantified 44 kinds of N-glycans (FIG. 11A and Table 3). 44 Kinds of N-glycans derived from human serum were set as the target in the present research. The peak 33 is internal standard that was added for quantification. The annotation of composition and deduced structure shown in the column of abbreviated description were obtained by Proteome Systems (glycosuite.proteomesystems.com/glycosuite/glycodb) that is GlycoSuite online database.

TABLE 3

| Peak number | m/z | Composition | Abbreviated description |
|---|---|---|---|
| 1 | 1495.511 | $(Hex)_2 + (Man)_3(GlcNAc)_2$ | Man5 |
| 2 | 1520.543 | $(HexNAc)_1(Deoxyhexose)_1 + (Man)_3(GlcNAc)_2$ | CoreFGN1 |
| 3 | 1636.538 | $(Hex)_1(HexNAc)_1 + (Man)_3(GlcNAc)_2$ | CoreG1GN1 |
| 4 | 1577.565 | $(HexNAc)_2 + (Man)_3(GlcNAc)_2$ | NA2G0 |
| 5 | 1657.564 | $(Hex)_3 + (Man)_3(GlcNAc)_2$ | Man6 |
| 6 | 1723.628 | $(HexNAc)_2(Deoxyhexose)_1 + (Man)_3(GlcNAc)_2$ | NA2FG0 |
| 7 | 1739.617 | $(Hex)_1(HexNAc)_2 + (Man)_3(GlcNAc)_2$ | NA2G1 |
| 8 | 1780.644 | $(HexNAc)_3 + (Man)_3(GlcNAc)_2$ | bisG0 |
| 9 | 1819.617 | $(Hex)_4 + (Man)_3(GlcNAc)_2$ | Man7 |
| 10 | 1841.548 | $(Hex)_1(HexNAc)_1(NeuAc)_1 + (Man)_3(GlcNAc)_2$ | A1(G1GN1) |
| 11 | 1885.675 | $(Hex)_1(HexNAc)_2(Deoxyhexose)_1 + (Man)_3(GlcNAc)_2$ | NA2FG1 |
| 12 | 1901.670 | $(Hex)_2(HexNAc)_2 + (Man)_3(GlcNAc)_2$ | NA2 |
| 13 | 1828.702 | $(HexNAc)_3(Deoxyhexose)_1 + (Man)_3(GlcNAc)_2$ | bisFG0 |
| 14 | 1942.097 | $(Hex)_1(HexNAc)_3 + (Man)_3(GlcNAc)_2$ | bis(G1) |
| 15 | 1981.670 | $(Hex)_5(Man)_3(GlcNAc)_2$ | Man8 |
| 16 | 1987.707 | $(Hex)_1(HexNAc)_1(Deoxyhexose)_1(NeuAc)_1 + (Man)_3(GlcNAc)_2$ | A1F(G1GN1) |
| 17 | 2003.702 | $(Hex)_2(HexNAc)_1(NeuAc)_1 + (Man)_3(GlcMAc)_2$ | A1M1(G1GN1) |
| 18 | 2044.729 | $(Hex)_1(HexNAc)_2(NeuAc)_1 + (Man)_3(GlcNAc)_2$ | A1(G1) |
| 19 | 2047.728 | $(Hex)_2(HexNAc)_2(Deoxyhexose)_1 + (Man)_3(GlcNAc)_2$ | NA2F |
| 20 | 2088.755 | $(Hex)_1(HexNAc)_3(Deoxyhexose)_1 + (Man)_3(GlcNAc)_2$ | bisF(G1) |
| 21 | 2104.750 | $(Hex)_2(HexNAc)_3 + (Man)_3(GlcNAc)_2$ | bis(G2) |
| 22 | 2143.725 | $(Hex)_2 + (Man)_3(GlcNAc)_2$ | Man9 |
| 23 | 2165.755 | $(Hex)_3(HexNAc)_1(NeuAc)_1 + (Man)3(GlcNAc)_2$ | A1Man5 |
| 24 | 2206.781 | $(Hex)_2(HexNAc)_2(NeuAc)_1 + (Man)3(GlcNAc)_2$ | A1 |
| 25 | 2247.808 | $(Hex)_1(HexNAc)_3(NeuAc)_1 + (Man)3(GlcNAc)_2$ | NA3(G1A1) |
| 26 | 2250.808 | $(Hex)_2(HexNAc)_3(Deoxyhexose)_1 + (Man)_3(GlcNAc)_2$ | bisF(G2) |
| 27 | 2206.802 | $(Hex)_3(HexNAc)_3 + (Man)_3(GlcNAc)_2$ | NA3 |
| 28 | 2352.839 | $(Hex)_2(HexNAc)_2(Deoxyhexose)_1(NeuAc)_1 + (Man)_3(GlcNAc)_2$ | A1F |
| 29 | 2393.866 | $(Hex)_1(HexNAc)_3(Deoxyhexose)_1(NeuAc)_1 + (Man)_3(GlcNAc)_2$ | NA3F(G1A1) |
| 30 | 2409.861 | $(Hex)_2(HexNAc)_3(NeuAc)_1 + (Man)_3(GlcNAc)_2$ | bis(G2A1) |

TABLE 3-continued

| Peak number | m/z | Composition | Abbreviated description |
|---|---|---|---|
| 31 | 2412.860 | $(Hex)_3(HexNAc)_3(Deoxyhexose)_1 + (Man)_3(GlcNAc)_2$ | bsF(G3) |
| 32 | 2469.882 | $(Hex)_3(HexNAc)_4 + (Man)_3(GlcNAc)_2$ | NA4(G3)/NA3bis |
| 33 | 2481.893 | $(Hex)_2(HexNAc)_2(NeuAcAmide)_2 + (Man)_3(GlcNAc)_2$ | A2 amidE |
| 34 | 2511.892 | $(Hex)_2(HexNAc)_2(NeuAc)_2 + (Man)_3(GlcNAc)_2$ | A2 |
| 35 | 2539.924 | $(Hex)_1(HexNAc)_3(Deoxyhexose)_2(NeuAc)_1 + (Man)_3(GlcNAc)_2$ | |
| 36 | 2555.919 | $(Hex)_2(HexNAc)_3(Deoxyhexose)1(NeuAc)_1 + (Man)_3(GlcNAc)_2$ | bisF(G2A1) |
| 37 | 2571.912 | $(Hex)_3(HexNAc)_3(NeuAc)_1 + (Man)_3(GlcNAc)_2$ | NA3(A1) |
| 38 | 2615.940 | $(Hex)_3(HexNAc)_4(Deoxyhexose)_1 + (Man)_3(GlcNAc)_2$ | NA3Fbis |
| 39 | 2631.935 | $(Hex)_4(HexNAc)_4 + (Man)_3(GlcNAc)_2$ | NA4 |
| 40 | 2657.960 | $(Hex)_2(HexNAc)_2(Deoxyhexose)_1(NeuAc)_2 + (Man)_3(GlcNAc)_2$ | A2F |
| 41 | 2717.971 | $(Hex)_3(HexNAc)_3(Deoxyhexose)_1(NeuAc)_1 + (Man)_3(GlcNAc)_2$ | NA3F(A1) |
| 42 | 2861.030 | $(Hex)_2(HexNAc)_2(Deoxyhexose)_1(NeuAc)_2 + (Man)_3(GlcNAc)_2$ | bisF(A2) |
| 43 | 2677.025 | $(Hex)_3(HexNAc)_3(NeuAc)_2 + (Man)_3(GlcNAc)_2$ | NA3(A2) |
| 44 | 3023.083 | $(Hex)_3(HexNAc)_3(Deoxyhexose)_1(NeuAc)_2 + (Man)_3(GlcNAc)_2$ | NA3F(A2) |
| 45 | 3162.136 | $(Hex)_3(HexNAc)_3(NeuAc)_3 + (Man)_3(GlcNAc)_2$ | A3 |

These glycans can be detected in all samples and these quantities were normalized for peak number 33 (spike, that is, A2 amide abruptly raised) as internal standard. Once N-glycans are applicable by the PNGase F treatment (Kita, Y., Miura, Y., Furukawa, J. I., Nakano, M., Shinohara, Y., Ohno, M., Takimoto, A., and Nishimura, S.-I. (2007) Mol. Cell. Proteomics 6, 1437-1445.) of whole serum glycol protein, it takes only less than 4 hours to identify the whole N-glycan profile by the idiomatic operation of BLOTGLYCOABC™ beads and MALDI-TOF MS. It should be marked that the solid phase protocol is the first example of "All in One" GlycoBlotting technology in a single automated work flow. The present inventors are now studying and developing a sample processing machine suitable for automated GlycoBlotting that uses BLOTGLYCOABC™ beads. In fact, "All in One" GlycoBlotting protocol based on BLOTGLYCO-ABC™ beads can be preliminarily transferred to automated platform by use in combination with standard multi-wells filter plate form under the flow chart optimized for human serum application (FIG. 8). The effectiveness of the automated protocol was evaluated by simultaneously performing same human serum digestive articles (FIG. 14). Further, its precise reliability was confirmed by good reproducibility (FIG. 4).

(Table 4) CV; Fluctuation Counting

It should be noted that hydrazone bond is not reduced in the automated GlycoBlotting because of collecting oligosaccharide in reducing sugar mode by acid processing and the mass difference of −2Da is generated in comparison with the mass of Tables 3 and 4.

TABLE 4

| m/z | Number of figure | Minimum | 25% Percentile | Median | 75% Percentile | Maximum | Average | Standard deviation | CV |
|---|---|---|---|---|---|---|---|---|---|
| 1493.365112 | 8 | 0.094 | 0.110 | 0.120 | 0.126 | 0.148 | 0.119 | 0.016 | 13.50% |
| 1855.395142 | 8 | 0.122 | 0.129 | 0.140 | 0.154 | 0.172 | 0.142 | 0.017 | 11.88% |
| 1721.453491 | 8 | 1.079 | 1.186 | 1.177 | 1.198 | 1.264 | 1.178 | 0.052 | 4.37% |
| 1737.439331 | 8 | 0.066 | 0.082 | 0.086 | 0.097 | 0.112 | 0.089 | 0.015 | 16.39% |
| 1778.443481 | 8 | 0.000 | 0.044 | 0.054 | 0.052 | 0.072 | 0.049 | 0.022 | 45.08% |
| 1839.444214 | 8 | 0.063 | 0.078 | 0.094 | 0.109 | 0.130 | 0.094 | 0.023 | 24.02% |
| 1883.491821 | 8 | 2.130 | 2.247 | 2.315 | 2.344 | 2.382 | 2.291 | 0.082 | 3.56% |
| 1899.471436 | 8 | 0.083 | 0.109 | 0.119 | 0.144 | 0.149 | 0.122 | 0.023 | 18.48% |
| 1924.493042 | 8 | 0.143 | 0.154 | 0.166 | 0.180 | 0.213 | 0.170 | 0.022 | 13.08% |
| 1940.455688 | 8 | 0.072 | 0.082 | 0.088 | 0.107 | 0.118 | 0.092 | 0.016 | 17.68% |
| 1979.456787 | 8 | 0.000 | 0.051 | 0.069 | 0.080 | 0.107 | 0.063 | 0.032 | 50.04% |
| 2001.482666 | 8 | 0.000 | 0.057 | 0.062 | 0.086 | 0.093 | 0.063 | 0.029 | 46.72% |
| 2042.485403 | 8 | 0.092 | 0.095 | 0.111 | 0.121 | 0.167 | 0.114 | 0.025 | 21.73% |
| 2045.519043 | 8 | 1.000 | 1.000 | 1.000 | 1.000 | 1.000 | 1.000 | 0.000 | 0.00% |
| 2086.525879 | 8 | 0.244 | 0.253 | 0.268 | 0.280 | 0.311 | 0.270 | 0.022 | 8.21% |
| 2188.534424 | 8 | 0.129 | 0.143 | 0.157 | 0.161 | 0.207 | 0.157 | 0.023 | 14.74% |
| 2204.559814 | 8 | 3.122 | 3.453 | 3.521 | 3.782 | 3.966 | 3.600 | 0.277 | 7.70% |
| 2245.557617 | 8 | 0.083 | 0.096 | 0.113 | 0.141 | 0.161 | 0.118 | 0.028 | 23.98% |
| 2248.559082 | 8 | 0.109 | 0.128 | 0.142 | 0.154 | 0.173 | 0.141 | 0.020 | 14.14% |
| 2350.59082 | 8 | 1.120 | 1.152 | 1.174 | 1.231 | 1.296 | 1.191 | 0.058 | 4.87% |
| 2381.575439 | 8 | 0.041 | 0.056 | 0.069 | 0.080 | 0.088 | 0.068 | 0.016 | 24.19% |
| 2407.578369 | 8 | 0.128 | 0.143 | 0.151 | 0.182 | 0.208 | 0.161 | 0.026 | 16.37% |
| 2467.575195 | 8 | 0.041 | 0.056 | 0.074 | 0.087 | 0.100 | 0.072 | 0.021 | 29.09% |
| 2509.64624 | 8 | 19.400 | 22.080 | 24.270 | 25.980 | 28.860 | 24.110 | 2.995 | 12.42% |
| 2537.617188 | 8 | 0.073 | 0.106 | 0.143 | 0.181 | 0.305 | 0.155 | 0.072 | 46.72% |
| 2551.622314 | 8 | 0.159 | 0.210 | 0.276 | 0.334 | 0.416 | 0.277 | 0.088 | 31.79% |
| 2553.638184 | 8 | 0.403 | 0.458 | 0.480 | 0.503 | 0.504 | 0.474 | 0.034 | 7.27% |
| 2569.62207 | 8 | 0.246 | 0.340 | 0.433 | 0.597 | 0.682 | 0.484 | 0.209 | 43.20% |
| 2658.660156 | 8 | 0.702 | 0.760 | 0.845 | 0.874 | 0.898 | 0.820 | 0.071 | 8.62% |
| 2858.700195 | 8 | 0.195 | 0.218 | 0.241 | 0.255 | 0.281 | 0.235 | 0.024 | 10.33% |
| 2874.699463 | 8 | 0.086 | 0.109 | 0.143 | 0.147 | 0.163 | 0.131 | 0.026 | 20.17% |
| 3179.767672 | 8 | 0.115 | 0.146 | 0.169 | 0.181 | 0.197 | 0.163 | 0.026 | 16.11% |

(Detection of Change in Congenital Glycol Deficiency (CDG))

The detection of N-glycan in whole serum protein and the determination of profile are very useful for the rapid identification of abnormal protein glycosylation provoked by congenital change and acquired change. The present inventors tested the technology of the present inventors for serum derived from a subject suffering from congenital deficiency of glycosylation (CDG) that is rare disease that is hereditary human disorder group (Mandato, C., Brive, L., Miura, Y., Davis, J. A., Di Cosmo, N., Lucariello, S., Pagliardini, S., Seo, N. S., Parenti, G., Vecchione, R., Freeze, H. H., and Vajro, P. (2006) Pediatric Res. 59, 293-298.). CDG's exceeding 19 subgroups have been hitherto identified (Freeze, H. H., and Aebi, M. (2005) Curr. Opin. Struc. Biol. 15, 490-498.). These CDG's are generated from the biological synthesis of N-glycan precursor or specified type N-glycan assembly or the deficiency of either of them that are provoked by the rejection (type 1 CDG) or immature processing (type 2 CDG) of sugar chain bonded with protein. The GlycoBlotting technology of the present inventors is based on BLOTGLYCO-ABC™ beads and MALDI-TOF MS, but the present inventors could detect abnormal glycosylated pattern in whole serum glycoprotein. Respective analyses were repeated 6 times (n=6) and peak area in MALDI-TOF MS spectrum was normalized against the fixed amount of A2 amide that is internal standard. As anticipated, the present inventors observed abnormal N-glycan profile (for example, some immature small size N-glycan chains) for a type 2 CDG (CDG-II) subject elapsing the concrete step of glycosylation deficiency (FIG. 11B, the increase of iv-vii) [unclassified subgroups of CDG-I and CDG-II]. On the other hand, N-glycan enriched from the serum of a type 1 CDG (CDG-I) subject showed N-glycan profile that is extremely similar as a normal analyte (FIG. 11B ii and iii). However, its result showed also the significant decrease of total N-glycan in comparison with normal donor (1011±69 µM) (575±46 µM and 692±41 µM for respective CDG-Ia subject and CDG 1b subject; and refer to Table 4). This suggests clearly that deficiency in CDG-I loses the whole glycan chains, to a certain degree caused by that the biological synthesis of precursor is not possible.

The advantage of quantitative glycomics in the diagnosis marker of the CDG 1 subject is clear. The reason is that data distribution formed by the quantities of 42 kinds of N-glycans detected can be used for the simple differentiation of a subject from normal serum (FIG. 11C, a panel at left side and a panel at center). It was clarified by the result that the pair of combination of the quantities of N-glycans verifies diagnostic differentiation between the CDG-I subject, CDG-Ia subject and CDG-Ib subject (FIG. 11C, a panel at right side). Further, the present inventors used the principal component analysis (PCA) of all CDG subsystems of the acquired whole N-glycan profiles in order to interpret complex multi spectra data set. The initial two principal components discriminated clearly CDG subsystem containing normal donor. It was confirmed from these results that it can be discriminated from healthy control by the profiles of N-glycan set of whole serums and the specific subsystem of CDG can be discriminated from other subsystem of CDG.

(Diagnostic Discrimination of Hepatocellular Carcinoma)

In order to verify the elasticity of the present protocol in large scale clinical glycomics, the present inventors applied the technology of the present inventors to the serums of plural number of subjects suffering from hepatocellular carcinoma (HCC). As recognized, the use of Glycoblotting protocol based on BLOTGLYCOABC™ beads and MALDI-TOF analysis enabled the speedy and quantitative determination of N-glycan profiles of $10^3$ human serum samples (83 subjects and 20 normal control). In order to most suitably classify serums between two relative classes, disease and normal by identifying essential characteristics, the present inventors applied successive forward selection algorism that selects the better combination of N-glycan peaks based on the error rate (k=3) of one extract method (LOO) of k proximal discriminator (FIGS. 12a and 12b). When the present inventors selected the proportion of whole two peaks between acquired peaks that show significant difference (t calibration at both sides and P <0.001) between disease and control, the algorism selected the proportion (FIG. 12c) of the quantities of N-glycans that discriminated HCC sample at 100% accuracy from normal control (FIG. 12a). Accordingly, it was verified that the determination of whole serum N-glycan profiles of BLOTGLYCOABC™ beads base provides simple noninvasive diagnostic tool for disease that has been previously difficult in early diagnosis or discrimination.

(Application to Cell Glycomics)

Cell and tissue in addition to serum are important biological materials in clinical glycomics. The present inventors applied the purification protocol established in the above-description, to cultured cells in order to study the N-glycan forms of whole cells. The PC-3 cell of human prostate cancer and the PrEC cell of normal human prostate epithelial were cultured and their whole protein extracts were provided for BLOTGLYCOABC™ beads treatment. In similar manner as the N-glycan profile of serum, whole cell glycan forms were clarified by the small amount of starting material (5-8×$10^6$ cells). The N-glycan profiles unique to respective cell species were successfully detected by the result and it was shown that the approach of the present inventors for serum glycomics shown in the above-description is equally suitable for cell glycomics (FIG. 13). The optimization of cell glycomics/tissue glycomics can let general protocol applicable to characteristic with further high throughput.

(The Synthesis and Characterization of BLOTGLYCO-ABC™ Beads)

General method and materials: All commercially available starting materials and solvents are reagent grade and they were used as they were at purchase. 2-Amino benzoate, 1-hydroxybenzotriazole hydrate (HOBt) and L-cystine dimethyl-esters dihydrochloride were bought from Sigma-Aldrich Chemical. N-(3-dimethylaminopropyl)-N-ethylcarbodiim-ide mono hydrochloride (WSC) was purchased from TCI (Japan). Thiopropyl Sepharose 6B was purchased from GE Healthcare Biosciences. All other chemical substances are ultra high purity grade and purchased from Wako Pure Chemicals Co., Ltd. (Japan). 1H NMR spectra and 13C NMR spectra were measured at 600 MHz with a Bruker DPX-600 spectrometer using DMSO as solvent. All other chemical reactions were carried out under nitrogen atmosphere in anhydrous solvent shielding light unless otherwise noted. TLC was carried out on a Merck precoated plate (20×20 cm, layer thickness of 0.25 mm, and Silica Gel 60F254); spots were visualized by spraying the solution of 90:5:5 (v/v/v) of methanol:p-anis aldehydes: concentrated sulfuric acid and heating it at 180° C. for about 30 seconds, or under ultraviolet rays (256 nm or 365 nm) when it is applicable. The organic extract was dried on anhydrous $MgSO_4$ and the solution was concentrated at less than 50° C. under reduced pressure.

N,N'-(2-aminobenzoyl)cystine dimethylesters 3:2-aminobenzoic acid (8.22 g (60.0 mmol)) was dissolved in 60 ml of tetrahydrofuran in a round-bottom flask and the mixture was cooled in an ice bath. HOBt (9.18 g, 26.9 mmol), dimethyl ester of L-cystine dihydrochloride (10.23 g, 30.0 mmol) and triethylamine (8.37 mL) were added to the solution. WSC (11.49 g, 60.0 mmol) was added to the solution, the solution was stirred for 15 minutes on an ice bath, and the mixture was stirred at room temperature over night. After completion of the reaction, the solvents were removed by evaporation and the residue was dissolved in 150 ml of chloroform. The chloroform solution was successively rinsed with the saturated aqueous solution of $NaHCO_3$ and the saturated aqueous solution of NaCl, its organic phase was dehydrated with $Na_2SO_4$ and the solvents were removed by evaporation to obtain yellow powder (16.4 g, 32.4 mmol, 108%).

1H NMR (500 MHz, $CDCl_3$) δ: 3.32 (d, J=5.3 Hz, 2H, CH2), 3.77 (s, 3H, CH3), 5.03 (dd, J=5.3, 12.6 Hz, 1H, CH), 3.32 (d, J=5.3 Hz, 2H, $CH_2$), 6.62 (t, J=7.3 Hz, 1H, Ph), 6.69 (d, J=8.1 Hz, 1H, Ph), 6.98 (bd, J=6.6 Hz, 1H, NH), 7.20 (t, J=7.2 Hz, 1H, Ph), 7.43 (d, J=8.0 Hz, 1H, Ph).

N,N'-(2-aminobenzoyl)cystine hydrazide 5: Hydrazine monohydrate (31.6 g, 631 mmol) was added to the solution of 320 mL of methyl alcohol, and the mixture was stirred at room temperature over night to obtain precipitate. The precipitate was collected by filtration and rinsed with 320 mL of methyl alcohol. The residue was dried under reduced pressure to obtain a pure compound 5 (10.8 g, 21.3 mmol, 67.4%).

N-(2-aminobenzoyl)cystine hydrazide 6:1 M hydrochloric acid (14.22 mL) was added to the solution of 96 mL of acetonitrile-water (50%, v/v) and the solution was stirred. The pH of the solvent was adjusted at 7.0 by adding the aqueous solution (17.06 mL) of 1 M ammonium carbohydrate, then the aqueous solution (4.74 mL) of 1 M dithiothreitol (DTT) and the mixture was stirred at room temperature for 2 hours. After completion of the reaction by TLC test, the solution was extracted with ethyl acetate. The organic phase was dehydrated with $Na_2SO_4$ and the solvent was removed by evaporation to obtain white powder 6 (2.4 g, 9.44 mmol, quantification). 1H NMR (500 MHz, DMSO) δ: 2.36 (bs, 1H, SH), 2.84 (m, 2H, $CH_2$), 4.26 (bs, 2H, NHNH2), 4.45 (dd, J=2.1, 8.0 Hz, 1H, CH), 6.36 (bs, 2H, PhNH2), 6.52 (t, J=7.5 Hz, 1H, Ph), 6.69 (d, J=8.2 Hz, 1H, Ph), 7.15 (t, J=8.2 Hz, 1H, Ph), 7.60 (d, J=7.9 Hz, 1H, Ph), 8.16 (d, J=7.9 Hz, CHNH), and 9.21 (s, 1H, NHNH2).

The preparation of BLOTGLYCOABC™ beads: 10 mL of thiopropyl Sepharose 6B resin was rinsed with the aqueous solution of 0.1 M ammonium carbohydrate in a dispensable column. These beads were immersed in 6.7 mL of acetonitrile/water (50%, v/v) and then, 0.1 M solution of ABCh in acetonitrile/water (50%, v/v) (3.3 mL) was added thereto. The slurry was mixed at room temperature for 30 minutes. After the reaction, the beads were adequately rinsed with acetonitrile/water (50%, v/v), 0.1 M acetic acid and ethanol/water (20%, v/v). The substance obtained was stored at 4° C. in 10 mL of ethanol/water (20%, v/v) until usage.

(Cell Glycomics by Using BLOTGLYCOABC™ Beads)

Cell culture: The PC-3 cell of human prostate cancer and the cell (PrEC) of normal human prostate epithelial were respectively obtained from Health Science Researches Bank and Cambrex Bio Science Walkersville, Inc. (Walkersville, Md.). The PC-3 cell was kept in Ham's F-12 replenishing 10% bovine embryo serum, 50 U/ml of penicillin and 50 µg/mL of streptomycin. The PrEC cell was maintained according to the illustration of the producer using Clonetics Prostate Epithelial Growth Media (PrEGM™) BULLETKIT® kit. These cells were cultured at 37° C. and 5% $CO_2$ in a humidifying incubator.

Preparation of N-glycan from cells: Cells proliferated in a 10 cm dish were washed with ice bath PBS, scraped off in PBS containing 10 mM EDTA, and then washed with PBS. Cells collected in a 1.5 ml tube were suspended in PBS (60 µl), dissolved by adding ⅒ by volume of 10% Triton X-100 and left still standing on the ice for 1 hour. This lysate was subjected to centrifugation at 15,000 rpm at 4° C. for 10 min. To this supernatant was added 4 by volume cold acetone to cause precipitation of protein substances and left overnight at −20° C. Precipitates were collected by centrifugation at 12,000 rpm, 4° C. for 15 minutes; their pellets were washed with 200 µl of acetonitrile and subjected to centrifugation as mentioned above. These pellets were dissolved in 50 µl of 80 mM ammonium hydrogen carbonate (including 0.02% 1-propanesulfonic acid, 2-hydroxy-3-lauric amide (PHL)), and incubated at 60° C. for 10 minutes. To this solution was added 1 µl of 0.5M dithiothreitol (DTT) aqueous solution, incubated at 60° C. for 30 minutes, and then alkylated with iodoacetamide by incubating at room temperature for 30 minutes under light shielded condition. Subsequently, this mixture was treated with trypsin overnight at 37° C. and heat inactivated at 90° C. for 10 minutes. After cooled down to room temperature, this mixture was incubated overnight at 37° C. together with 2.5 U of PNGase F (Roche). Prepared substance (20-40 µl) equivalent to cells per ½ culture dish was used in the following Glycoblotting protocol that uses BLOTGLYCOABC™ beads as described in this specification.

(Automation of Glycoblotting Protocol that Uses BLOTGLYCOABC™ Beads)

Using 8 wells of filter plate, equivalent volume (20 µl) of PNGase F digestion blood serum sample was applied to BLOTGLYCOABC™ beads, and Glycoblotting protocol was executed simultaneously according to the flow diagram shown in FIG. 8. N-glycan thus collected was analyzed by MALDI-TOFMS and detected area was statistically analyzed.

(Discussion)

Recent development of mass spectrometry brought new difficult problem in Glycomics. As this difficult problem, development of rapid glycan enrichment technology is mentioned. Easy technology for retrieval of biomarkers related to carbohydrate is important. This is because the proteomics research targets glycation that is a posttranslational modification. In this specification, the present inventors report "all-in-one" type protocol for high-throughput clinical Glycomics. With this novel technology, glycan concentration of Glycoblotting base on BLOTGLYCOABC™ beads, stabilization on sialic acid beads, and fluorescent labeling of oligosaccharide are unified into one workflow on the multi-well filter plate. Advantages of this protocol and MALDI-TOF mass analysis were verified through distinction of serum N-glycan profile of specimen having congenital glycation disorder, serum N-glycan profile of specimen having hepatocellular cancer, and serum N-glycan profile of a healthy donor. Further, above-mentioned method enabled whole cell Glycomics of human prostate cancer cell and normal human prostate epidermal cell. These results suggest possibility of glycan condensation/treatment for biomarker discovery.

Large-scale quantitative Glycomics is important and encouraging approach. This is because a difference of glycan expression between disorder state and healthy state is expected to be favorable tool for diagnosis of the disorder or prognostic judgment (Hakomori, S. (2001) Adv. Exp. Med. Biol. 491, 369-402.). At present, mass spectrometry (MS) is used exclusively for structure analysis of carbohydrate and study of sequence determination (Zaia, J. (2004) Mass Spectrom. Rev. 23, 161-227.; Dell, A., and Morris, H. R. (2001) Science 291, 2351-2356.). Due to remarkable improvements in MS technology (ionization, fragmentation and detection method are cited) (Kurogochi, M., and Nishimura, S. (2004) Anal. Chem. 76, 6097-6101.; Takegawa, Y., Deguchi, K., Ito, S., Yoshioka, S., Nakagawa, H., and Nishimura, S. (2005)

Anal. Chem. 77, 2097-2106.; Takegawa, Y., Deguchi, K., Ito, S., Yoshioka, S., Nakagawa, H., and Nishimura, S. (2005) Anal. Chem. 77, 2097-2106.), MS is more preferable in glycomics than other analysis methods (e.g., high pressure liquid chromatography (HPLC) and nuclear magnetic resonance analysis (NMR). Specifically, moderate ionization of glycan and matrix support laser desorption ionization-time-of-flight (MALDI-TOF) MS for delivery of high-throughput analysis, and electrospray ionization (ESI) MS are potential candidates for primary technology.

However, PCR-like glycan amplification technology for glycomics is not available. Because glycan biosynthesis process is not template driven type, but is provided for multiple, continuous and enzyme processes. Although partial peptide fragment detected in proteomics is completely supported by full length protein sequence database/full length DNA sequence database, condensation of total glycan from highly combined mixture (e.g., serum, cell and texture) is necessary for glycomics. Therefore, one of significant bottlenecks in structure-function glycomics is tiresome and time-consuming multiple processes for glycan purification. For example, after once being separated from glycoproteins or glycolipids, glycan is frequently subjected to fluorescent labeling and purification for detection in HPLC analysis (Neville, D. C., Coquard, V., Priestman, D. A., to Vruchte, D. J., Sillence, D. J., Dwek, R. A., Platt, F. M., and Butters, T. D. (2004) Anal. Biochem. 331, 275-282.; Tomiya, N., Kurono, M., Ishihara, H., Tejima, S., Endo, S., Arata, Y., and Takahashi, N. (1987) Anal. Biochem. 163, 489-499.). In addition, oligosaccharide containing sialic acid is further modified for stabilization and amplification of sensitivity of anionic glycan in MS measurement (Powell, A. K., and Harvey, D. J. (1996) Rapid Commun. Mass Spectrom. 10, 1027-1032.; Sekiya, S., Wada, Y., and Tanaka, K. (2005) Anal. Chem. 77, 4962-4968.; Mechref, Y., Kang, P., and Novotny, M. V. (2006) Rapid Commun. Mass Spectrom. 20, 1381-1389.). In several cases, although important information are lost, sialic acid is removed due to simplification or limitation of detection. In recent years, DNA sequence determination is also used for clinical N-glycan profiling (Callewaert, N., VanVlierberghe, H., Van Hecke, A., Laroy, W., Delanghe, J., and Contreras, R. (2004) Nat. Med. 10, 429-434.; Laroy, W., Contreras, R., and Callewaert, N. (2006) Nat. Protoc. 1, 397-405.). In this clinical N-glycan profiling, multiple processes and derivation procedures as mentioned above suited for capillary electrophoresis are still necessary. In general, the protocol for preparation of glycan derivatives varies depending on the analysis method and needs expertise for handling in every process. Due to these technical but significant problems in glycan condensation, it is not possible to accomplish reliable high-throughput glycomics (Morelle, W., Canis, K., Chirat, F., Faid, V. and Michalski, J. C. (2006) Proteomics 6, 3993-401.).

Recent efforts by the inventors were directed to practical glycan condensation method (i.e., Glycoblotting) (Nishimura, S., Niikura, K., Kurogochi, M., Matsushita, T., Fumoto, M., Hinou, H., Kamitani, R., Nakagawa, H., Deguchi, K., Miura, N., Monde, K., and Kondo, H. (2005) Angew. Chem. Int. Ed. Engl. 44, 91-96.; Lohse, A., Martins, R., Jorgensen, M. R., and Hindsgaul, O. (2006) Solid-phase oligosaccharide tagging (SPOT): Validation on glycolipid-derived structures. Angew. Chem. Int. Ed. Engl. 45, 4167-4172.; Niikura, K., Kamitani, R., Kurogochi, M., Uematsu, R., Shinohara, Y., Nakagawa, H., Deguchi, K., Monde, K., Kondo, H., and Nishimura, S. (2005) Chem. Eur. J. 11, 3825-3834.; Shimaoka, H., Kuramoto, H., Furukawa, J., Miura, Y., Kurogochi, M., Kita, Y., Hinou, H., Shinohara, Y., and Nishimura, S. (2007) Chem. Eur. J. 13, 1664-1673.; Miura, Y., Shinohara, Y., Furukawa, J. I., Nagahori, N., and Nishimura, S. I. (2007) Chem. Eur. J. 13, 4797-4804; Kita, Y., Miura, Y., Furukawa, J. I., Nakano, M., Shinohara, Y., Ohno, M., Takimoto, A., and Nishimura, S. I. (2007) Mol. Cell. Proteomics 6, 1437-1445.). The optimum protocol for this needs only 5 µl of human serum for quantitative profiling of 30 to 40 types of primary glycoform in 5 to 8 hours (Miura, Y., Shinohara, Y., Furukawa, J. I., Nagahori, N., and Nishimura, S. I. (2007) Chem. Eur. J. 13, 4797-4804.). These attempts clearly showed such advantages that higher recovery is attained and complicated manipulations are reduced by incorporating a solid supporter in easy and efficient manipulations of condensed glycan. The present inventors present in this specification "all-in-one" type solution for automated high-throughput N-glycan condensation treatment. This solution is very beneficial in "real world" clinical glycomics. With this system, multiple processes (e.g., selective capture of whole glycan, methyl esterification of sialic acid and fluorescent tagging) can be unified in one workflow based on the use of the combination of handling of hydrazide functionalized beads and multi-way filter plate. The present inventors consider that with this de facto standard technology, large-scale clinical glycomics/large-scale clinical glycoproteomics will be made possible and discovery of novel disease-related biomarkers will be accelerated.

(Conclusions)

Much research for verification of changes in glycosylation of proteins by disease state has been reported (Baldus, S. E., Wienand, J. R., Werner, J. P., Landsberg, S., Drebber, U., Hanisch, F. G., and Dienes, H. P. (2005) Int. J. Oncol. 27, 1289-1297.; Comunale, M. A., Lowman, M., Long, R. E., Krakover, J., Philip, R., Seeholzer, S., Evans, A. A., Hann, H. W., Block, T. M., and Mehta, A. S. (2006) J. Proteome Res. 5, 308-315.; Dwek, M. V., Lacey, H. A., and Leathem, A. J. (1998) Clin. Chim. Acta 271, 191-202.; J. Proteome Res. 6, 1822-1832.). The results of the inventors show potential clinical value of quantitative analysis of whole serum N-glycan profile obtained by MALDI-TOFMS. In recent years, usability of MALDI-TOFMS for profiling of N-glycan in the serum is expected in both quantitative analysis and qualitative analysis for promotion of clinically related detection of a tumor (Morelle, W., Flahaut, C., Michalski, J. C., Louvet, A., Mathurin, P., and Klein, A. (2006) Glycobiology 16, 281-293.; Kranz, C., Ng, B. G., Sun, L., Sharma, V., Eklund, E. A., Miura, Y., Ungar, D., Lupashin, V., Winkel, D. R., Cipollo, J. F., Costello, C. E., Loh, E., Hong, W., and Freeze, H. H. (2007) Hum. Mol. Genet. 16, 731-741.). The method by the inventors imparts very high feasibility of glycan condensation and derivatization for quantitative and exhaustive MS analysis in the clinical evaluation. By incorporating integrated type Glycoblotting beads (BLOTGLYCOABC™ beads introduced here) and methyl esterification on the bead, true gross N-glycomics analysis was made possible. The present protocol needed only 2.5 µl of aliquot of human whole serum and performed multiple processes for subsequent derivatization successfully on the solid phase by single sweeping by manipulations (including MALDI-TOFMS) for four hours. This resulted in drastic improvements in efficiency and time for manipulation. Since meaningful improvements were verified in preparation and analysis of the serum glycan, the protocol proposed by the inventors could be used for glycan concentration analysis from cell sample. For human prostate cancer PC-3 cell being proliferated in a single 10 cm dish and for normal cell corresponding thereto, the inventors have preliminarily verified their overall cell N-glycome by means of Glycoblotting using BLOTGLYCO-ABC™ beads and MALDI-TOFMS analysis. The cell glycome profiling method was essentially identical with the serum glycome profiling method except for small modifications made prior to pretreatment of the sample (FIG. 13). The present results clearly showed that there was a significant difference in structure of N-glycan (pattern and volumes of N-glycan) between PC-3 cells and normal prostate epidermal cells (PrEC). It is considered that use of the approach which the inventors proposed will greatly promote glycomics at cell level and tissue level. Recent finding about defect that results in each CDG identified that glycan analysis is insufficient to point out correctly a defect in part of CDG-II (Wu, X., Steet, R. A., Bohorov, O., Bakker, J., Newell, J., Krieger, M., Spaapen, L., Kornfeld, S., and Freeze, H. H. (2004) Nat. Med. 10, 518-523.; Redner, R. A., and Walker, H. F. (1984) Soc. Indust. Appl. Math. Rev. 26, 195-239.). However, although multiple tests could not be performed for each of the subtypes, the present results clearly verified that the dataset about the abundance of N-glycan in patients of each subtype was definitely separated at places of expression by principal component analysis. Therefore, in general screening tests (e.g., newborn screening program), discovery of a rare case may become essential by quantitative glycomics for CDG. This is because CDG could be detected together with other disorders by a simple blood examination. The present Glycoblotting technique could then become a method for realizing the above due to its reproducibility and easiness. It is interesting if this technique is applied to other disorders (e.g., congenital galactosemia and chronic alcohol intake) characterized by alteration of glycosylation of transferrin to identify usability of the analysis performed in this research.

It is now possible to identify a set of specific N-glycan expression ratios best suited for pattern classification by statistical approach based on N-glycan profiling by large-scale glycomics (83 patients and 20-healthy donors) of HCC sample. The inventors distinguished HCC samples and the normal control with as high as 100% accuracy by the specific N-glycan profile mentioned above. Therefore, information obtained by the present study, while still requiring verification using correlation with other clinical variables and medical facts such as hepatitis B virus infection and/or C hepatitis C virus infection, quantitative profiling of the selected glycoform has potential clinical information for a novel and effective diagnosis biomarker for human HCC.

Mass spectrometry with reproducibility over entire MALDI-TOFMS analysis was realized by quantitative methyl esterification of sialic acid residue. This will allow MALDI-TOFMS to be capable of withstanding simultaneous and quantitative profiling for neutral N-glycan and acidic N-glycan. Even if there are such advantages which are better than other analysis methods, it was necessary to note the fact that intensity of mass signal is frequently dependent on individual MALDI device used during analysis on N-glycan with broad range molecular weight. It seems that this is attributable to the laser source mounted to each of MALDI systems and is influenced by ionization efficiency of particular molecule (e.g., high molecular weight glycan having plural sialic acid residues). By comparison of the present results (Table 4) and previous data (Kita, Y., Miura, Y., Furukawa, J. I., Nakano, M., Shinohara, Y., Ohno, M., Takimoto, A., and Nishimura, S. I. (2007) Mol. Cell. Proteomics 6, 1437-1445.), it was assumed that glycan amount of triantennary added thoroughly to sialic acid is reduced from the amount in the previous data.

(Table 5) Statistics of automation trial of human serum N-glycan condensation/treatment (n=8)
Peak area was normalized with regard to 2045 m/z.

TABLE 5

| Peak No | m/z | Normal (μM) | | CDG-Ia (μM) | | | CDG-Ib (μM) | | |
|---|---|---|---|---|---|---|---|---|---|
| | | Average | std | Average | std | P | Average | Std | P |
| 0 | 1333.460 | N.D. | 0.00 | 1.35 | 0.13 | 2.9E−10 | 1.16 | 0.11 | 1.4E−10 |
| 1 | 1495.511 | 2.70 | 0.41 | 2.48 | 0.34 | 1.3E+00 | 1.66 | 0.18 | 2.0E−04 |
| 2 | 1520.543 | N.D. | 0.00 | N.D. | 0.00 | NaN | N.D. | 0.00 | NaN |
| 3 | 1536.538 | N.D. | 0.00 | N.D. | 0.00 | NaN | N.D. | 0.00 | NaN |
| 4 | 1577.565 | 0.00 | 0.00 | 0.00 | 0.00 | NaN | 0.72 | 0.57 | 1.1E−02 |
| 5 | 1657.564 | 2.78 | 0.47 | 1.70 | 0.26 | 5.7E−04 | 0.48 | 0.54 | 1.3E−05 |
| 6 | 1723.623 | 74.56 | 6.86 | 16.52 | 2.11 | 2.3E−09 | 27.95 | 2.30 | 2.1E−08 |
| 7 | 1739.617 | 2.20 | 0.20 | 0.47 | 0.52 | 1.8E−05 | 2.48 | 0.34 | 1.1E−01 |
| 8 | 1780.644 | N.D. | 0.00 | N.D. | 0.00 | NaN | N.D. | 0.00 | NaN |
| 9 | 1819.617 | N.D. | 0.00 | N.D. | 0.00 | NaN | N.D. | 0.00 | NaN |
| 10 | 1841.649 | 2.05 | 0.39 | 2.00 | 0.33 | 8.5E−01 | 1.49 | 0.74 | 1.4E−01 |
| 11 | 1885.675 | 119.55 | 9.29 | 35.08 | 3.99 | 1.7E−09 | 49.15 | 3.04 | 7.3E−09 |
| 12 | 1901.670 | 3.24 | 0.28 | 1.96 | 0.20 | 3.3E−06 | 3.01 | 0.32 | 2.2E−01 |
| 13 | 1928.702 | 8.53 | 1.41 | 3.25 | 0.69 | 9.2E−08 | 3.85 | 0.45 | 1.5E−05 |
| 14 | 1942.697 | 1.15 | 1.34 | N.D. | 0.00 | 6.2E−02 | N.D. | 0.00 | 6.2E−02 |
| 15 | 1981.670 | 0.29 | 0.71 | N.D. | 0.00 | 3.4E−01 | N.D. | 0.00 | 3.4E−01 |
| 16 | 1997.707 | 0.51 | 0.81 | N.D. | 0.00 | 1.5E−01 | N.D. | 0.00 | 1.5E−01 |
| 17 | 2003.702 | 1.97 | 1.07 | 0.48 | 0.74 | 1.9E−02 | 0.27 | 0.66 | 7.8E−03 |
| 18 | 2044.729 | 2.52 | 1.29 | N.D. | 0.00 | 7.2E−04 | 0.62 | 0.97 | 1.6E−02 |
| 19 | 2047.728 | 31.61 | 2.76 | 15.38 | 2.12 | 4.6E−07 | 20.30 | 1.70 | 6.6E−06 |
| 20 | 2088.755 | 11.27 | 1.28 | 3.20 | 0.51 | 5.4E−08 | 3.29 | 0.34 | 4.1E−08 |
| 21 | 2104.750 | 0.23 | 0.56 | N.D. | 0.00 | 3.4E−01 | N.D. | 0.00 | 3.4E−01 |
| 22 | 2143.723 | 1.38 | 0.71 | N.D. | 0.00 | 7.6E−04 | N.D. | 0.00 | 7.6E−04 |
| 23 | 2185.755 | 0.22 | 0.55 | 0.83 | 0.67 | 1.2E−01 | 1.65 | 0.26 | 1.8E−04 |
| 24 | 2206.781 | 87.58 | 3.93 | 38.09 | 3.55 | 5.8E−10 | 48.20 | 2.68 | 1.9E−09 |
| 25 | 2247.808 | 1.05 | 1.72 | N.D. | 0.00 | 1.7E−01 | N.D. | 0.00 | 1.7E−01 |
| 26 | 2250.808 | 5.38 | 1.00 | 3.20 | 0.59 | 1.0E−03 | 1.82 | 1.50 | 7.0E−04 |
| 27 | 2266.802 | 1.94 | 0.34 | 0.36 | 0.56 | 1.6E−04 | 0.32 | 0.54 | 9.8E−05 |
| 28 | 2352.839 | 31.91 | 2.18 | 25.07 | 2.65 | 8.7E−04 | 12.12 | 0.94 | 1.7E−09 |
| 29 | 2393.866 | 0.31 | 0.75 | N.D. | 0.00 | 3.4E−01 | N.D. | 0.00 | 3.4E−01 |
| 30 | 2409.861 | 1.11 | 1.23 | N.D. | 0.00 | 5.1E−02 | N.D. | 0.00 | 5.1E−02 |
| 31 | 2412.860 | N.D. | 0.00 | N.D. | 0.00 | NaN | 0.16 | 0.40 | 3.4E−01 |
| 32 | 2469.882 | 3.23 | 0.77 | 1.54 | 0.51 | 1.0E+00 | 2.59 | 1.03 | 2.5E−01 |
| 33 | 2481.893 | 320.00 | 0.00 | 320.00 | 0.00 | NaN | 320.00 | 0.00 | NaN |

TABLE 5-continued

| Peak No | m/z | Normal (µM) | | CDG-Ia (µM) | | | CDG-Ib (µM) | | |
|---|---|---|---|---|---|---|---|---|---|
| | | Average | std | Average | std | P | Average | Std | P |
| 34 | 2511.892 | 542.12 | 16.82 | 364.28 | 8.78 | 5.6E−10 | 160.46 | 13.29 | 3.0E−06 |
| 35 | 2539.924 | 5.17 | 0.77 | 2.51 | 1.47 | 2.8E−03 | 3.71 | 0.88 | 1.2E−02 |
| 36 | 2555.919 | 15.77 | 1.62 | 7.08 | 1.11 | 6.8E−07 | 3.11 | 0.71 | 7.2E−09 |
| 37 | 2571.914 | 19.93 | 0.96 | 11.66 | 5.89 | 6.8E−03 | 14.73 | 1.75 | 7.9E−05 |
| 38 | 2615.940 | 1.25 | 1.38 | 0.80 | 0.89 | 5.1E−01 | 0.98 | 1.09 | 7.1E−01 |
| 39 | 2631.935 | 0.55 | 0.86 | 1.35 | 0.67 | 1.0E−01 | 1.25 | 1.01 | 2.2E−01 |
| 40 | 2657.950 | 11.74 | 1.11 | 16.63 | 1.73 | 1.7E−04 | 15.14 | 1.41 | 9.3E−04 |
| 41 | 2717.971 | 10.20 | 0.30 | 11.88 | 1.22 | 8.2E−03 | 9.40 | 1.06 | 1.0E−01 |
| 42 | 2861.030 | 4.21 | 0.60 | 1.55 | 0.88 | 1.6E−04 | N.D. | 0.00 | 9.3E−09 |
| 43 | 2877.025 | 0.52 | 0.80 | 1.47 | 0.75 | 5.8E−02 | 1.09 | 0.56 | 1.6E−01 |
| 44 | 3023.083 | 0.53 | 0.60 | 1.93 | 0.32 | 4.7E−04 | N.D. | 0.00 | 5.6E−02 |
| 45 | 3182.136 | 1.67 | 0.35 | 3.66 | 0.43 | 4.9E−06 | 1.20 | 0.67 | 1.6E−01 |
| total (µM) | | 1013.05 | 68.45 | 576.52 | 44.57 | | 693.22 | 41.92 | |

N.D,; Not detected in the specimen
NaN; Nonnumerio

These results are attributable to both differences of chemical structure between high-sensitivity tag of peptide base (Kita, Y., Miura, Y., Furukawa, J. I., Nakano, M., Shinohara, Y., Ohno, M., Takimoto, A., and Nishimura, S. I. (2007) Mol. Cell. Proteomics 6, 1437-1445.) and the probe designated by BLOTGLYCOABC™ beads, and of the output and wavelength of the laser used in each measurement. To accomplish more accurate and reliable quantitative analysis in the glycomics of MALDI mass spectrometry base, it is likely that a new type of molecular probe with higher ionization efficiency, which provides such high molecular weight glycan, should be developed. For plural serum samples and cell samples, integrated type Glycoblotting technique utilizing BLOTGLYCOABC™ beads greatly facilitates discovery of novel biomarkers for various disorders. Chemical properties used for handling of enriched N-glycan in the solid phase are well suited for the derivatization needed in the subsequent analysis method and therefore, recovered N-glycan tagged with an optimum chemical probe can be used for conventional HPLC, LC-MS and/or analysis of DNA sequencer base.

Example 2

Example of type H

In the present example, analysis example using type H is exemplified. Essentially, the experiments performed under the conditions stated in Example 1. FIG. 1 exemplify the analysis example diagrammatically. In particular, the following steps are performed. Preparation of beads of BLOTGLYCOH™ are carried out in accordance with Example 1 (synthesis of beads of BLOTGLYCOABC™ and characterization) using ABC and descriptions of Japanese Patent Application No. 2006-217165 and Japanese Patent Application No. 2006-73170.

A) A sugar chain separation step for separating a sugar chain in a sample comprising the steps of:
  A-1) providing 10 µl of serum which is the sample to PCR plate;
  A-2-1) adding 45 µl of 1-propane sulfonic acid, 2-hydroxy-3-lauric amide (PHL) or 2-hydroxy-3-myristamide (PHM) 0.26%/bicarbonate of ammonium 0.11 M to the sample (CV 5%) to cause reaction at 37° C. for 10 minutes; or
  A-2-2) adding 50 µl of 1-propane sulfonic acid, 2-hydroxy-3-lauric amide (PHL) or 2-hydroxy-3-myristamide (PHM) 0.24%/bicarbonate of ammonium 105 mM/dithiothreitol (DTT) 12 mM to the sample (CV 56). When A-2-1) is employed in the above,
  A-3-1) adding 5 µl of 120 mM dithiothreitol (DTT) (CV 56) to the sample.

When A-2-2) is employed in the above or upon completion of above A-3-1),
  A-3-2) adding 12 µl of A2 amide sugar chain that is an internal standard (peak No. 33 in above Table 3), to cause reaction at 60° C. for 30 minutes and then cooling to room temperature.
  A-4) adding 10 µl of 123 mM iodoacetamide (IAA) (CV 5%) to the sample to cause reaction at room temperature and in dark place for 1 hour.
  A-5) adding 5 µl of trypsin 400 U to the sample to cause reaction at 37° C. for 60 minutes.
  A-6) heating the sample at 90° C. for 10 minutes and then cooling to room temperature, wherein cooling is performed sufficiently to avoid deactivation of PNGaseF.
  A-7) adding 5 µl of PNGaseF2U to cause reaction at 37° C. for 12 hours, wherein care is taken so that solvent evaporation may not occur during operation while corresponding to ceiling by heating treatment.

B) Step for preparation of detection sample for detection of the sugar chain being separated:
  B-1) contacting the capture sugar sample prepared in step A) with beads for sugar capture and causing binding at 80° C. to prepare a capture sugar sample, wherein 180 µl of 2% acetic acid/acetonitrile is added, heat is kept at 80° C. for 45 minutes, and washed.
  B-2) adding 200 µl of 2M guanidine hydrochloride twice to the captured sugar chain as necessary, placing the captured sugar chain sample under the reaction condition and then discharging reaction liquid by suction.
  B-3) washing 200 µl of the captured sugar sample twice with water as necessary and then discarding the water by suction.
  B-4) washing 200 µl of the captured sugar sample twice with trimethylamine/methanol and then discarding the trimethylamine by suction, wherein after suction, bottom wiping is performed in a sheet with cotton.
  B-5) adding 100 µl of 10% acetic anhydride/methanol to the captured sugar chain sample, placing the captured sugar chain sample under the reaction conditions of room temperature for 30 minutes and then discarding the acetic anhydride by suction, wherein methanol is added to acetic anhydride to prepare 10% acetic anhydride/methanol.

B-6) adding 200 µl of 10 mM hydrochloric acid to the captured sugar chain sample twice as necessary and discarding the hydrochloric acid by suction.

B-7) adding 200 µl of methanol to the captured sugar chain sample twice as necessary, adding 200 µl of dioxane to the captured sugar chain sample twice as necessary after the methanol is discarded by suction, and discarding by suction.

B-8) performing bottom wiping in a sheet with cotton.

B-9) adding 100 µl 100 mM methyl-p-tolyl-triazene (MTT)/dioxane to the captured sugar chain sample to cause reaction at 80° C. for 60 minutes.

B-10) adding 200 µl of dioxane to the captured sugar chain sample and discarding the dioxane by suction.

B-11) (1) adding 200 µl of methanol to the captured sugar chain sample, discarding by suction; (2) adding 200 µl of a 20 mM NaCl solution to captured sugar chain sample, discarding by suction; (3) washing the captured sugar chain sample with 200 µl of water and discarding the water by suction.

B-12) adding 180 µl of 2% acetic acid/acetonitrile to the captured sugar chain sample, tagging sugar chain in the captured sugar chain sample using 20 µl of 20-50 mM aminooxy tryptophanyl arginine methyl ester/water, O-benzylhydroxylamine hydrochloride/water or anthraniloyl hydrazine/water and discarding by suction.

B-13) adding 100 µl of water to the captured sugar chain sample being tagged to produce tagged sugar chain solution.

C) Step for producing mass spectrometry plate on which the captured sugar chain samples being tagged are deposited:

C-1) disposing tagged sugar chain sample solution obtained in step B) on the collection plate.

C-2) adding 15 µl of a 50% methanol/1% glycerol aqueous solution that is liquid matrix to the plate for mixing.

C-3) adding 15 µl of the tagged sugar chain sample from the plate for collection to plate for mixing, mixing by pipette to cause ignition.

Mass spectrometry plate is generated from this by dispensing 2 µl and depositing on MALDI Plate (#209512 MTP Anchor Chip™ 400/384 T F (384 anchors, 400 µm diameter; #209520 MTP 384 target plate polished steel T F, Bruker Daltonik GmbH).

D) executing MALDI-TOF according to the ordinary method.

The present invention has been exemplified as mentioned above using preferred embodiments of the present invention. However, it should be understood that the scope of the present invention is interpreted only by the claims. It should be understood that contents of patents, patent applications and literatures cited in the specification are incorporated herein for reference of the present specification.

INDUSTRIAL APPLICABILITY

The inventors succeeded in providing an automatic analysis device for analyzing sugar chains contained in the sample such as serum sample. This enabled analysis of a large quantity of samples simultaneously and automatically. For separation of sugar chains quantitatively from sugar proteins, complicated pre-treatments such as reduction alkylation and trypsin digestion as well as solubilizing agent were automated. For sugar chains being quantitatively isolated, although prompt analysis of sugar chains is possible while removal of troublesome foreign matters are made easy by performing chemoselective capture, this invention enabled one-time treatment of many specimen samples. Each of the steps above were optimized and a system capable of coping with automatic analysis was constructed.

Analysis of multiple specimens is made possible by the device of the present invention. Searching of sugar chain biomarkers is expected, and applications concerning diagnosis and early diagnosis of diseases are considered.

BRIEF DESCRIPTION OF DRAWINGS

FIG. 6 is a continuation of FIG. 5;

FIG. 7 is an exemplary flow chart for the dispensing in the process making use of BLOTGLYCOABC™ beads;

FIG. 8 is different from FIG. 1 in that a reduction treatment of hydrazone bond using a 8 M borane-pyridine complex is further included in FIG. 8. Such a treatment can be carried out by referring to Angew Chem Int Ed Engl. 2006 Jun. 19; 45(25):4167-72; Lohse A, Martins R, Jorgensen MR, Hindsgaul O, et al. The descriptions for the various numerals are described in the section of EXPLANATIONS OF LETTERS OR NUMERALS or in the specification;

FIG. 8C is a magnified view (upper middle part) of FIG. 8.

FIG. 10b is a diagram showing a stable hydrazide-functionalized polymer carrier (that is, BLOTGLYCO-ABC™ beads) prepared by designing N-(2-aminobenzoyl) cysteine hydrazide (ABCh), a multifunctional molecular probe, and binding this probe to thiopropyl-Sepharose 6B. This is a general protocol for the integrated glycoblotting technology. (a) Workflow of glycoblotting-based high-throughput clinical glycomics. The process includes the following: 1) a reduced sugar is chemoselectively captured onto hybridized functionalized beads using the glycoblotting technology 15, 2) washing is performed to remove all of the impurities, 3) the sialic acid residue is subjected to on-bead methyl esterification, and then the hydrazone bond is reduced, 4) modified N-glycan is recovered by reducing the disulfide bond. (b) Glycoblotting based on BLOTGLYCO-ABC™ beads. The chemical structure of N-(2-aminobenzoyl)cysteine hydrazide (ABCh), the probe, is included; reference may be made to the descriptions in the specification with respect to the synthesis;

EXPLANATIONS OF REFERENCE NUMERALS

Figure 1:
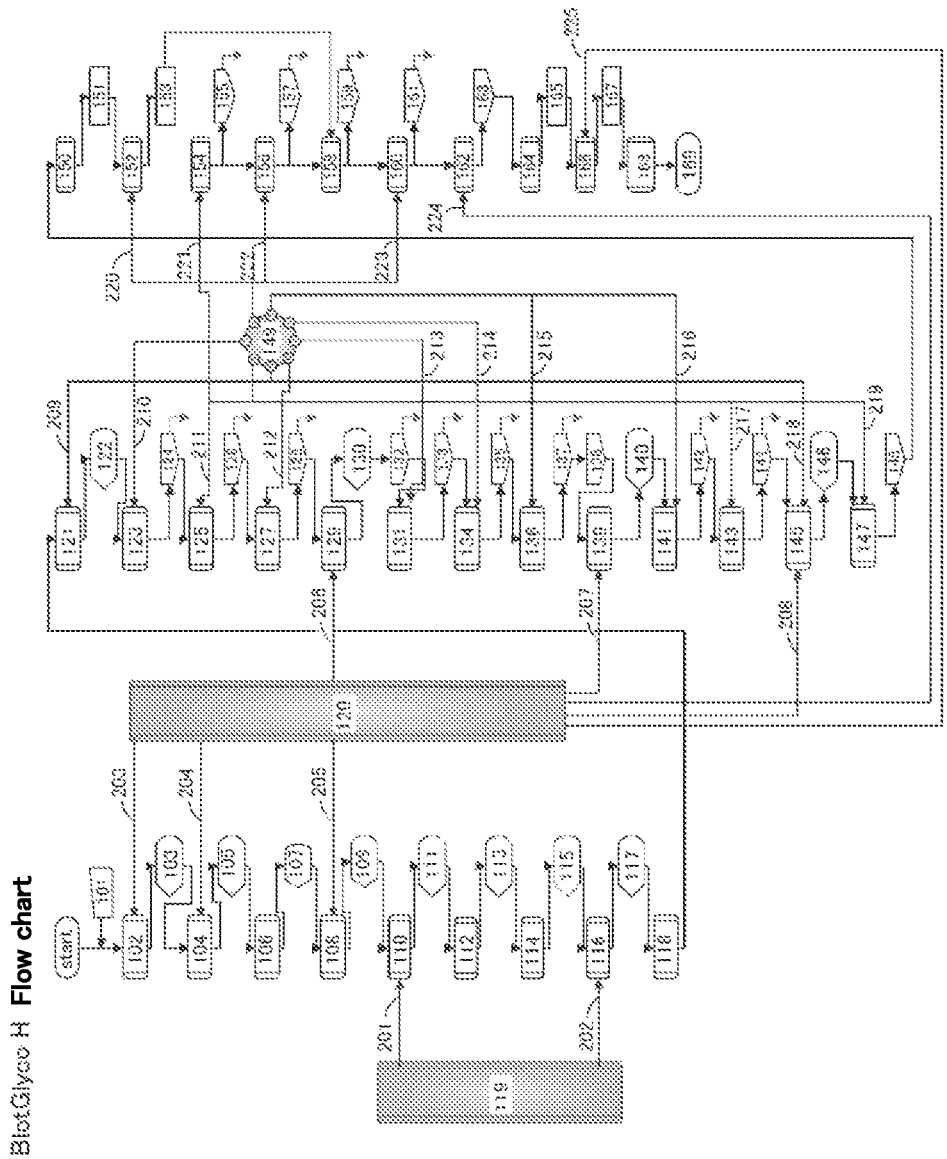
FIG. 1 is the flow chart for BLOTGLYCOH™ beads, which is a representative embodiment of the sugar chain auto-analyzing apparatus or the pretreatment apparatus for sugar chain auto-analysis of the present invention. Descriptions for the respective numerals are described in the section of EXPLANATIONS OF LETTERS OR NUMERALS or in the specification.
Figure 1A:
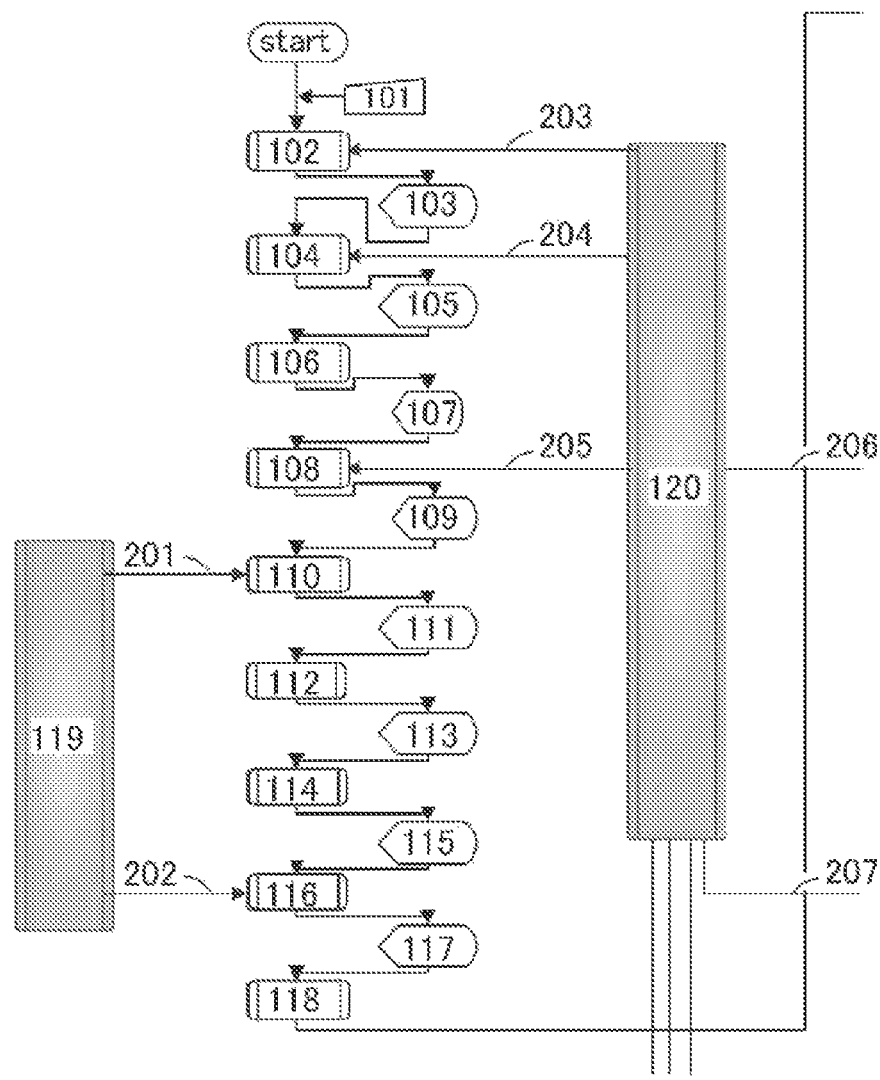
FIG. 1A is a magnified view (upper left part) of FIG. 1.
Figure 1B:
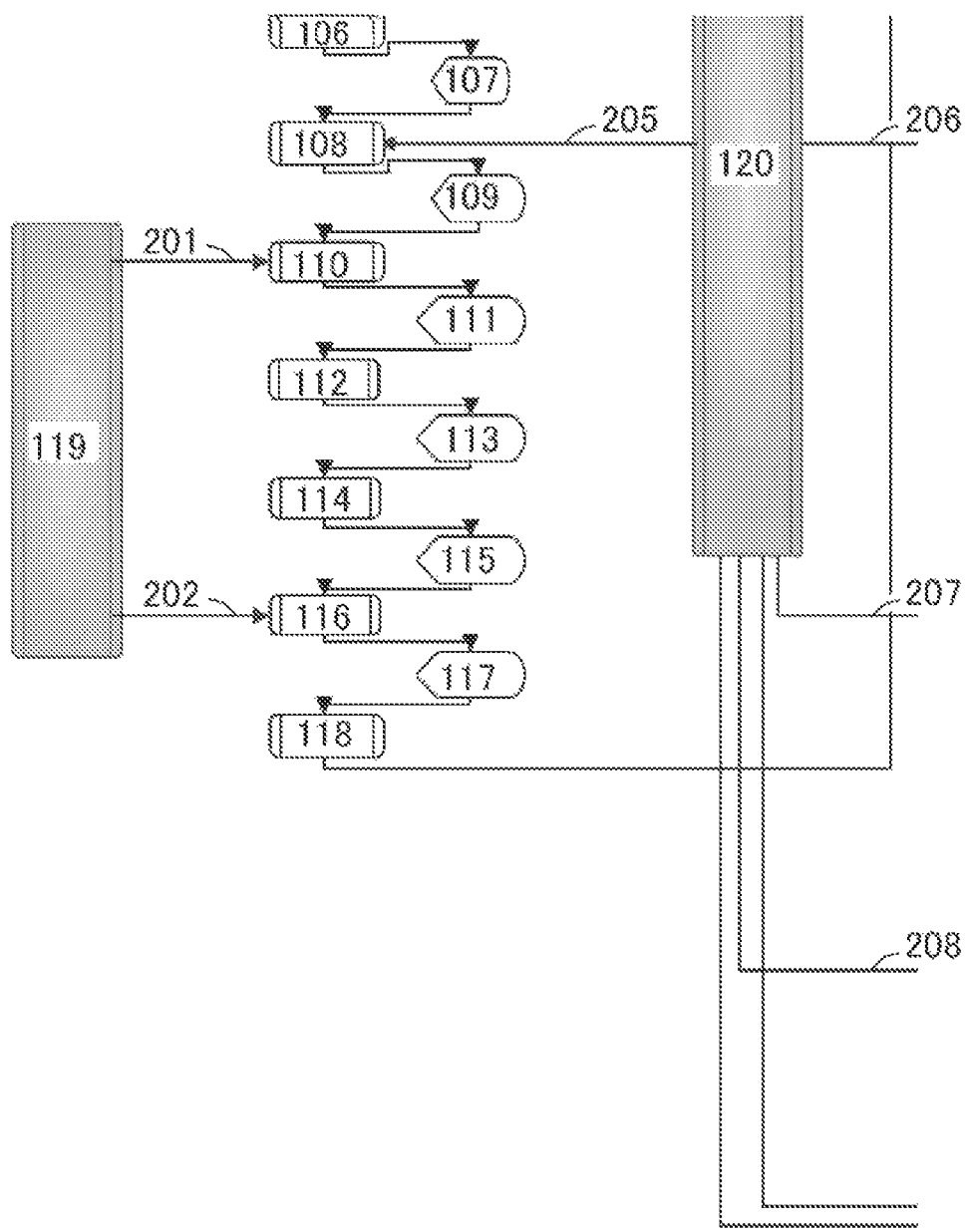
FIG. 1B is a magnified view (lower left part) of FIG. 1.
Figure 1C:
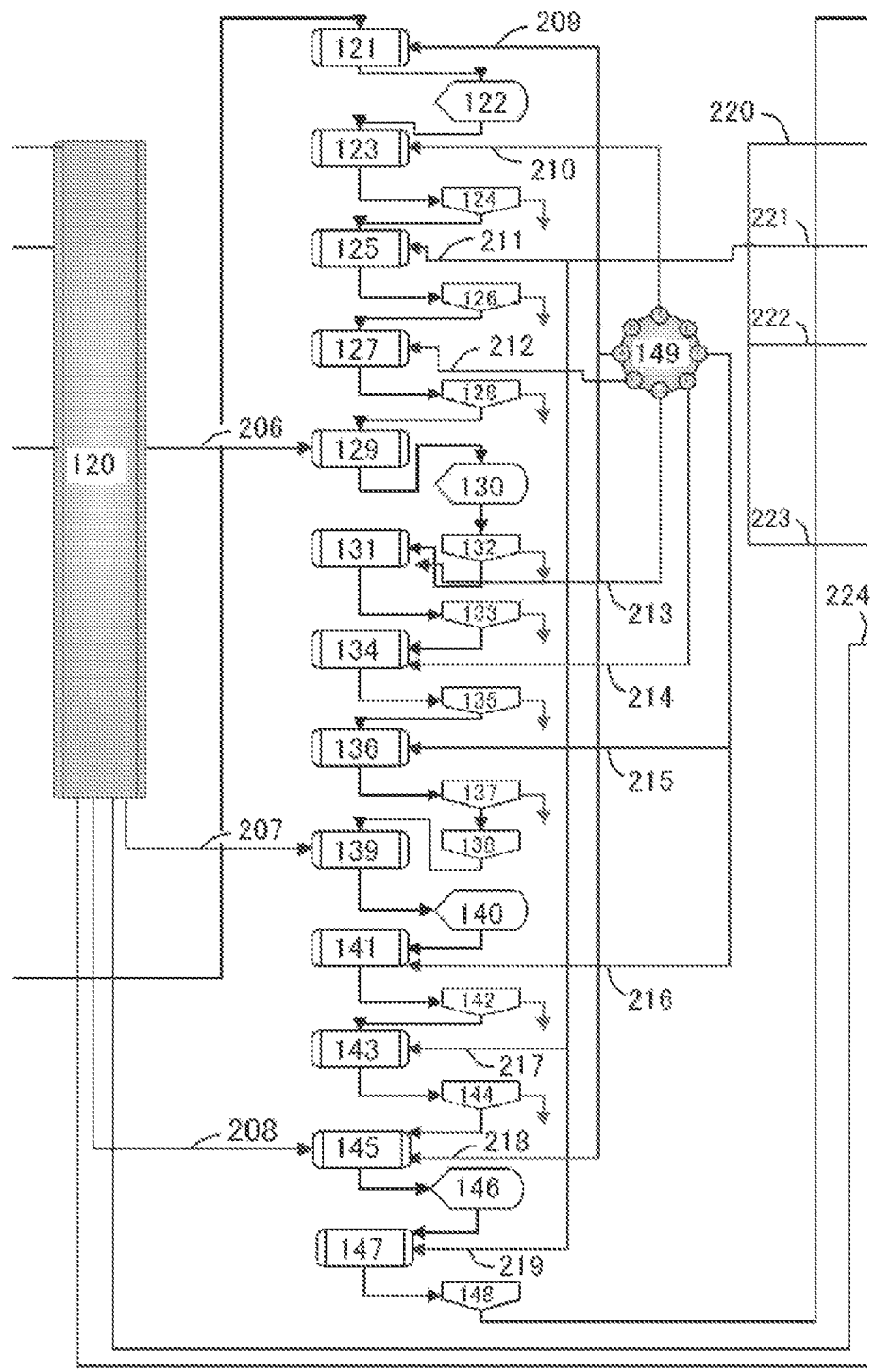
FIG. 1C is a magnified view (upper middle part) of FIG. 1.
Figure 1D:
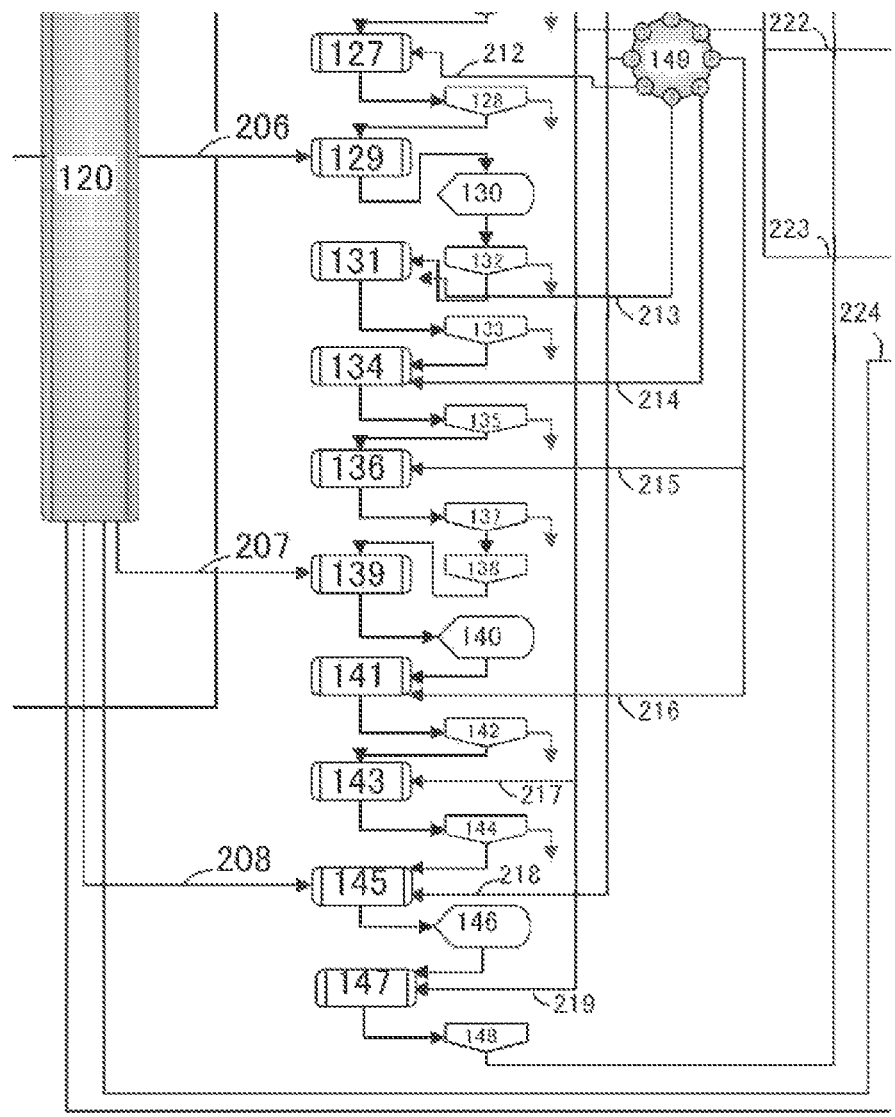
FIG. 1D is a magnified view (lower middle part) of FIG. 1.
Figure 1E:
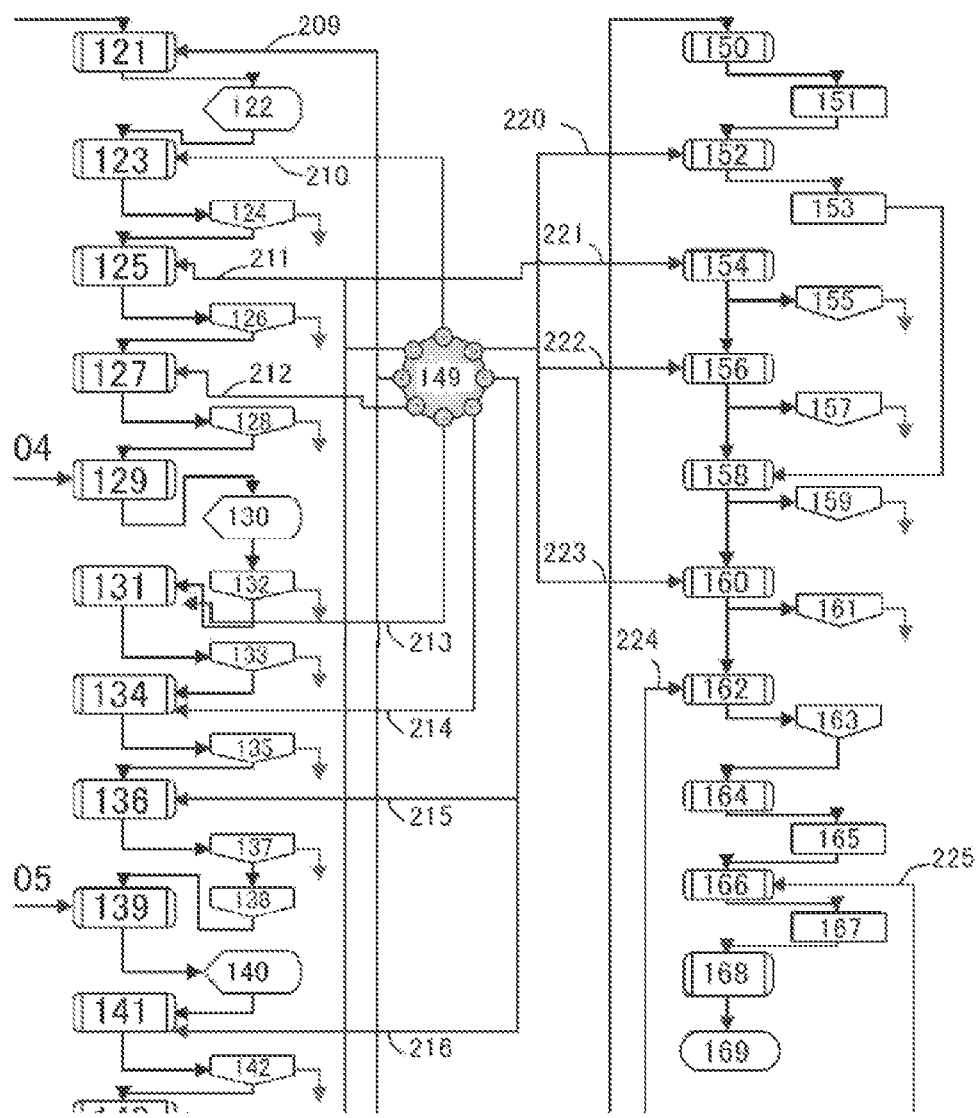
FIG. 1E is a magnified view (upper right part) of FIG. 1.
Figure 1F:
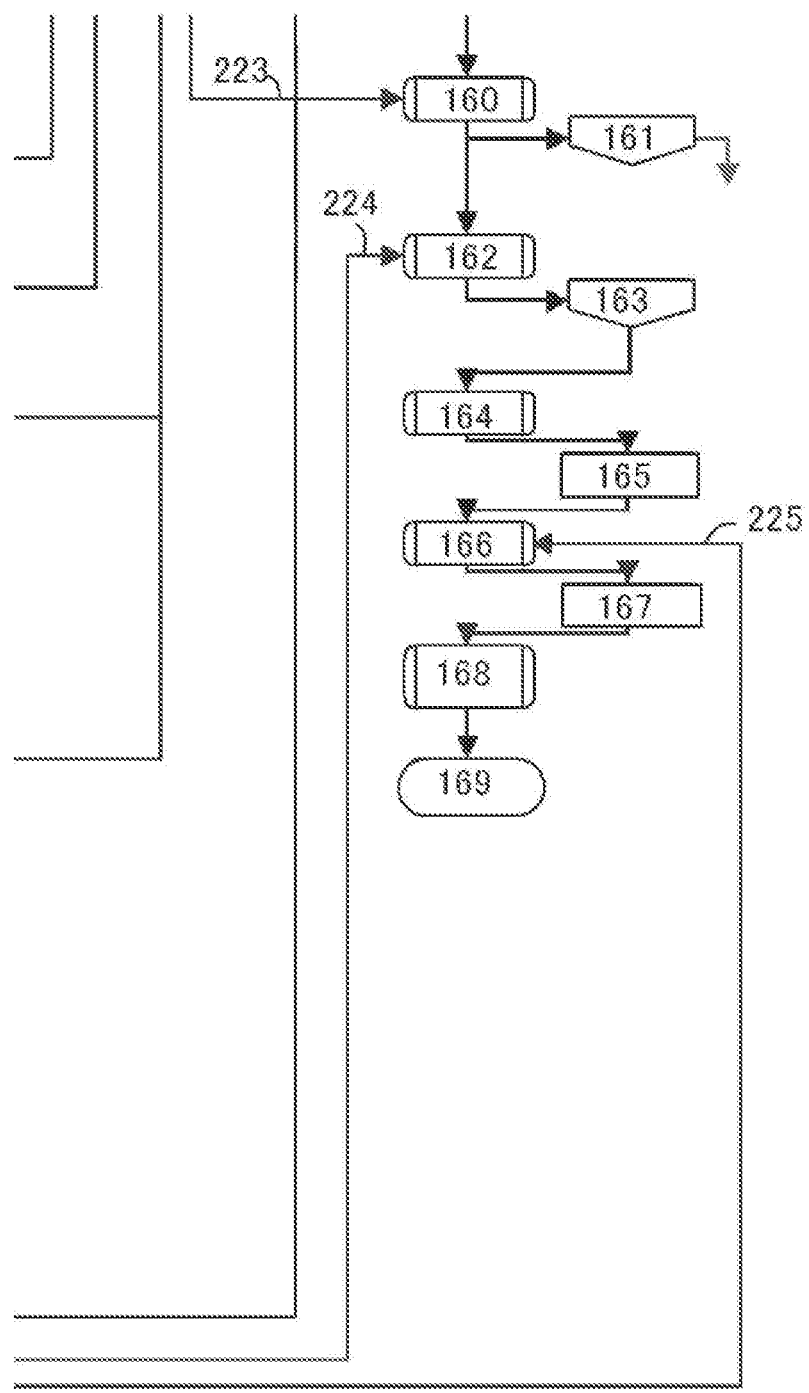
FIG. 1F is a magnified view (lower right part) of FIG. 1.
Figure 2:
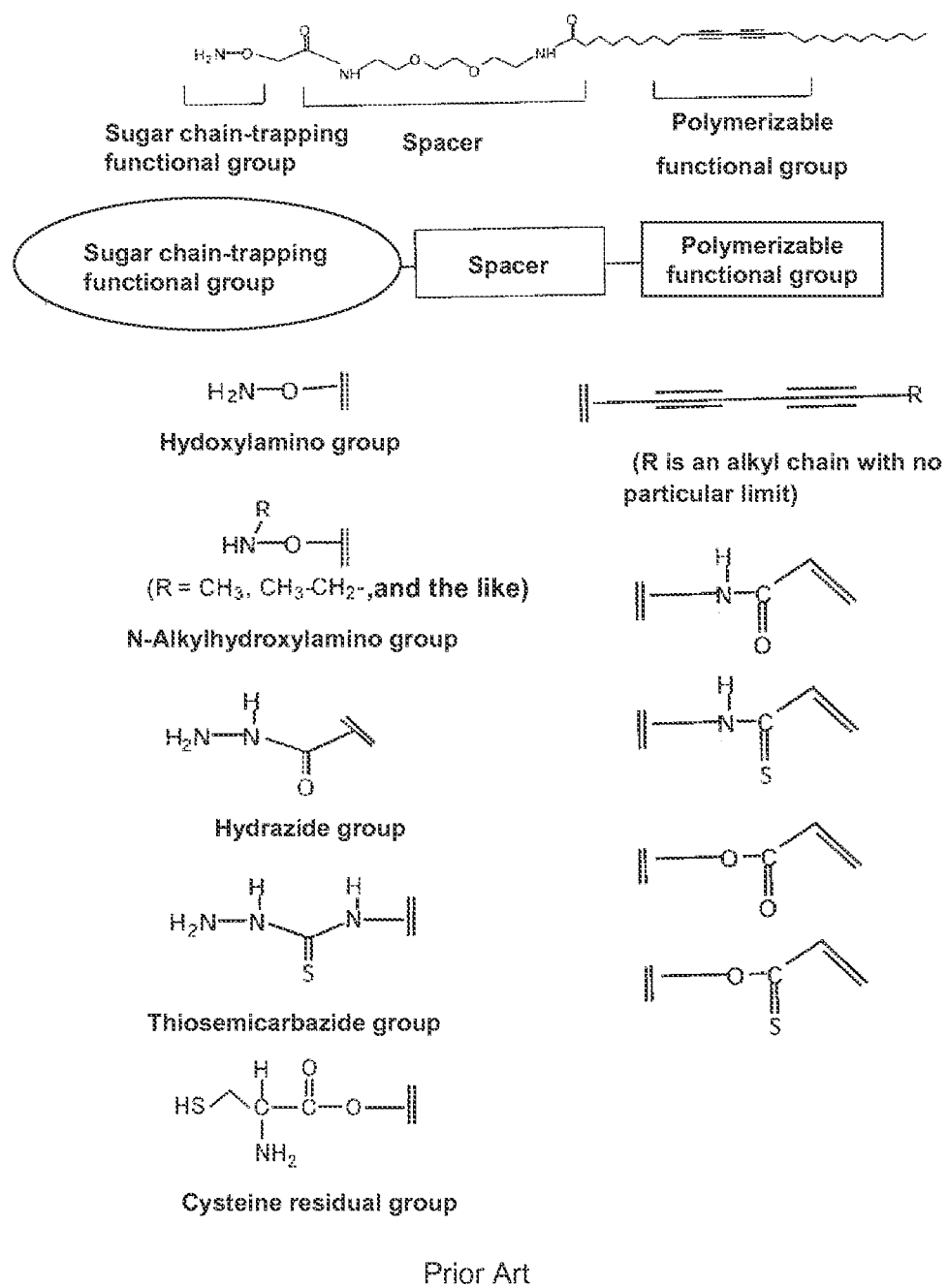
FIG. 2 is a schematic diagram of a sugar chain-capturing molecule.
Figure 3:
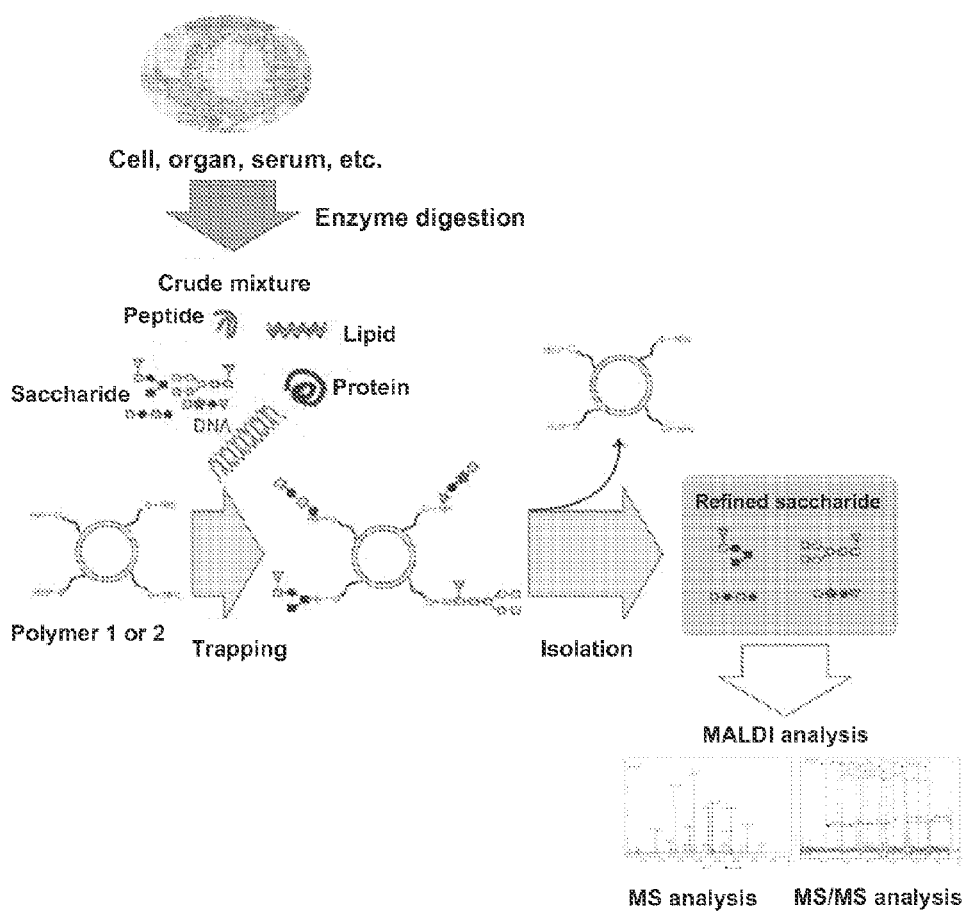
FIG. 3 is a conceptual diagram of sugar chain blotting. Since a sugar chain released from a complex carbohydrate such as a glycoprotein, a proteoglycan or a glycolipid, necessarily has a hemiacetal group equivalent to an aldehyde group at a reduced terminus in the molecule, complete chemical discrimination from other biological molecules such as the amino acid/peptide constituting a protein, the nucleotide constituting DNA/RNA, and lipids, is realized by a selective nucleophilic addition reaction specific to this hemiacetal group. Various substances (regardless of being a macromolecule or a small molecule) containing a functional group capable of generally reacting with reduced termini of all kinds of sugar chains (an aminooxy group, a hydrazide group or the like) are used to conduct sugar chain capturing, probe labeling using a highly sensitive reagent or the like, and a structural analysis according to those mass spectrometric methods, continuously at high speed. The MADLI analysis, MS analysis and MS/MS analysis results shown in the lower right corner are given as examples.
Figure 4:
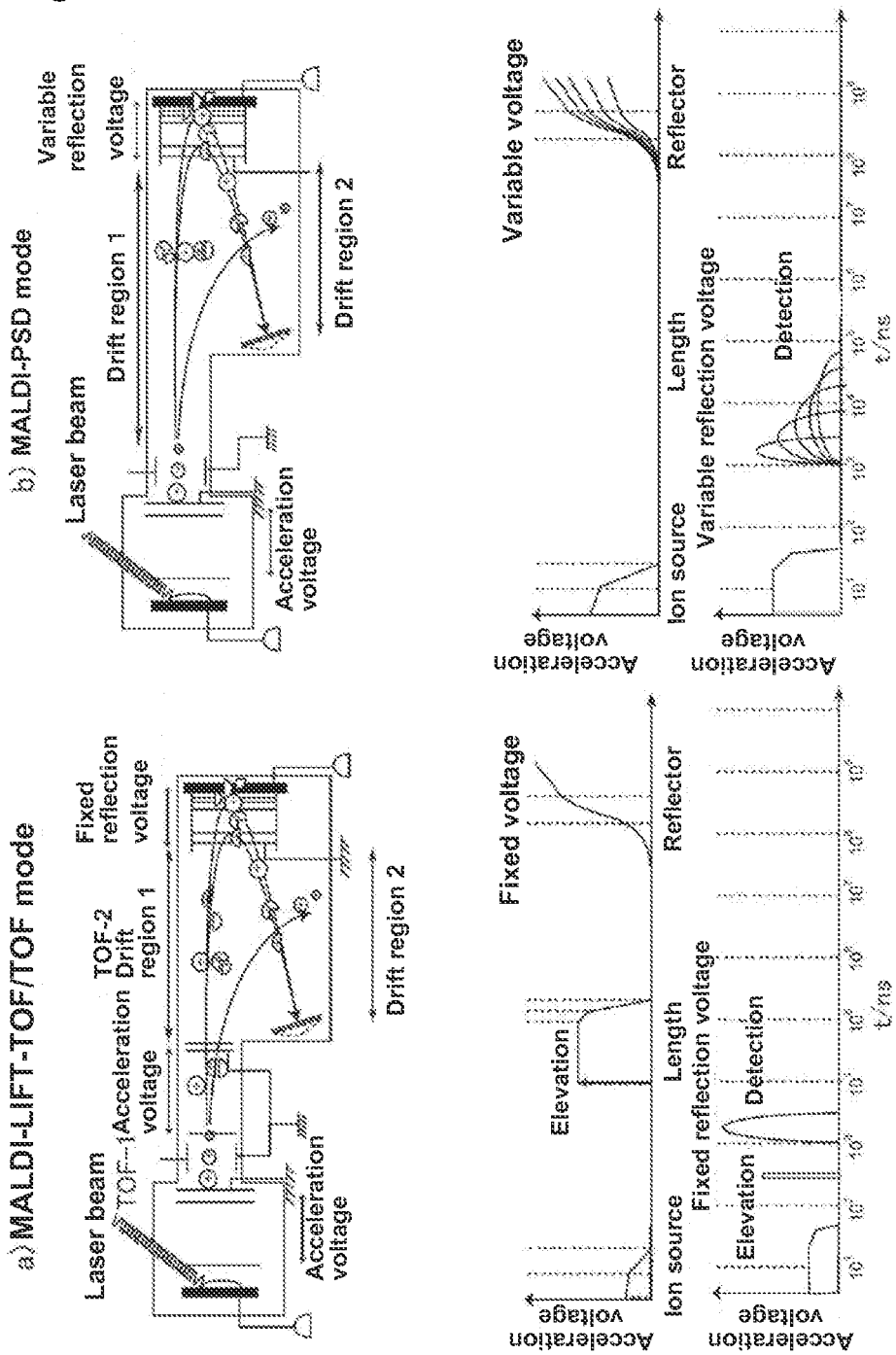
FIG. 4 is a diagram showing the fundamental principles of MALDI-TOF MS.
Figure 5:
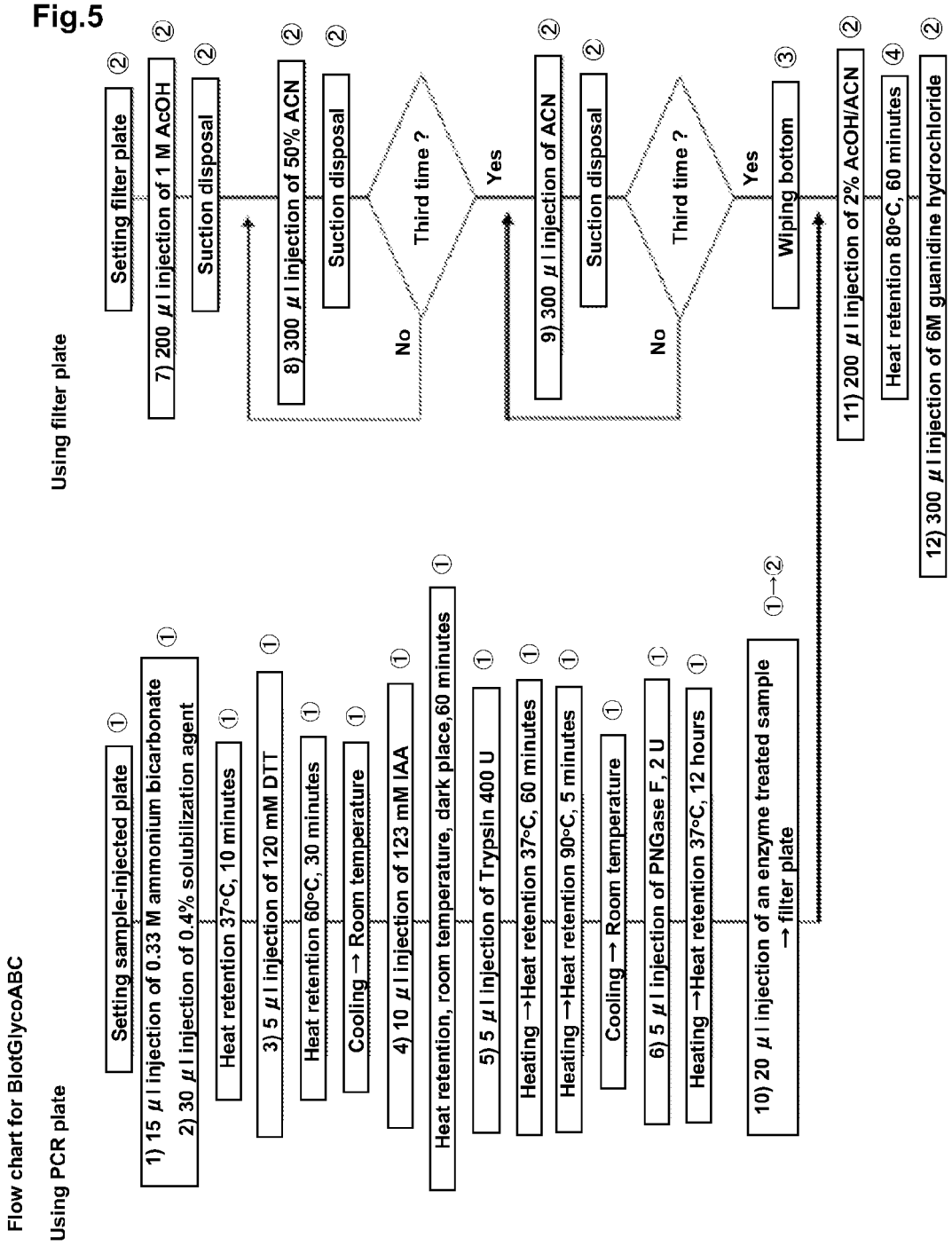
FIG. 5 is an exemplary flow chart of a process making use of BLOTGLYCOABC™ beads.
Figure 6:
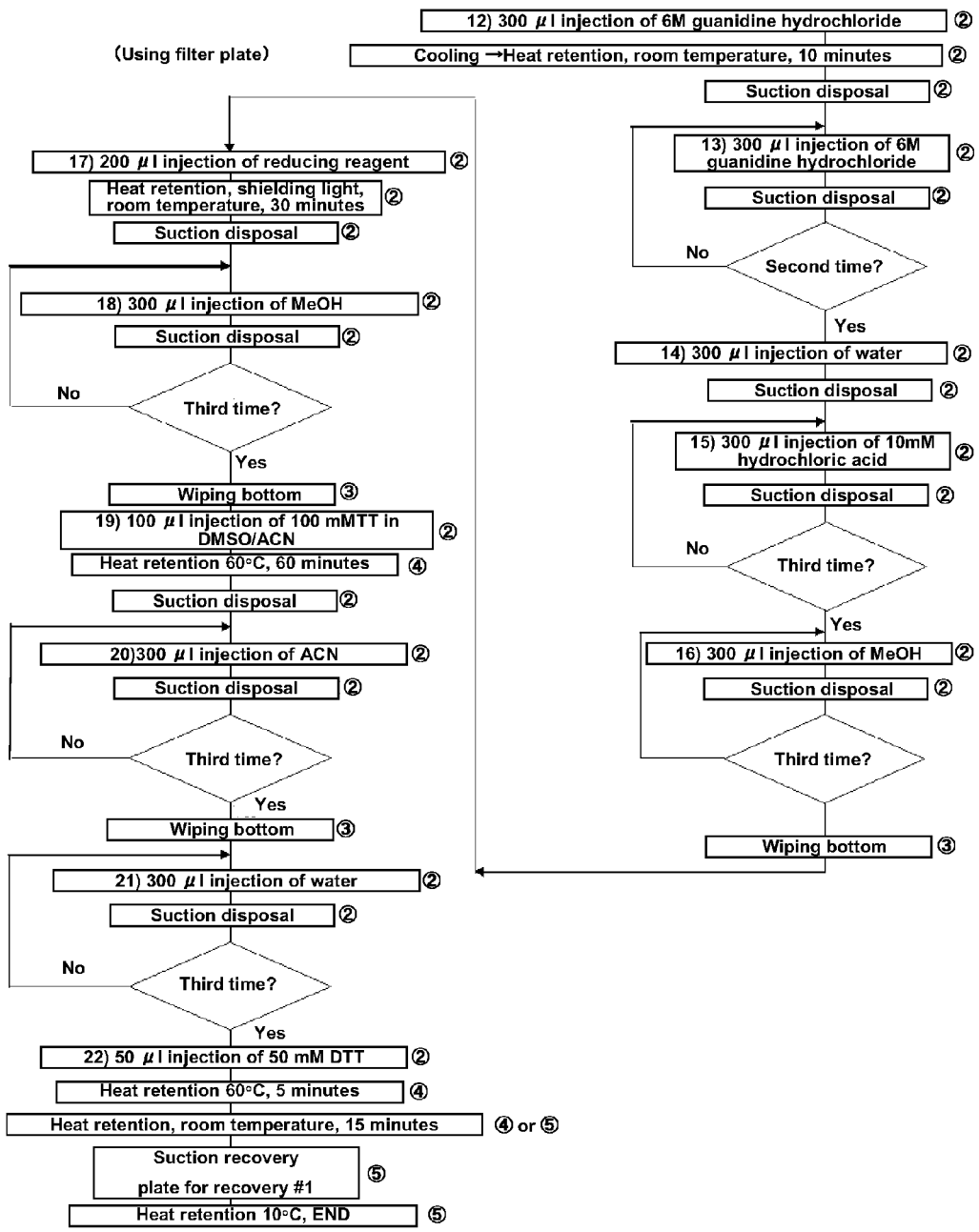
FIG. 6 is an exemplary flow chart of a process making use of BLOTGLYCOABC™ beads.
Figure 8:
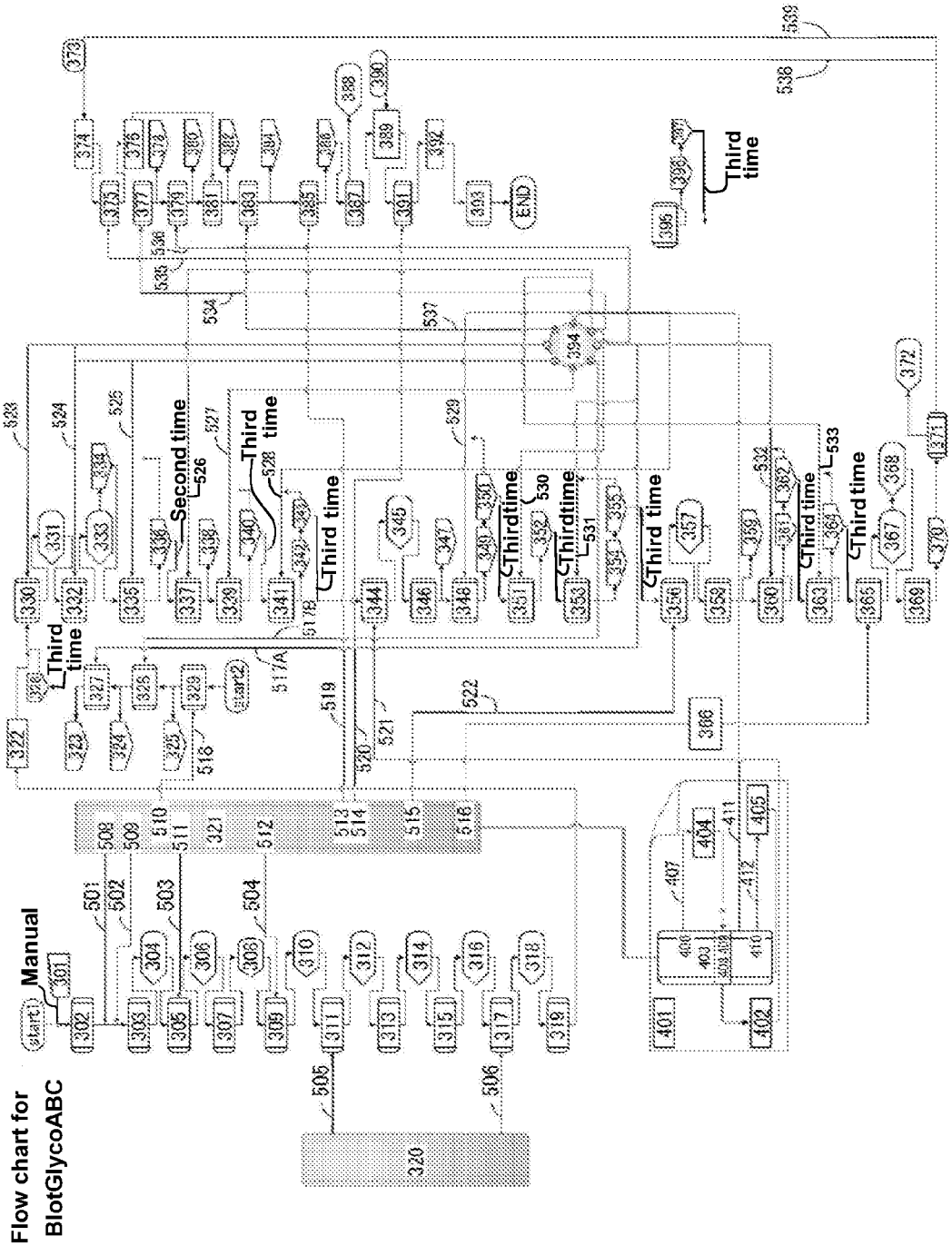
FIG. 8 is an exemplary bird's-eye view of a process making use of BLOTGLYCOABC™ beads. A flow diagram of the automated glycoblotting protocol is shown. Application to a 96-well format robot is shown.
Figure 8A:
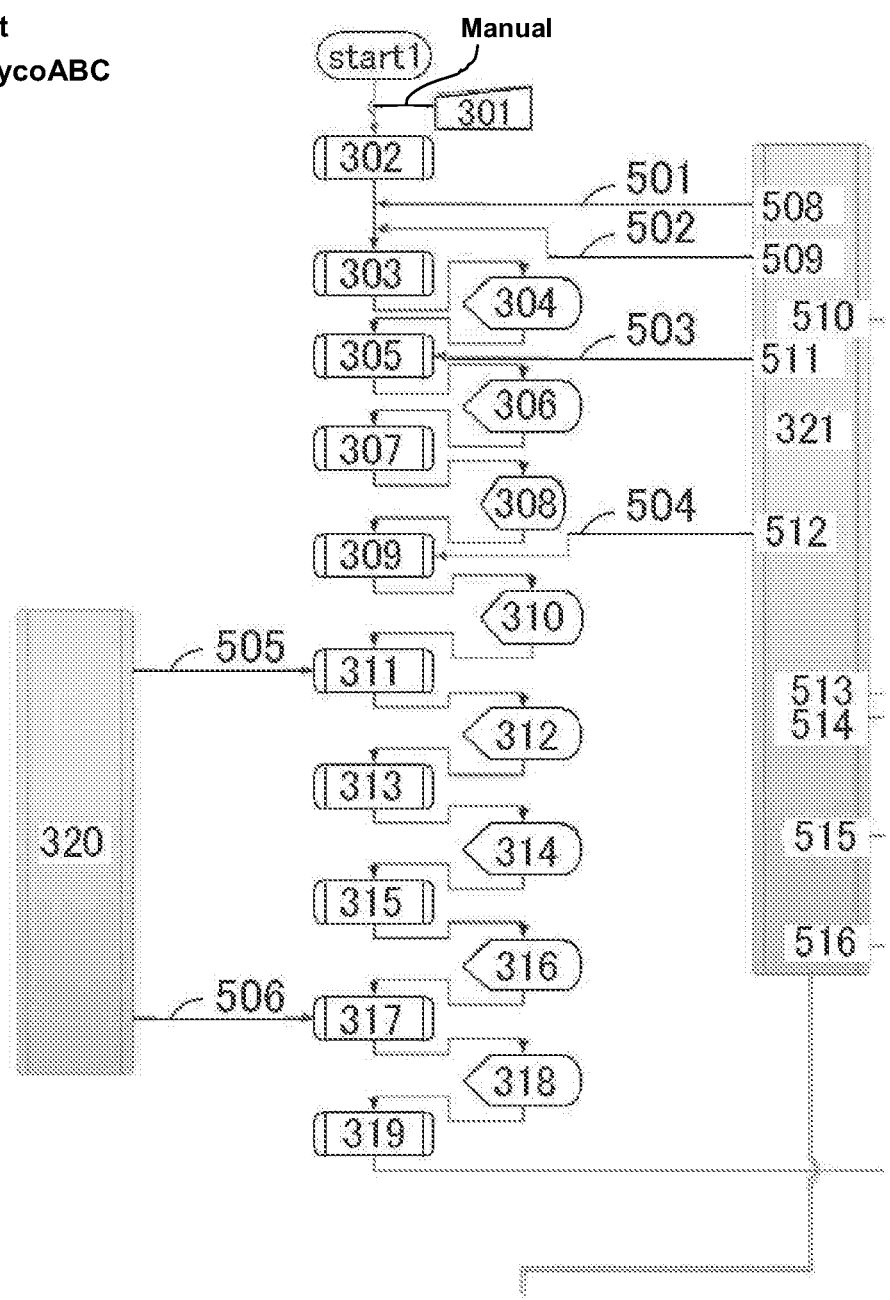
FIG. 8A is a magnified view (upper left part) of FIG. 8.
Figure 8B:
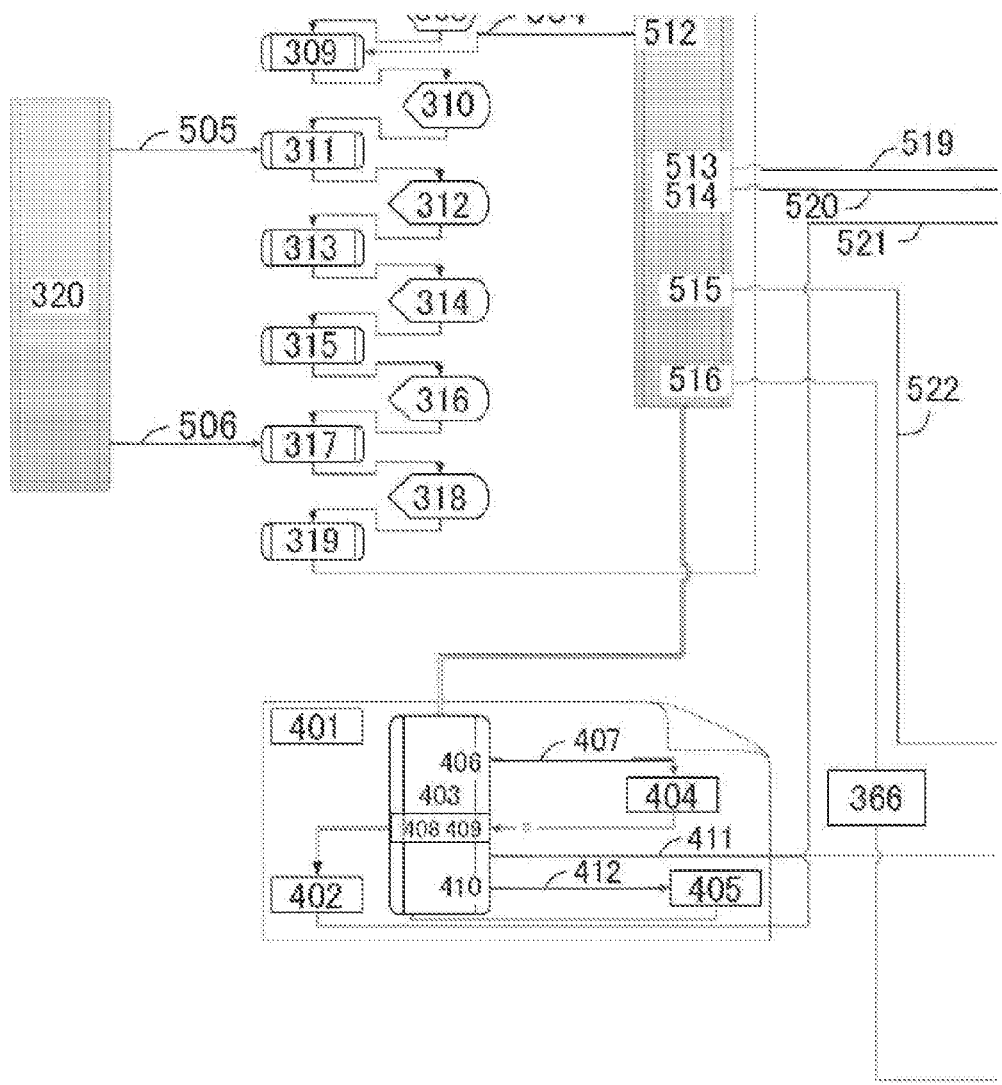
FIG. 8B is a magnified view (lower left part) of FIG. 8.
Figure 8D:
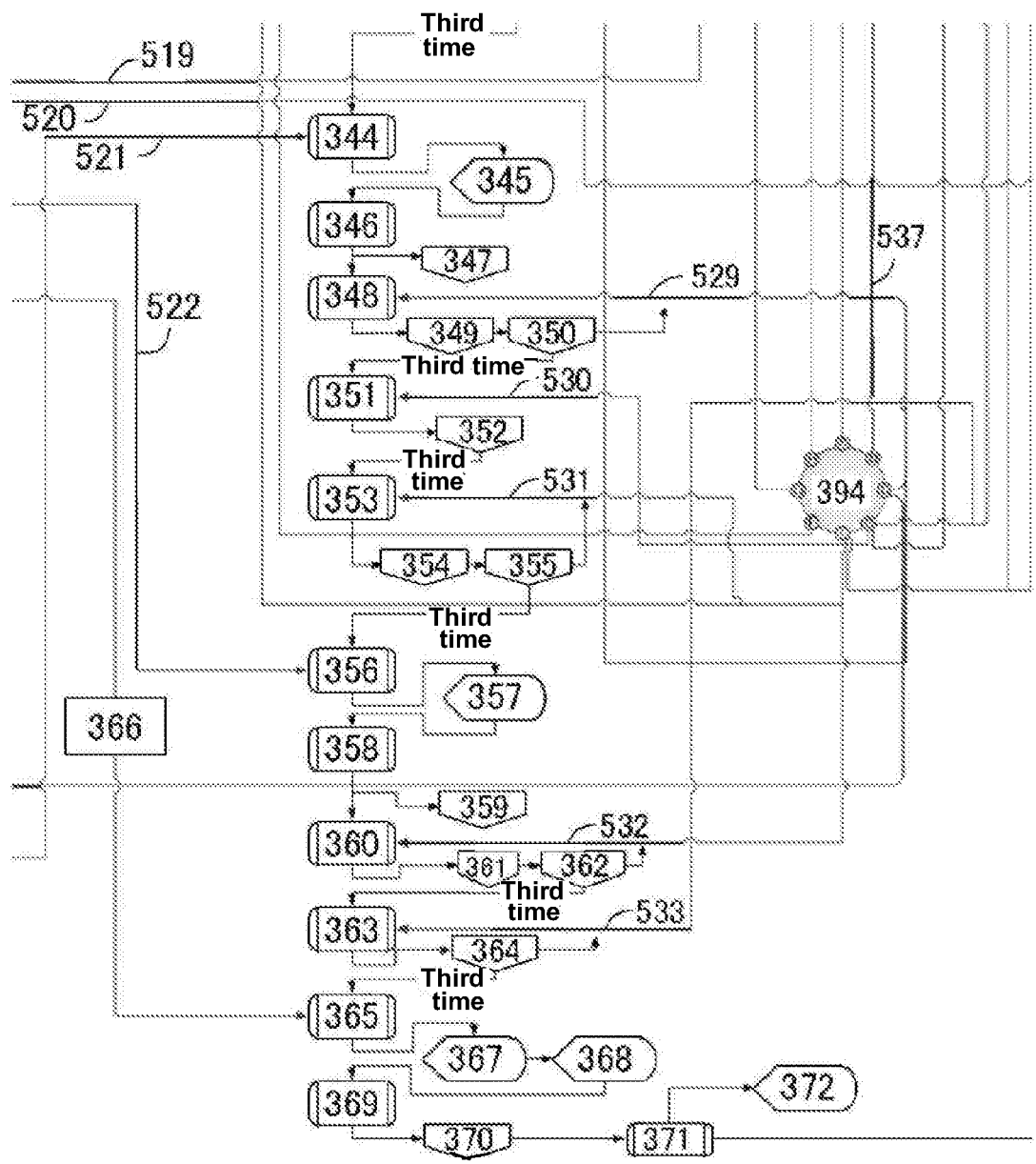
FIG. 8D is a magnified view (lower middle part) of FIG. 8.
Figure 8E:
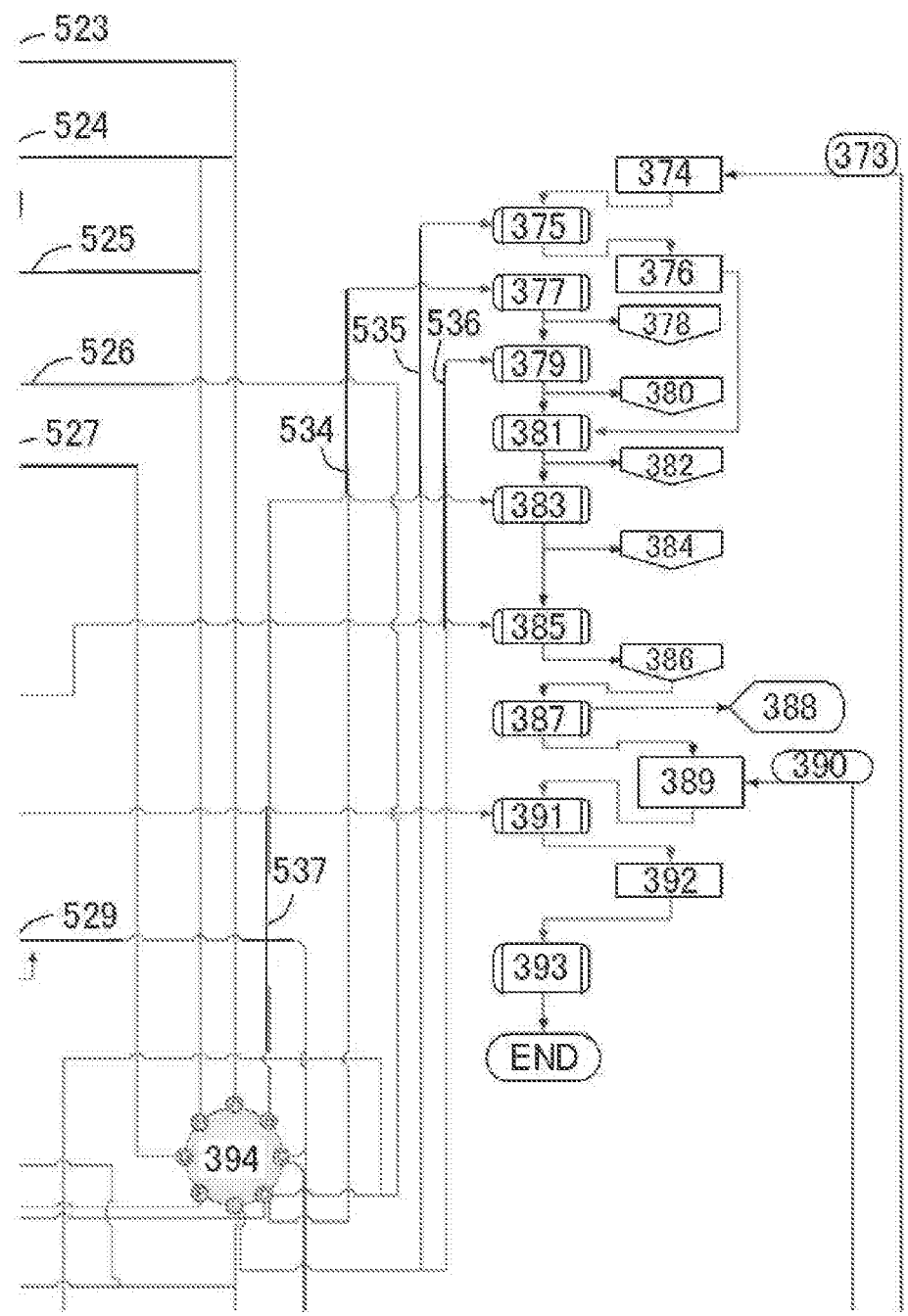
FIG. 8E is a magnified view (upper right part) of FIG. 8.
Figure 8F:
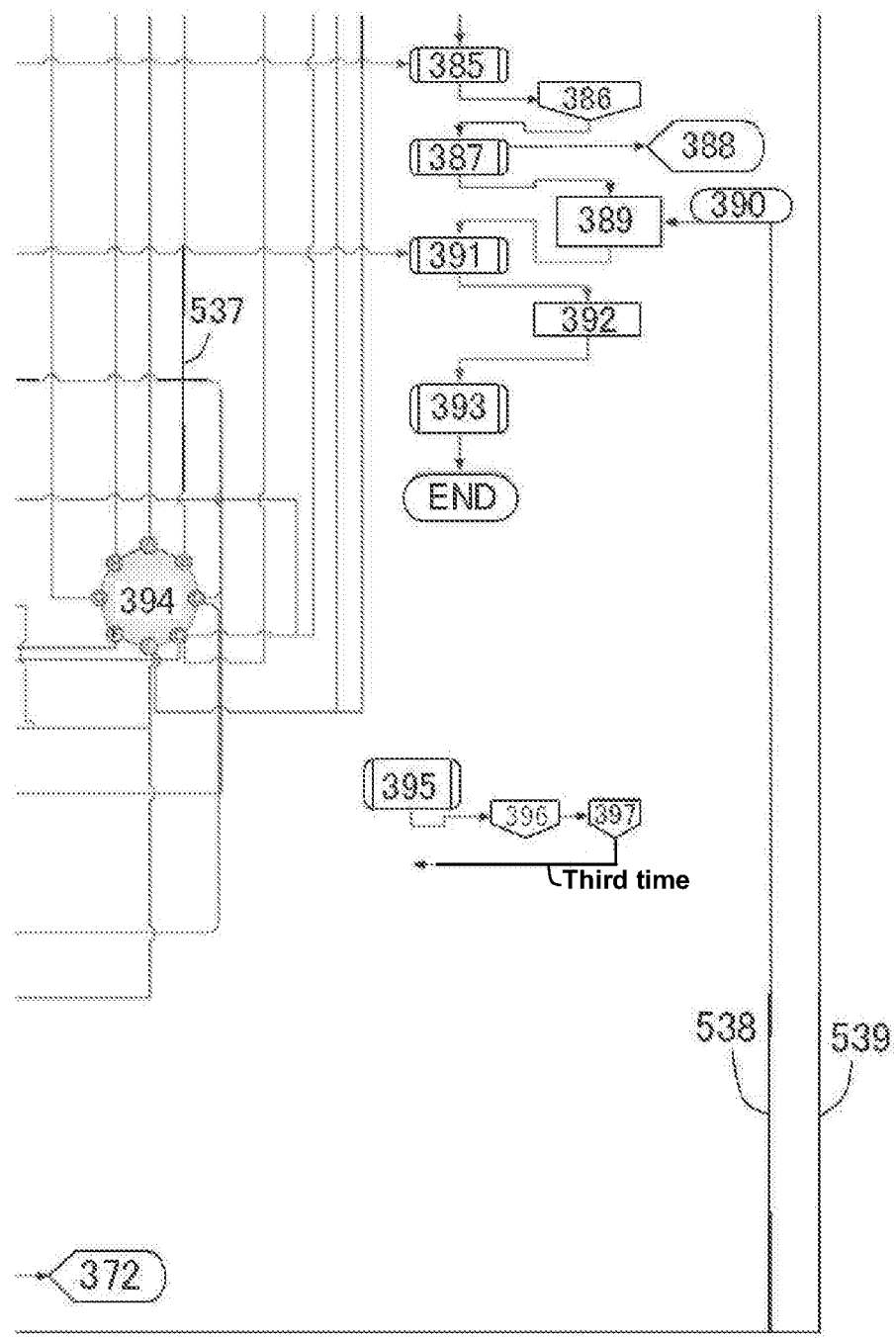
FIG. 8F is a magnified view (lower right part) of FIG. 8.
Figure 9:
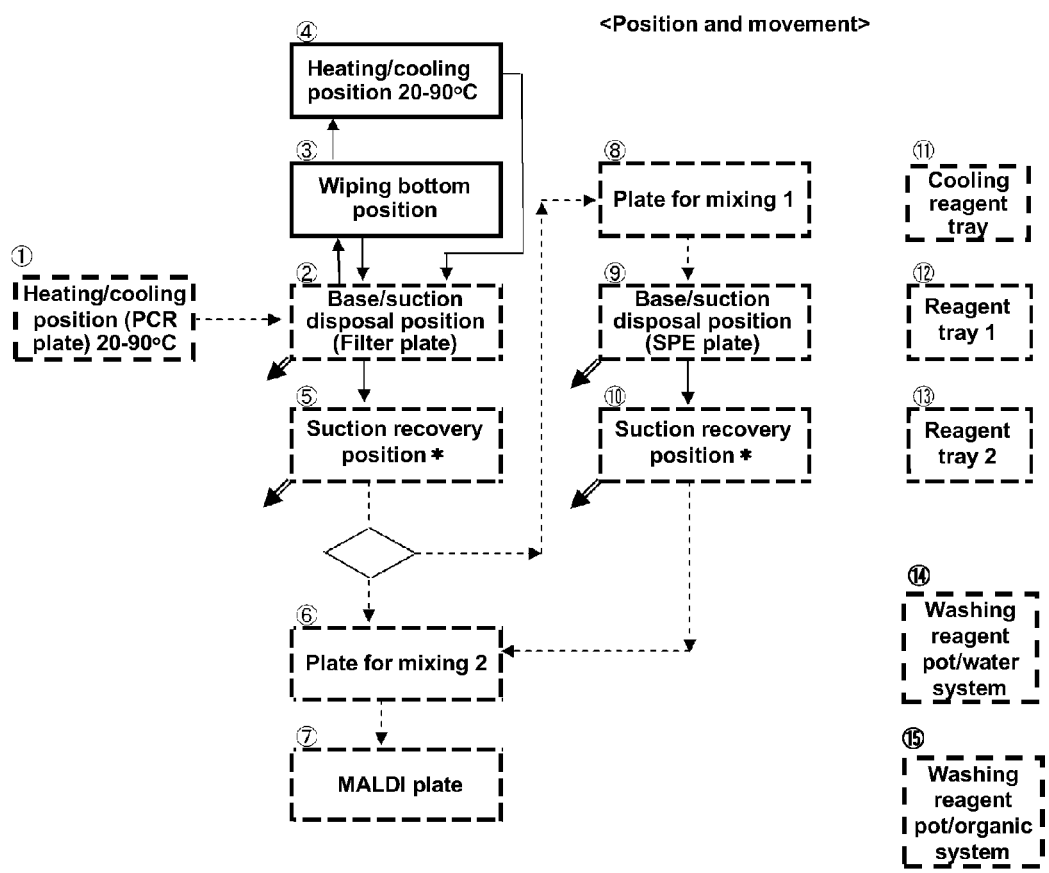
FIG. 9 is a disposition chart as an example of the apparatus of the present invention. A dotted-line rectangle indicates the location where a dispensing needle for reagent or the like is placed. A solid-line rectangle indicates the location where a dispensing needle for reagent or the like is not placed. A dotted-line arrow indicates the movement of a liquid with a dispensing needle for reagent or the like. A solid-line arrow indicates the movement of a filter plate/SPE plate. A double-line arrow indicates the connection to a vacuum pump. A position marked by * indicates the location where cooling to 10% occurs.
Figure 10:
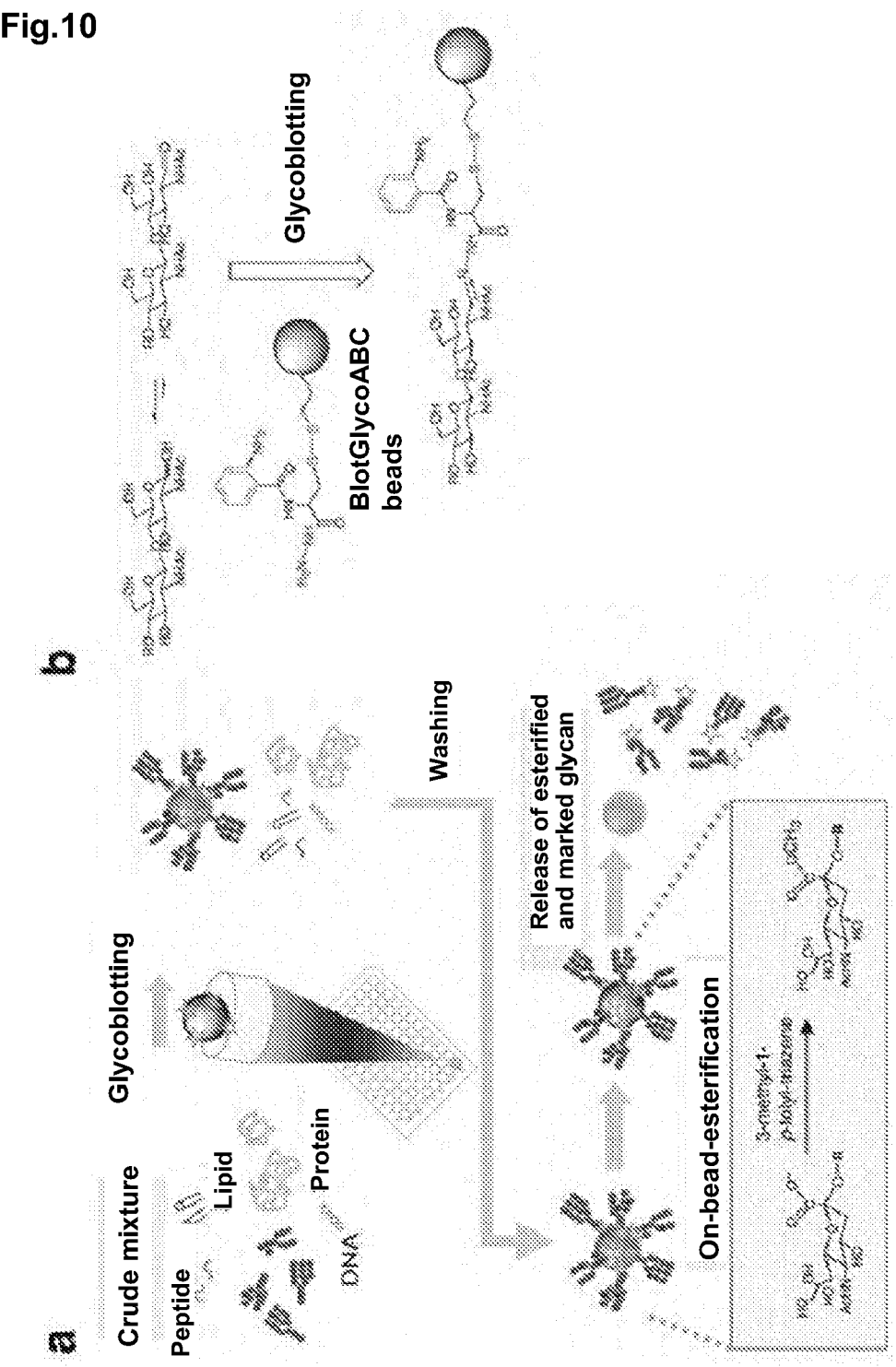
FIG. 10 is a diagram showing an example for a very convenient and feasible approach to the concentrated analysis of complex type sugar conjugate of the present invention (FIG. 10a).
Figure 11A:
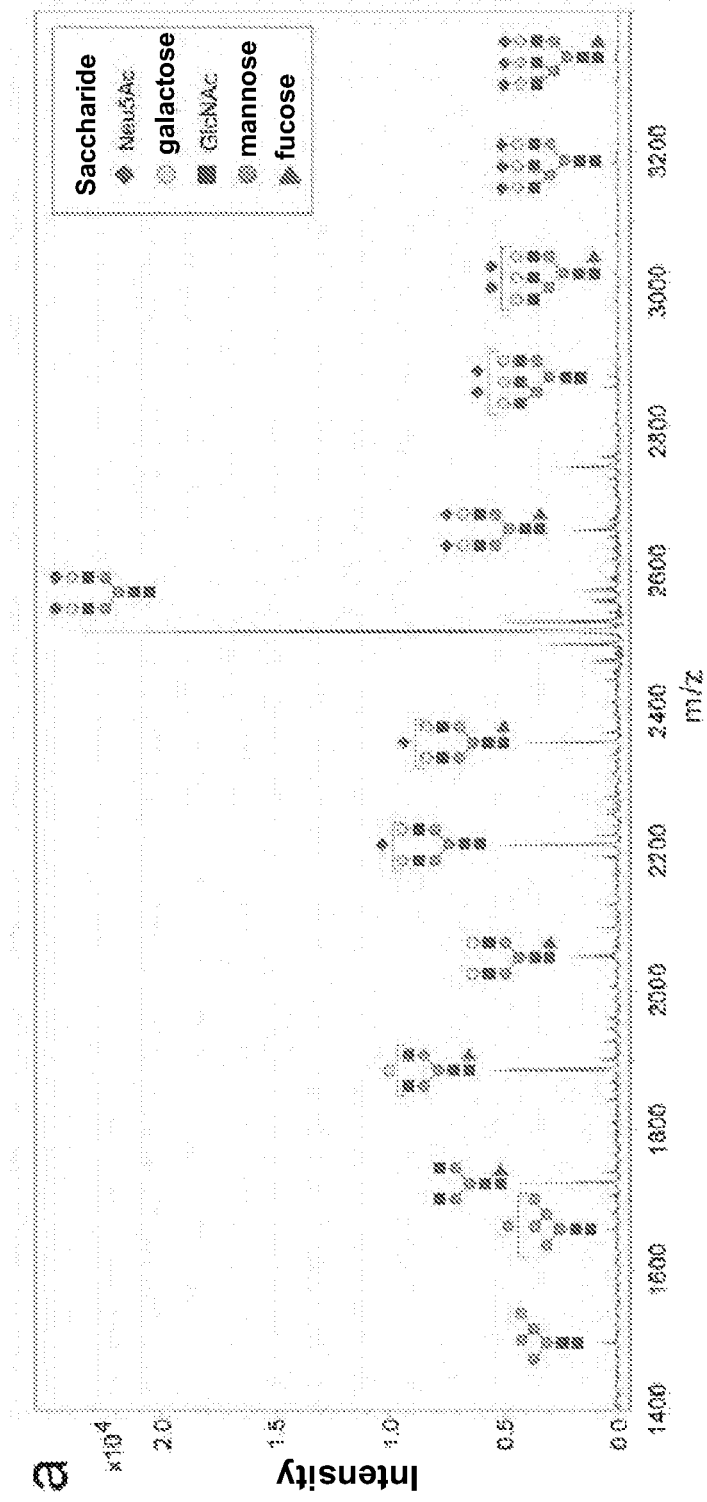
FIG. 11A is a diagram showing the 44 types of N-glycan used as examples in the present invention. Profiling of human serum glycoforms. (a) MALDI-TOF MS spectrum of a representative normal human serum N-glycan. Blood serum that had been digested using trypsin and PNGase F, was subjected directly to the protocol for concentration and derivatization of N-glycan, using BLOTGLYCOABC™ beads. The sialyl N-glycan treated by on-bead methyl esterification was stable against desialylation, and as a result, it should be noted that quantitative glycomics analysis of total N-glycans is made possible.
Figure 11B:
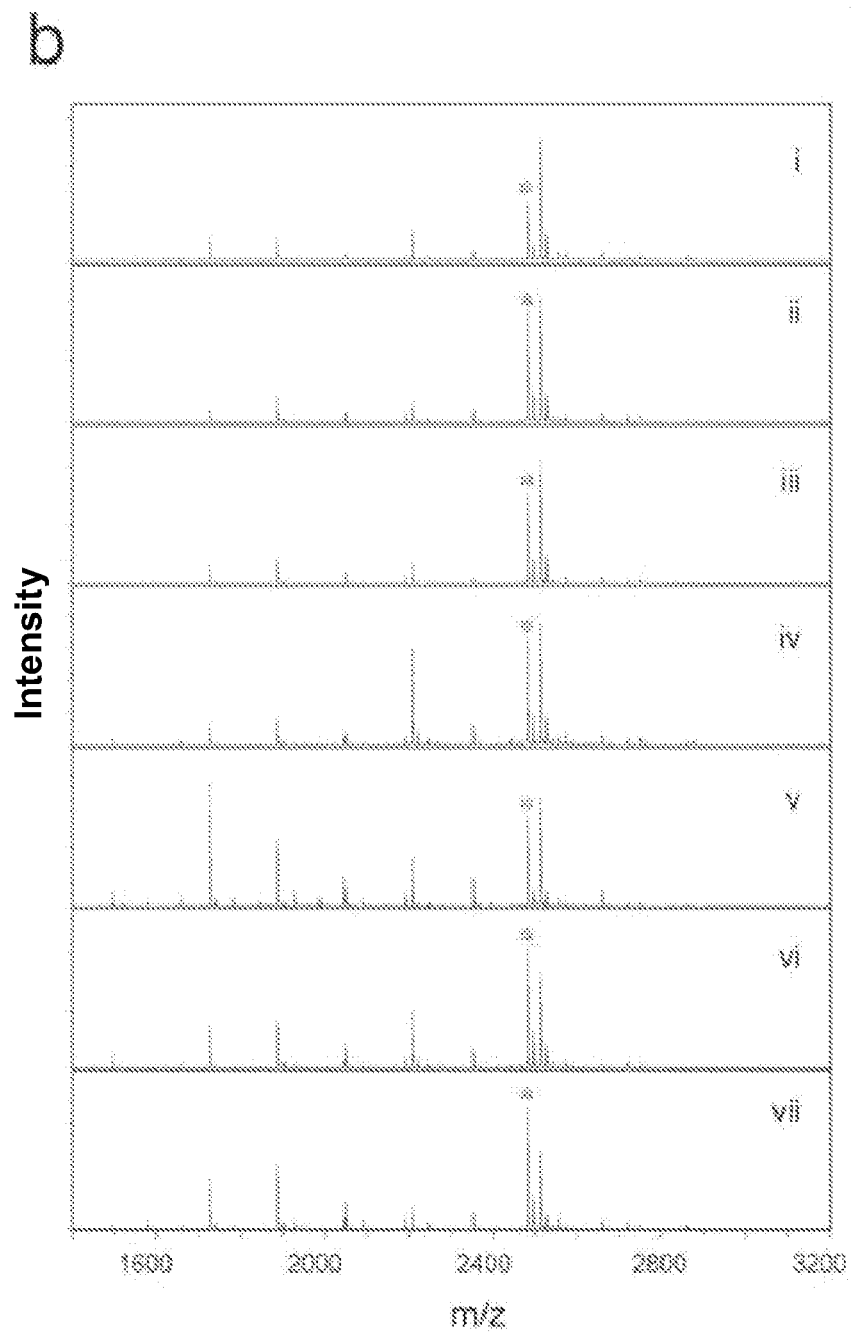
FIG. 11B is a diagram showing the results for a Type-II CDG (CDG-II) patient who has been through the specific stages of the failure of glycosylation. The inventors of the present invention observed an abnormal N-glycan profile (for example, several immature small N-glycan chains). (b) Serum N-glycan profile of a DCG patient found by MALDI-TOF MS. i: Healthy donor, ii: CDG-Ia, iii: CDG-Ib, iv: CDG-IIh, v: CDG-IIx1, vi: CDG-IIx2, and vii: CDG-IIx3. The asterisk indicates the internal standard (A2 amide) in a predetermined amount.
Figure 11C:
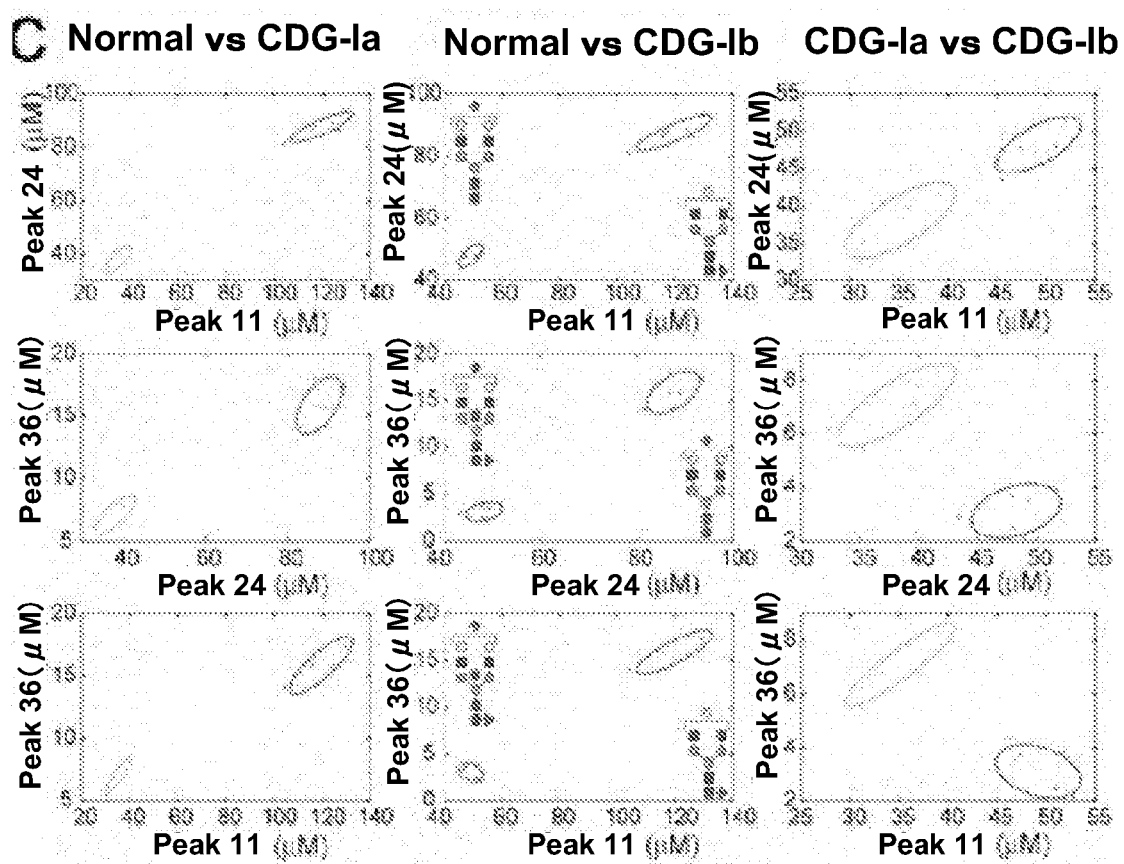
FIG. 11C is a diagram showing pairs of the combinations of the amount of N-glycan, which show the diagnostic differences between CDG-I patients, CDG-Ia patients and CDG-Ib patients. It is shown that the data distribution formed by the amount of the detected 42 types of N-glycan can be used for simple discrimination of the patients from normal blood serum. (c) Classification of CDG-I patients using the expectation maximization algorithm. The selected set of concentration of N-glycan is used to discriminate between healthy patients and CDG-I patients (panels on the left and the middle columns). Similarly, CDG-Ia and CDG-Ib can be successfully discriminated using the same set of N-glycan.
Figure 11D:
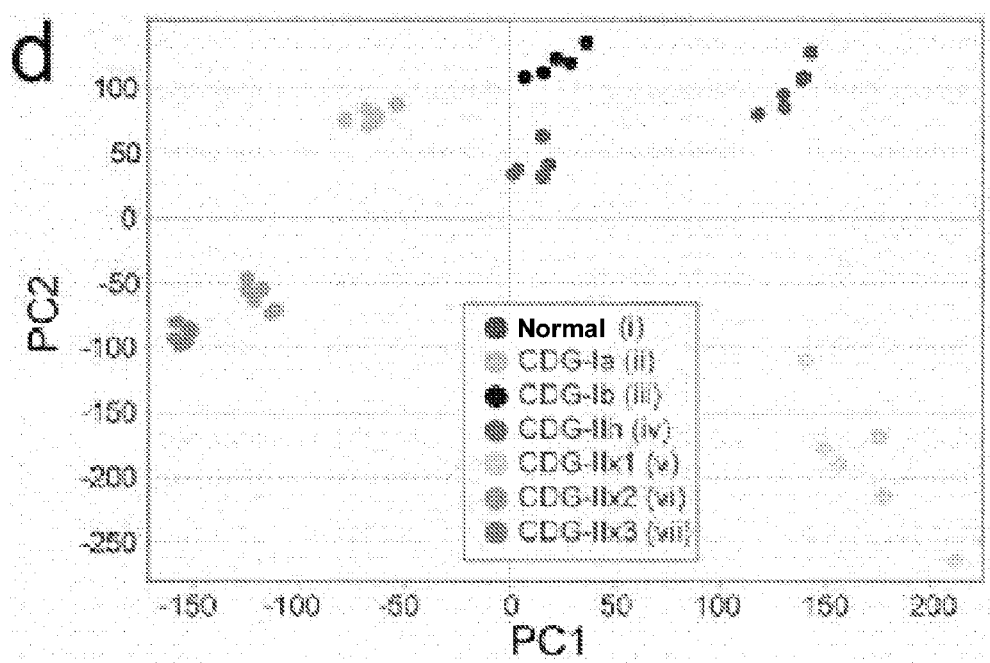
FIG. 11D is a diagram showing the principal component analysis (PCA) of seven kinds in total of the blood serum tested in the present study with regard to the cases of CDG. The first principal component (PC1) and the second principal component (PC2) were plotted. These two principal components occupy 41% and 37%, respectively, of the distribution.
Figure 12A:
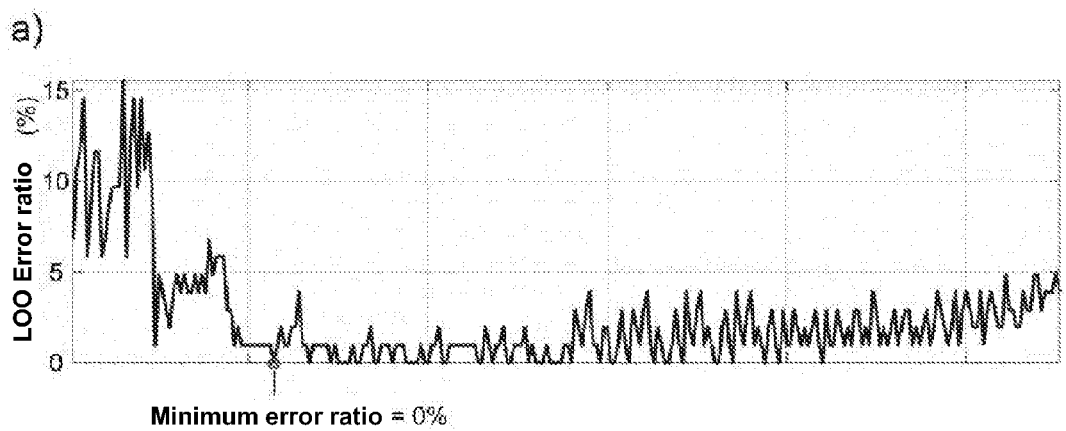
FIG. 12A is a diagram showing the classification based on N-glycans derived from the blood sera of hepatocyte cancer and normal control. (a) Process of feature-subset selection. In this process, the most significant N-glycan ratio in each step was added in succession, and 276 models in total were tested. As a result, the minimum relative error became 0%. (b) Hit map diagram of three species of N-glycan ratios selected as a feature for the classification (Lighter colors represent higher ratios of the presence of glycan). (c) Manifestation in box plots of the selected features (The ratio of presence of N-glycan, structure of oligosaccharide and number of peaks are shown in the diagram).
Figure 12B:
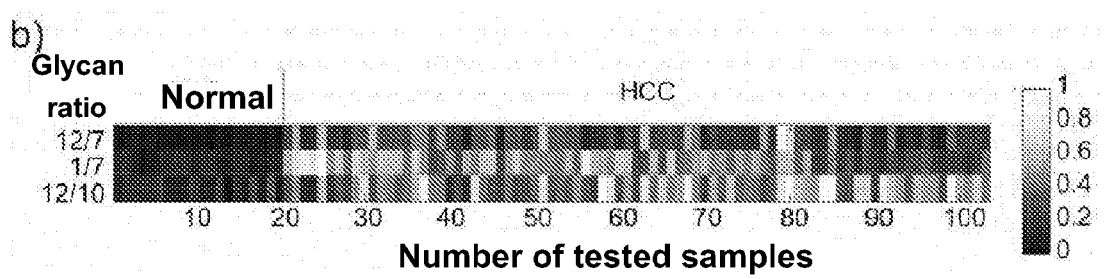
FIG. 12B is a diagram showing the classification based on N-glycans derived from the blood sera of hepatocyte cancer and normal control. (a) Process of feature-subset selection. In this process, the most significant N-glycan ratio in each step was added in succession, and 276 models in total were tested. As a result, the minimum relative error became 0%. (b) Hit map diagram of three species of N-glycan ratios selected as a feature for the classification (Lighter colors represent higher ratios of the presence of glycan). (c) Manifestation in box plots of the selected features (The ratio of presence of N-glycan, structure of oligosaccharide and number of peaks are shown in the diagram).
Figure 12C:
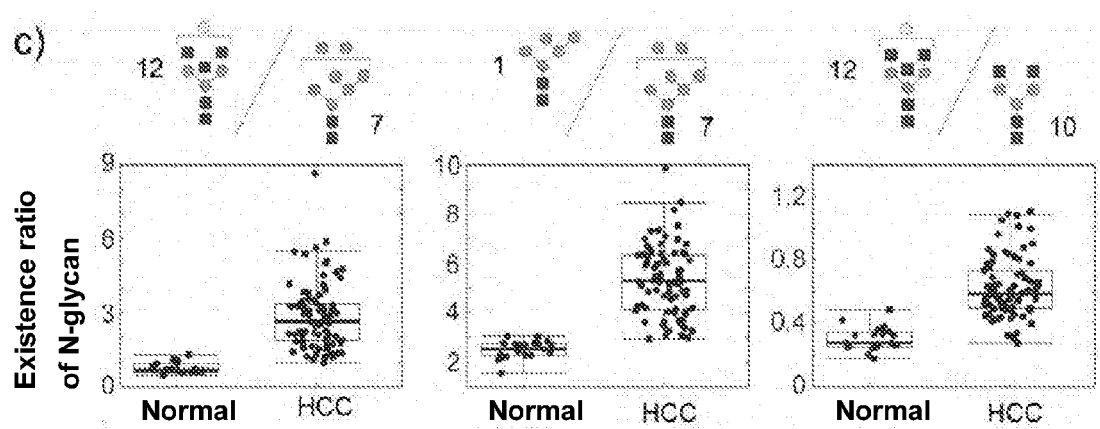
FIG. 12C is a diagram showing the classification based on N-glycans derived from the blood sera of hepatocyte cancer and normal control. (a) Process of feature-subset selection. In this process, the most significant N-glycan ratio in each step was added in succession, and 276 models in total were tested. As a result, the minimum relative error became 0%. (b) Hit map diagram of three species of N-glycan ratios selected as a feature for the classification (Lighter colors represent higher ratios of the presence of glycan). (c) Manifestation in box plots of the selected features (The ratio of presence of N-glycan, structure of oligosaccharide and number of peaks are shown in the diagram).
Figure 13:
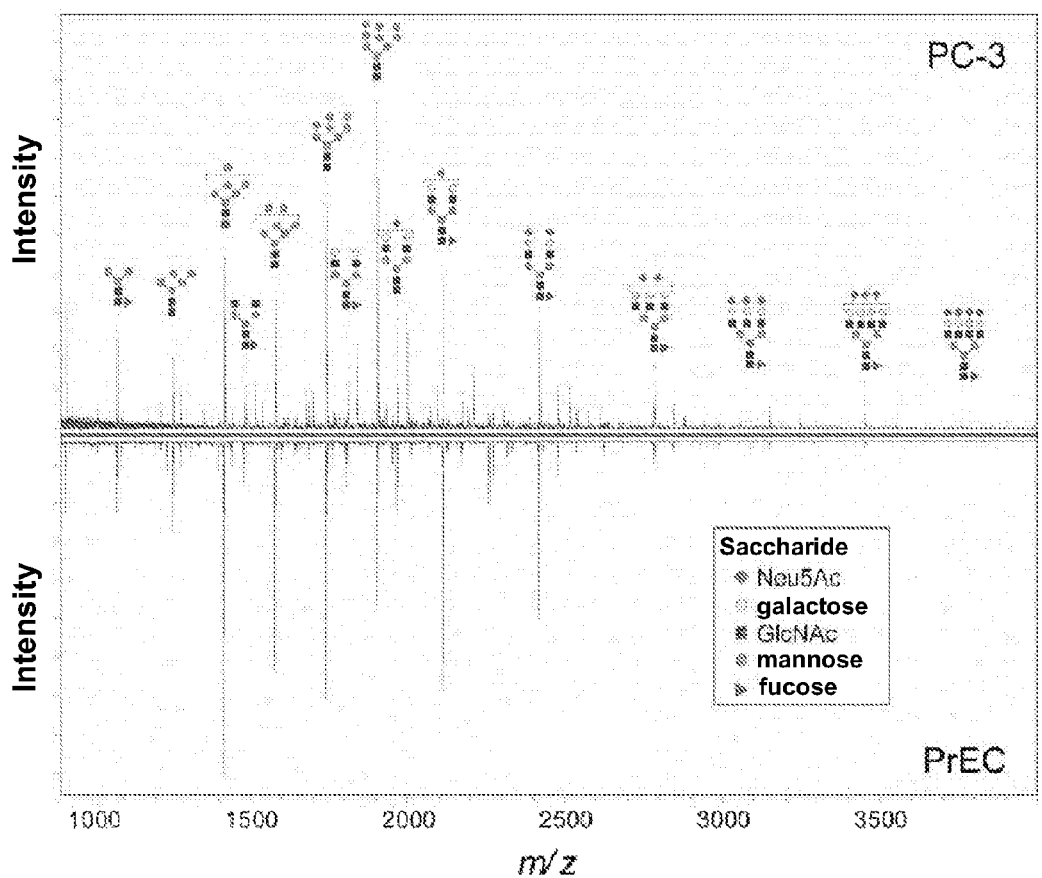
FIG. 13 is a total cellular glycome of human prostate cancer PC-3 cells and of normal human prostate epithelial cells (PrEC). Cells that had been proliferated in a dish measuring 10 cm in size were subjected to glycoblotting and MS analysis using the BLOTGLYCOABC™ beads (also, see the descriptions in the specification).
Figure 14:
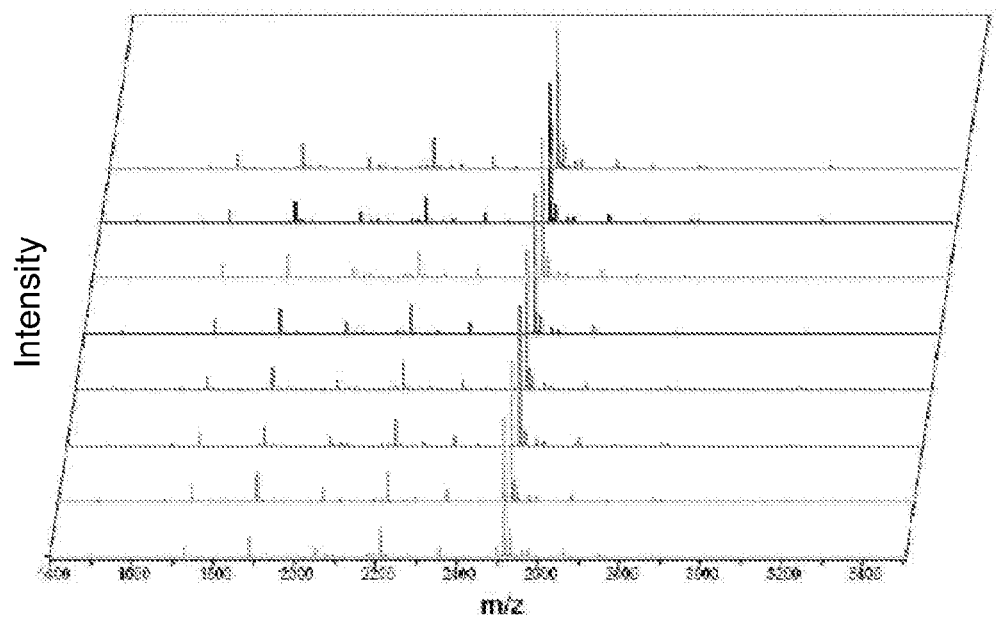
FIG. 14 is a MALDI-TOF MS spectrum of blood serum samples (n=8) prepared by the automated glycoblotting protocol using BLOTGLYCOABC™ beads.
Figure 15:
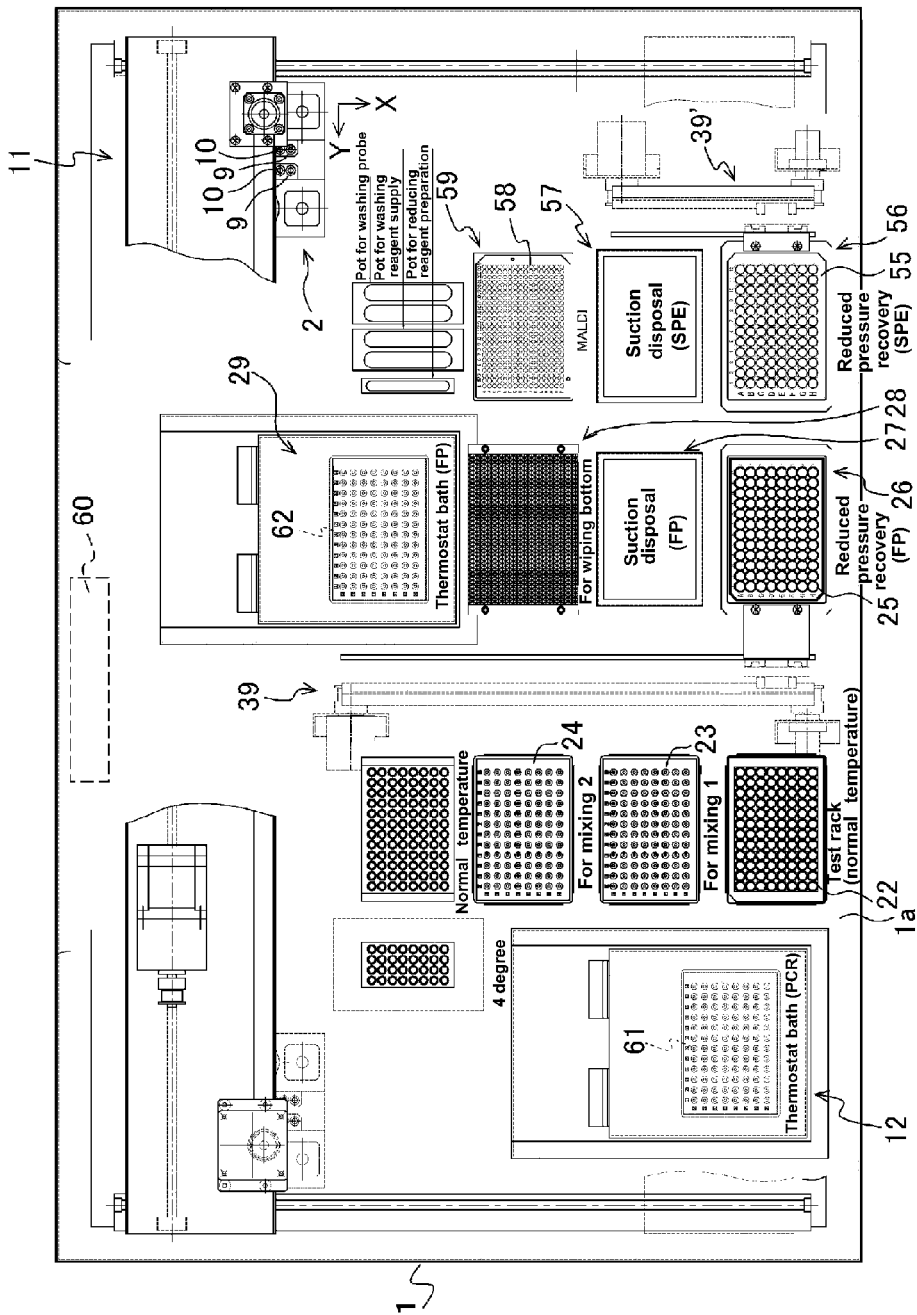
FIG. 15 is a plane view showing the automatic sugar chain pretreatment apparatus according to an embodiment of the present invention, with some parts being omitted from the diagram.
Figure 16:
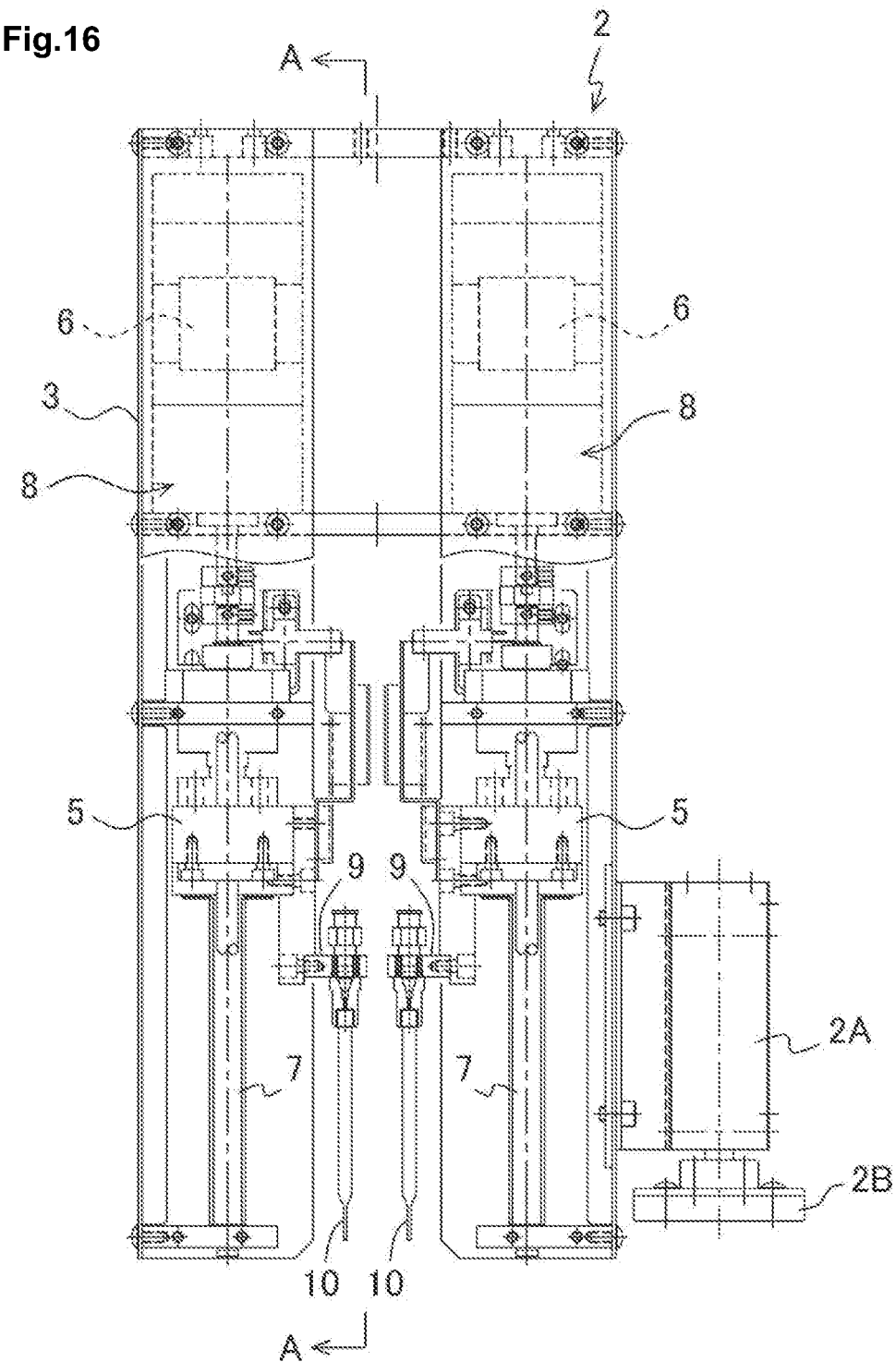
FIG. 16 is a frontal view of the dispensing head.
Figure 17:
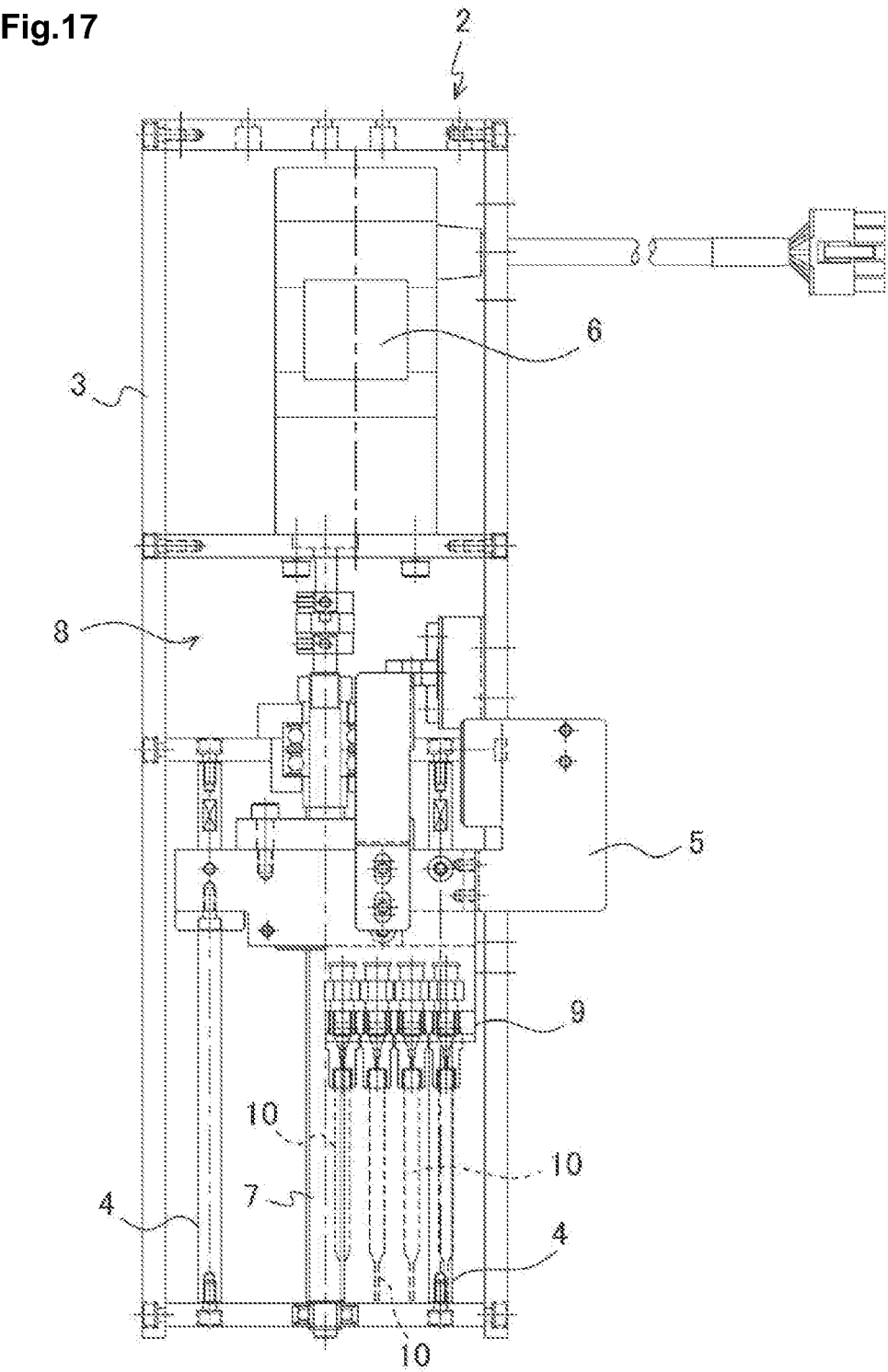
FIG. 17 is a cross-sectional view of FIG. 16, dissected along the line A-A.
Figure 18:
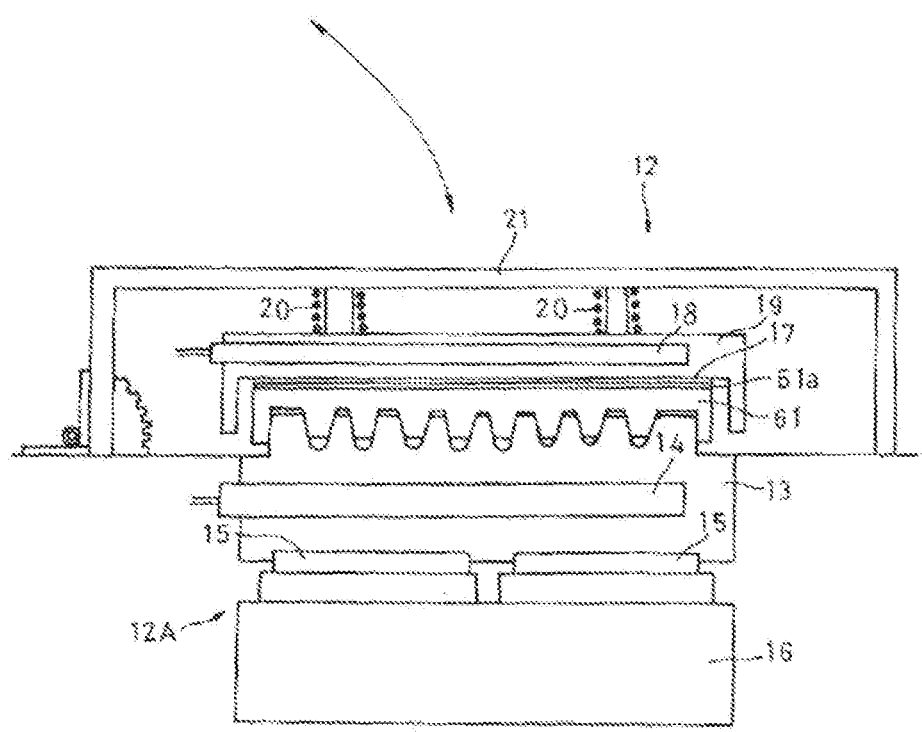
FIG. 18 is a central vertical cross-sectional view of the first constant-temperature bath.
Figure 19:
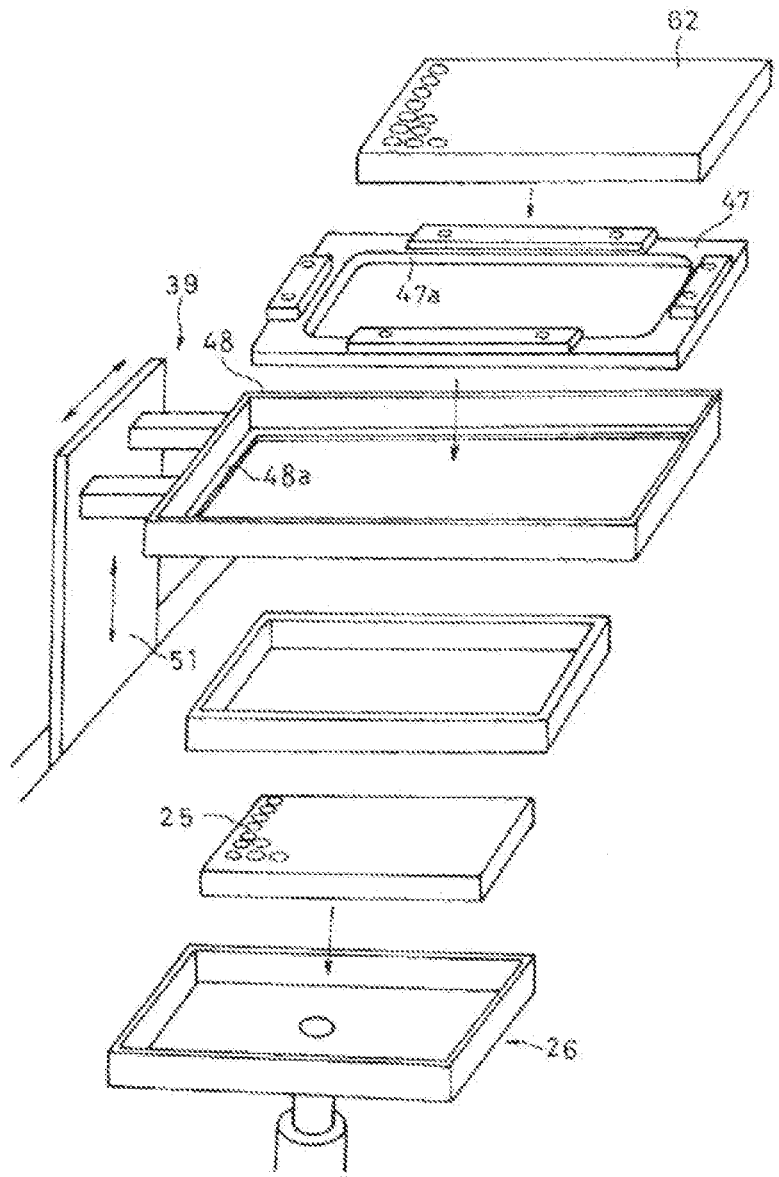
FIG. 19 is an exploded perspective view showing the first low-pressure recovering device and the filter plate moving mechanism.
Figure 20:
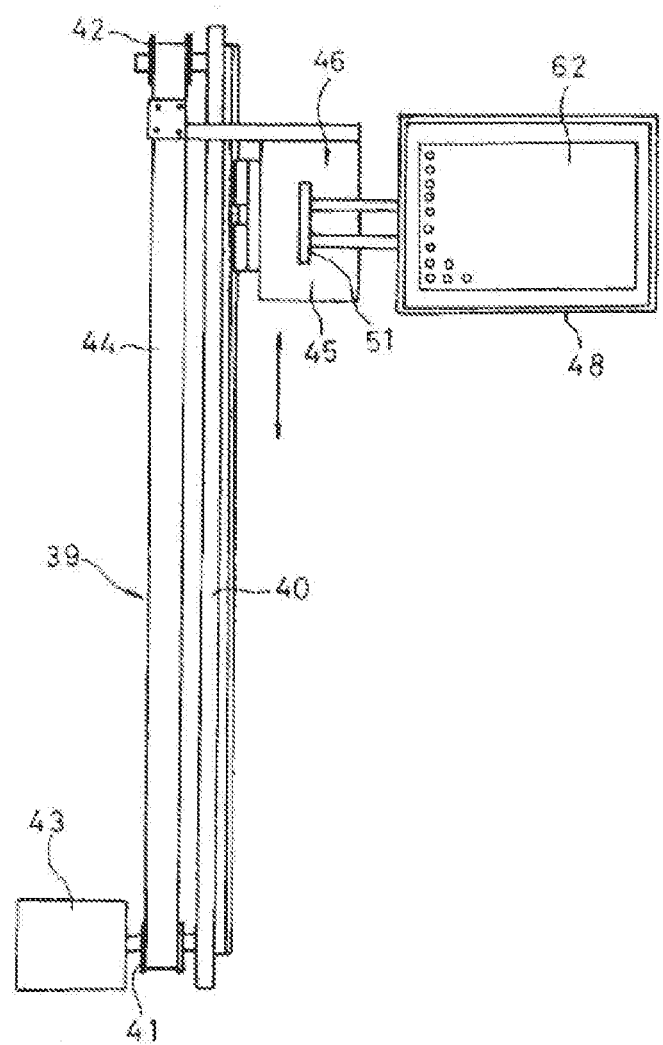
FIG. 20 is a plane view showing the filter plate moving mechanism, with some parts being omitted from the diagram.
Figure 21:
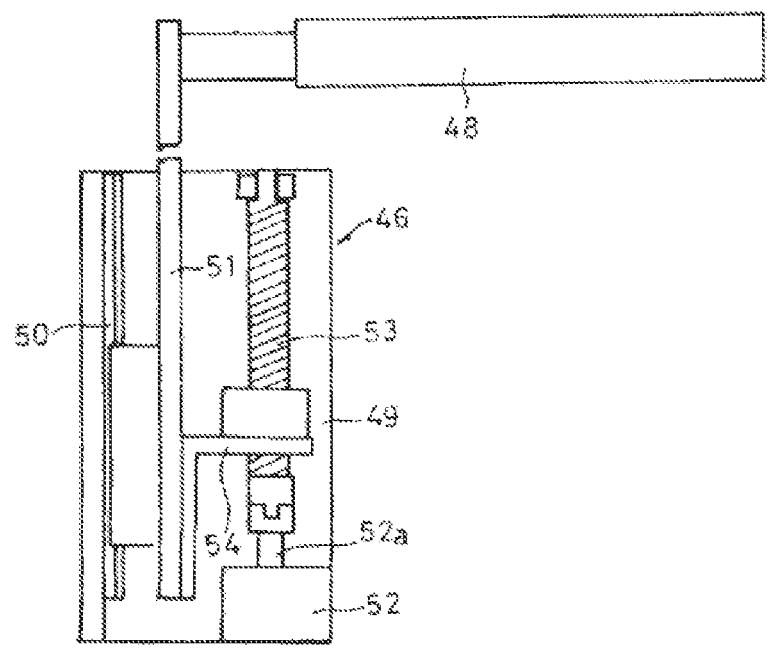
FIG. 21 is a vertical cross-sectional view showing the vertical moving unit in the filter plate moving mechanism, with some parts being omitted from the diagram.
Figure 22:
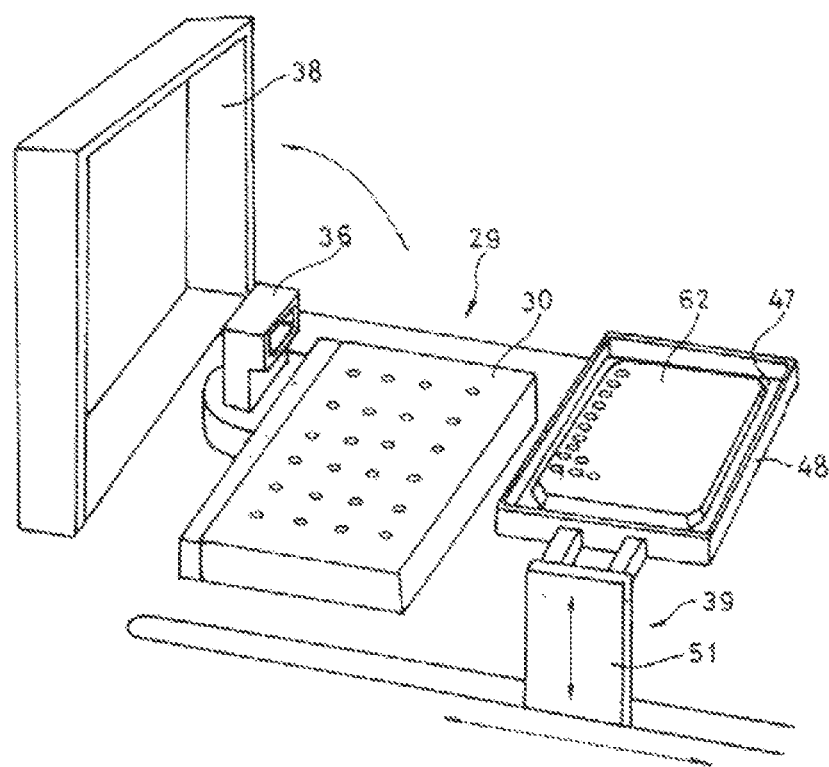
FIG. 22 is a perspective view of the filter plate moving mechanism and the second constant-temperature bath.
Figure 23:
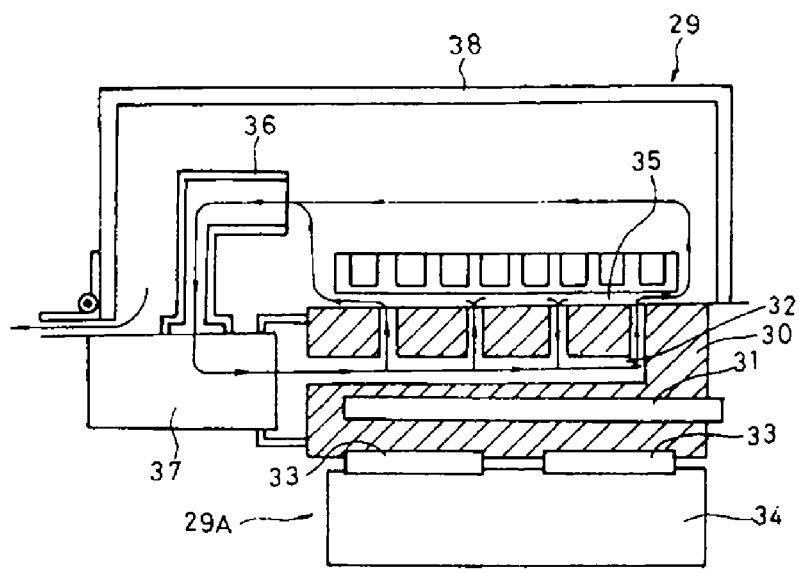
FIG. 23 is a central vertical cross-sectional view of the second constant-temperature bath.
Figure 24:
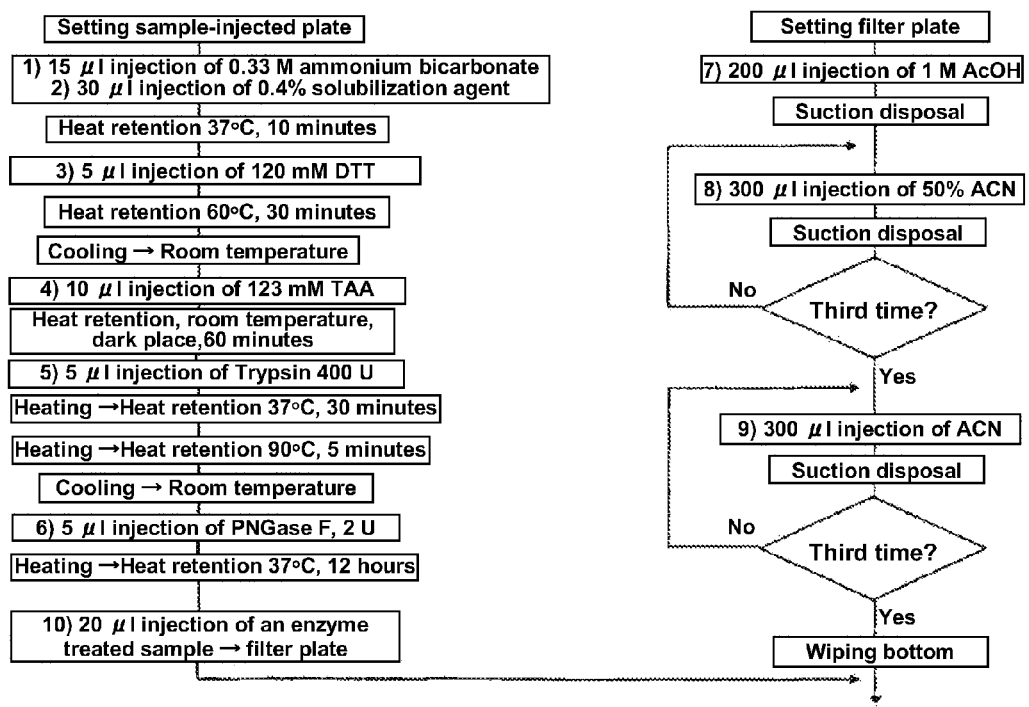
FIG. 24 is a flow diagram of the treatment operation.
Figure 25:
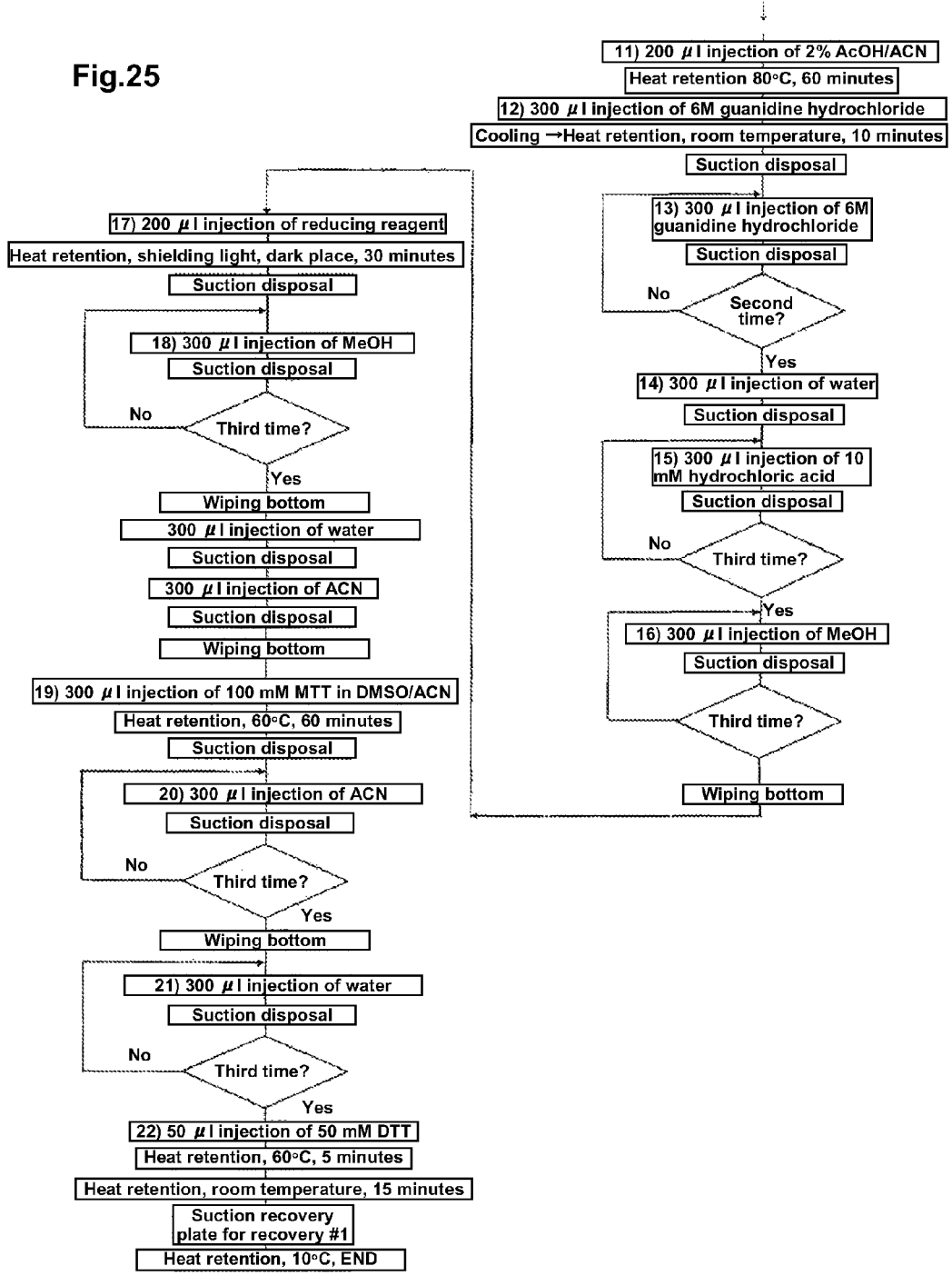
FIG. 25 is a flow diagram of the treatment operation that follows the treatment operation of FIG. 24.

1 CASING BASE
1a DISPOSITION SPACE OF CASING BASE
2 DISPENSING HEAD
2A CYLINDER
2B PRESSURIZING PLATE
3 SUPPORTING FRAME
4 GUIDE ROD
5 ELEVATOR STAND
6 DRIVING MOTOR
7 BALL SCREW
8 ELEVATOR STAND MOVING MECHANISM
9 DISPENSING NEEDLE HOLDER
10 DISPENSING NEEDLES
11 DISPENSING HEAD MOVING MECHANISM
12 FIRST CONSTANT-TEMPERATURE BATH
12A MAIN BODY PART
13 RECEIVING STAND
14 CARTRIDGE HEATER
15 PELTIER ELEMENT
16 HEAT SINK
17 SILICONE SHEET
18 CARTRIDGE HEATER
19 INNER LID
21 LID
22 REAGENT RACK
23, 24 MICROPLATE FOR MIXING
25 MICROPLATE
26 FIRST LOW-PRESSURE RECOVERING DEVICE
27 FIRST SUCTION DISCARDING DEVICE
28 BOTTOM WIPER
29 SECOND CONSTANT-TEMPERATURE BATH
29A MAIN BODY PART
30 RECEIVING STAND
31 CARTRIDGE HEATER
32 AIR CIRCULATION PATH
33 PELTIER ELEMENT
34 HEAT SINK
35 AIR CIRCULATION PATH
36 DUCT
37 FAN
38 LID
39 FILTER PLATE MOVING MECHANISM
40 SUPPORTING PLATE
41,42 PULLEY
43 MOTOR
44 BELT
45 HORIZONTALLY MOVING PLATE
46 VERTICAL MOVING UNIT
47 INNER FRAME
48 RECEIVING FRAME
49 SUPPORTING FRAME
50 GUIDE
51 VERTICALLY MOVING ROD
52 MOTOR
53 BALL SCREW
54 ELEVATING ROD
55 MICROPLATE
56 SECOND LOW-PRESSURE RECOVERING DEVICE
58 TARGET PLATE
59 TARGET PLATE RECEIVING STAND
60 CONTROL DEVICE
61 MICROPLATE
62 FILTER PLATE
101 10 µl OF SERUM
102 SERUM-CONTAINING FILTER PLATE
103 KEPT WARM AT 37° C., FOR 10 MINUTES
104 SERUM-CONTAINING FILTER PLATE
105 KEPT WARM AT 60° C., FOR 30 MINUTES
106 SERUM-CONTAINING FILTER PLATE
107 COOLED TO ROOM TEMPERATURE
108 SERUM-CONTAINING FILTER PLATE
109 KEPT WARM AT ROOM TEMPERATURE, FOR 1 HOUR IN THE DARK
110 SERUM-CONTAINING FILTER PLATE
111 KEPT WARM AT 37° C., FOR 60 MINUTES
112 SERUM-CONTAINING FILTER PLATE
113 KEPT WARM AT 90° C., FOR 5 MINUTES
114 SERUM-CONTAINING FILTER PLATE
115 COOLED TO ROOM TEMPERATURE
116 SERUM-CONTAINING FILTER PLATE
117 KEPT WARM AT 37° C., FOR 12 HOURS
118 SERUM-CONTAINING FILTER PLATE
119 REAGENT RACK, AT 4° C., 1.5 ml
120 REAGENT RACK, ROOM TEMPERATURE, LIGHT-SHIELDED
121 SERUM-CONTAINING FILTER PLATE
122 KEPT WARM AT 80° C., FOR 45 MINUTES
123 SERUM-CONTAINING FILTER PLATE
124 DISCARDING BY SUCTION
125 SERUM-CONTAINING FILTER PLATE
126 DISCARDING BY SUCTION
127 SERUM-CONTAINING FILTER PLATE
128 DISCARDING BY SUCTION
129 SERUM-CONTAINING FILTER PLATE
130 KEPT WARM AT ROOM TEMPERATURE, FOR 30 MINUTES
131 SERUM-CONTAINING FILTER PLATE
132 DISCARDING BY SUCTION
133 DISCARDING BY SUCTION
134 SERUM-CONTAINING FILTER PLATE
135 DISCARDING BY SUCTION
136 SERUM-CONTAINING FILTER PLATE
137 DISCARDING BY SUCTION
138 BOTTOM WIPER
139 SERUM-CONTAINING FILTER PLATE
140 KEPT WARM AT 80° C., FOR 60 MINUTES
141 SERUM-CONTAINING FILTER PLATE
142 DISCARDING BY SUCTION
143 SERUM-CONTAINING FILTER PLATE
144 DISCARDING BY SUCTION
145 SERUM-CONTAINING FILTER PLATE
146 KEPT WARM AT 80° C., FOR 45 MINUTES
147 SERUM-CONTAINING FILTER PLATE

148 EXTRACTION BY SUCTION
149 WASHING VALVE
150 PLATE FOR RECOVERY 1
151 DISPENSING 20 μl
152 MP1 FOR MIXING
153 DISPENSING 380 μl
154 SPE PLATE
155 DISCARDING BY SUCTION
156 SPE PLATE
157 DISCARDING BY SUCTION
158 SPE PLATE
159 DISCARDING
160 SPE PLATE
161 DISCARDING BY SUCTION
162 SPE PLATE
163 RECOVERY BY SUCTION
164 PLATE FOR RECOVERY 2
165 DISPENSING 2 μl
166 MP2 FOR MIXING
167 DISPENSING 2 μl
168 MALDI PLATE
169 END
201 TRYPSIN 400 U, 5 μl
202 PNGase F, 2 U, 5 μl
203 0.26% PHL (SOLUBILIZING AGENT)/0.11 M AMMONIUM BICARBONATE, 45 μl (CV 5%)
204 120 mM DTT, 5 μl (CV 5%)
205 123 mM IAA, 10 μl (CV 5%)
206 10% $Ac_2O$/MeOH, 100 μl
207 150 mM MTT/DIOXANE, 100 μl
208 20 mM REAGENT, 20 μl
209 2% AcOH/ACN, 180 μl
210 2 M GUANIDINE HYDROCHLORIDE, 200 μl×2
211 WATER, 200 μl×2
212 1% TEA/MeOH, 200 μl×2
213 10 mM HCl, 200 μl×2
214 MeOH, 200 μl×2
215 DIOXANE, 200 μl×2
216 DIOXANE, 200 μl×2
217 WATER, 200 μl×1
218 2% AcOH/ACN, 180 μl
219 WATER, 100 μl×1
220 95%, ACN, 360 μl
221 WATER, 200 μl
222 95%, ACN, 200 μl
223 95%, ACN, 200 μl
224 5%, ACN, 100 μl
225 DHB/30% ACN, 18 μl
In 149,
A 2% ACETIC ACID (AcOH)/ACETONITRILE (ACN)
B WATER
C 2 M GUANIDINE HYDROCHLORIDE
D 95% ACETONITRILE (ACN)
E DIOXANE
F METHANOL (MeOH)
G 10 mM HCl
H 1% TEA/METHANOL (MeOH)
301 10 μl SERUM
302 PCR PLATE
303 SERUM-CONTAINING PCR PLATE
304 KEPT WARM AT 37° C., FOR 10 MINUTES
305 SERUM-CONTAINING PCR PLATE
306 KEPT WARM 60° C., FOR 30 MINUTES
307 SERUM-CONTAINING PCR PLATE
308 COOLED TO ROOM TEMPERATURE
309 SERUM-CONTAINING PCR PLATE
310 KEPT WARM AT ROOM TEMPERATURE, FOR 1 HOUR IN THE DARK
311 SERUM-CONTAINING PCR PLATE
312 KEPT WARM AT 37° C., FOR 60 MINUTES
313 SERUM-CONTAINING PCR PLATE
314 KEPT WARM AT 90° C., FOR 5 MINUTES
315 SERUM-CONTAINING PCR PLATE
316 COOLED TO ROOM TEMPERATURE
317 SERUM-CONTAINING PCR PLATE
318 KEPT WARM AT 37° C., FOR 12 HOURS
319 SERUM-CONTAINING PCR PLATE
320 REAGENT RACK, 4° C., 1.5 ml
321 REAGENT RACK, ROOM TEMPERATURE
322 DISPENSING 20 μl
323 DISCARDING BY SUCTION
324 DISCARDING BY SUCTION
325 DISCARDING BY SUCTION
326 BOTTOM WIPER
327 BEADS-CONTAINING FILTER PLATE
328 BEADS-CONTAINING FILTER PLATE
329 BEADS-CONTAINING FILTER PLATE
330 BEADS-CONTAINING FILTER PLATE
331 KEPT WARM AT 80° C., FOR 60 MINUTES
332 BEADS-CONTAINING FILTER PLATE
333 KEPT WARM AT ROOM TEMPERATURE, FOR 10 MINUTES
334 DISCARDING BY SUCTION
335 BEADS-CONTAINING FILTER PLATE
336 DISCARDING BY SUCTION
337 BEADS-CONTAINING FILTER PLATE
338 DISCARDING BY SUCTION
339 BEADS-CONTAINING FILTER PLATE
340 DISCARDING BY SUCTION
341 BEADS-CONTAINING FILTER PLATE
342 DISCARDING BY SUCTION
343 BOTTOM WIPER
344 BEADS-CONTAINING FILTER PLATE
345 KEPT WARM, LIGHT-SHIELDED, ROOM TEMPERATURE, FOR 30 MINUTES
346 BEADS-CONTAINING FILTER PLATE
347 DISCARDING BY SUCTION
348 BEADS-CONTAINING FILTER PLATE
349 DISCARDING BY SUCTION
350 BOTTOM WIPER
351 BEADS-CONTAINING FILTER PLATE
352 DISCARDING BY SUCTION
353 BEADS-CONTAINING FILTER PLATE
354 DISCARDING BY SUCTION
355 BOTTOM WIPER
356 BEADS-CONTAINING FILTER PLATE
357 KEPT WARM AT 60° C., FOR 60 MINUTES
358 BEADS-CONTAINING FILTER PLATE
359 DISCARDING BY SUCTION
360 BEADS-CONTAINING FILTER PLATE
361 DISCARDING BY SUCTION
362 BOTTOM WIPER
363 BEADS-CONTAINING FILTER PLATE
364 DISCARDING BY SUCTION
365 BEADS-CONTAINING FILTER PLATE
366 50 mM DTT IN 50 mM AMMONIUM BICARBONATE, 50 μl
367 KEPT WARM AT 60° C., FOR 5 MINUTES
368 KEPT WARM AT ROOM TEMPERATURE, FOR 15 MINUTES
369 BEADS-CONTAINING FILTER PLATE
370 RECOVERY BY SUCTION
371 PLATE FOR RECOVERY 1

372 KEPT WARM AT 10° C., TO COMPLETION
373 SPE INITIATION
374 DISPENSING 20 μl
375 MP FOR MIXING 1
376 DISPENSING 420 μl
377 SPE PLATE
378 DISCARDING BY SUCTION
379 SPE PLATE
380 DISCARDING BY SUCTION
381 SPE PLATE
382 DISCARDING BY SUCTION
383 SPE PLATE
384 DISCARDING BY SUCTION
385 SPE PLATE
386 RECOVERY BY SUCTION
387 PLATE FOR RECOVERY 2
388 KEPT WARM AT 10° C., TO COMPLETION
389 DISPENSING 2 μl
390 MALDI DISPENSING INITIATED
391 MP FOR MIXING 2
392 DISPENSING 2 μl
393 MALDI PLATE
394 WASHING VALVE
395 BEADS-CONTAINING FILTER PLATE
396 DISCARDING BY SUCTION
397 BOTTOM WIPER
In 394,
A 2% ACETIC ACID (AcOH)/ACETONITRILE (ACN), 20 ml
B 95% ACETONITRILE (ACN) IN WATER, 20 ml
C METHANOL (MeOH), 200 ml
D WATER
E 95% ACETONITRILE (ACN), 330 ml
F 50% ACETONITRILE (ACN)
G 10 mM HYDROCHLORIC ACID, 100 ml
H 6 M GUANIDINE HYDROCHLORIDE, 100 ml
401 REGULATION OF REDUCING REAGENT WORK
402 REDUCING REAGENT
403 REAGENT RACK, ROOM TEMPERATURE/LIGHT-SHIELDED
404 DISPENSING 20 μl
405 DISPENSING 40 μl
406 R9 (2 ml)
407 8 M BORANEPYRIDINE
408 EMPTY RACK
409 R11 (20 ml)
410 R10 (4 ml)
411 MeOH, 140 μl
412 50% AQUEOUS SOLUTION OF TRICHLOROACETIC ACID
501 0.33 M AMMONIUM BICARBONATE, 15 μl, CV 5%
502 0.4% SOLUBILIZING AGENT, 30 μl, CV 5%
503 120 mM DTT, 5 μl, CV 5%
504 123 mM IAA, 10 μl, CV 5%
505 TRYPSIN, 400 U, 5 μl
506 PNGase F, 2 U, 5 μl
508 R1 (1.5 ml)
509 R2 (3 ml)
510 R12 (20 ml)
511 R3 (0.5 ml)
512 R4 (1 ml)
513 R5 (2 ml)
514 R6 (0.2 ml)
515 R7 (10 ml)
516 R8 (5 ml)
517A ACN, 300 μl×3
517B 50% ACN, 300 μl×3
518 1 M AcOH, 200 μl
519 10% ACN, 20 μl
520 MALDI MATRIX, 2 μl
521 200 μl
522 100 mM MTT IN DMSO/ACN, 100 μl
523 20 AcOH/ACN, 200 μl
524 6 M GUANIDINE HYDROCHLORIDE, 300 μl
525 6 M GUANIDINE HYDROCHLORIDE, 300 μl×2
526 WATER, 300 μl
527 10 mM HYDROCHLORIC ACID, 300 μl×3
528 MeOH, 300 μl×3
529 MeOH, 300 μl×3
530 WATER, 300 μl×3
531 ACN, 300 μl×3
532 ACN, 300 μl×3
533 WATER, 300 μl×3
534 WATER, 200 μl
535 ACN, 400 μl
536 ACN, 200 μl
537 95% ACN, 200 μl
538 MALDI DISPENSING ONLY
539 MALDI DISPENSING AFTER SPE TREATMENT

The invention claimed is:

1. A method for analyzing a sugar chain in a sample, the method comprising the following steps:
   A) a sugar chain releasing step of releasing a sugar chain in a sample, the step comprising the following steps:
      A-1) a step of providing the sample on a plate for reaction;
      A-2) a step of adding a solubilizing agent to the sample to thereby place the sample under a reaction condition;
      A-3) a step of adding a reducing agent to the sample to thereby place the sample under a reaction condition;
      A-4) a step of adding an —SH protecting agent to the sample to thereby place the sample under a reaction condition;
      A-5) a step of adding a proteolytic enzyme to the sample to thereby place the sample under a reaction condition;
      A-6) a step of deactivating the proteolytic enzyme; and
      A-7) a step of adding a sugar chain releasing enzyme to the sample to thereby release the sugar chain;
   B) a detection sample preparing step of preparing the released sugar chain for use in detection, the step comprising the following steps:
      B-1) a step of contacting the sample prepared in the step (A) with a sugar chain-capturing bead to thereby place the sample under the conditions allowing the released sugar chain in the sample to bind to the bead, and thus producing a captured sugar chain sample;
      B-2) a step of adding a protein denaturing agent to the captured sugar chain sample to thereby place the captured sugar chain sample under a reaction condition;
      B-3) a step of washing the captured sugar chain sample, and then discarding the residual washing liquid by suction;
      B-4) a step of adding a salt releasing agent for the sugar chain capturing agent on beads to the captured sugar chain sample, and then discarding the salt releasing agent by suction;
      B-5) a step of adding a protective agent to the captured sugar chain sample to thereby place the captured sugar chain under a reaction condition;
      B-6) a step of adding an acid to the captured sugar chain sample, and discarding the acid by suction;

B-7) a step of adding an organic reaction solvent to the captured sugar chain sample;

B-8) a step of removing the solvent and the moisture in the bead;

B-9) a step of adding a methyl esterifying agent to the captured sugar chain sample to thereby place the captured sugar chain sample under a reaction condition, and alkylating the carboxylic acid of sialic acid;

B-10) a step of adding the organic reaction solvent to the captured sugar chain sample, and discarding the organic reaction solvent by suction;

B-11) a step of washing the captured sugar chain sample, and subsequently discarding the residual washing liquid by suction;

B-12) a step of releasing a sugar chain sample from the captured sugar chain sample, wherein when an analysis requiring tagging is conducted, the sugar chain in the captured sugar chain sample is tagged with a labeling reagent and is released from the bead; and B-13) a step of dissolving the released sugar chain sample to produce a sugar chain sample solution;

C) when performing mass spectrometry using a plate, a step of producing a plate for mass spectrometry having the captured sugar chain dotted thereon, the step comprising:

C-1) a step of disposing the tagged sugar chain sample solution obtained in the step (B) on a plate for recovery;

C-2) a step of disposing the tagged sugar chain sample solution from the plate for recovery by adding an organic solvent to the plate and mixing so as to obtain a concentration at which the sugar chain adsorbs to a solid phase, wherein the concentration at which the sugar chain adsorbs to the solid phase is 80 to 90% in the organic solvent; and wherein the step optionally comprises the steps C-3) to C-6):

C-3) a step of providing a solid phase carrier-enclosed plate;

C-4) a step of activating the solid phase carrier-enclosed plate according to the phase of the solid phase carrier-enclosed plate, and washing the solid phase carrier-enclosed plate;

C-5) a step of adding the tagged sugar chain sample solution to the solid phase carrier-enclosed plate, and conditioning the tagged sugar chain sample solution to a solvent having a polarity appropriate for the phase of the solid phase carrier-enclosed plate;

C-6) a step of recovering the tagged sugar chain sample solution by suction from the solid phase carrier-enclosed plate to a second plate for recovery; and when subjecting the tagged sugar chain sample solution to MALDI-TOF MS, comprising the following step (C-7):

C-7) a step of mixing the tagged sugar chain sample solution with a matrix for mass spectrometry, and dotting the mixture on a plate for MALDI-TOF MS determination; and D) a step of conducting an analysis of the sugar chain to be determined.

2. The method according to claim 1, wherein the preceding steps are associated with at least any one of the following conditions:

A) in the sugar chain releasing step of releasing a sugar chain in a sample to prepare a sugar chain sample for analysis:

A-1) the sample is a body fluid, a cell extract or a tissue extract;

A-2) the solubilizing agent is 1-propanesulfonic acid, 2-hydroxy-3-lauramide (PHL), 1-propanesulfonic acid, 2-hydroxy-3-myristamide (PHM), 2-hydroxy-3-sulfopropyl laurate (HSD) or an equivalent thereto, and the reaction condition is at 25° C. to 42° C.;

A-3) the reducing agent is dithiothreitol (DTT), TCEP (Tris(2-carboxyethyl)phosphine hydrochloride solution, 0.5 M), or an equivalent thereto, and the reaction condition is at room temperature to 80° C.;

A-4) the —SH protecting agent is iodoacetamide (IAA) or an equivalent thereto, and the reaction condition is at 20 to 37° C. in the dark;

A-5) the proteolytic enzyme is trypsin, chymotrypsin or an equivalent thereto, and the reaction condition is at 25 to 42° C.;

A-6) the conditions for deactivating include heating to 65° C. or higher;

A-7) the sugar chain releasing enzyme is peptide-N-glycosidase F, peptide-N4-(acetyl-β-glucosaminyl)-asparagine amidase (PNGaseF), Endo H or an equivalent thereto, and the reaction conditions for the sugar chain releasing enzyme are at 25° C. to 42° C.; with regard to the step (B), B-1) the bead is a bead or magnetic bead having a sugar chain capturing group which includes an aminooxy group, an N-alkylaminooxy group, a hydrazide group, an azide group, a thiosemicarbazide group, a cysteine residue or a derivative thereof bound thereto, and the conditions in which the released sugar chain in the sample binds to the bead are at 25 to 80° C.;

B-2) the denaturing agent is guanidine hydrochloride, urea, sodium dodecyl sulfate or an equivalent thereto, and the reaction conditions involve adding at room temperature, and maintaining the temperature to allow the bead to sufficiently swell (from 10 seconds to 5 minutes);

B-3) the washing is performed using water;

B-4) the sugar chain capturing agent on the bead is an aminooxy group, an N-alkylaminooxy group, a hydrazide group, an azide group, a thiosemicarbazide group, a cysteine residue or a derivative thereof, and the salt releasing agent is triethylamine or an equivalent thereto in the case of hydrazide, and is triethylamine or an equivalent thereto in the case of an N-alkylaminooxy group;

B-5) the protective agent is acetic anhydride, succinic anhydride or another acid anhydride, or an equivalent thereto, and the reaction conditions use acetic anhydride/methanol at 15 to 37° C.;

B-6) the acid is hydrochloric acid or another inorganic acid, or an equivalent acid at pH 2 to 3;

B-7) the step includes steps of adding a hydrophilic organic solvent and discarding the hydrophilic organic solvent before adding the organic reaction solvent, and the hydrophilic organic solvent is methanol, ethanol, acetonitrile, or acetone, while the organic reaction solvent is dioxane, acetonitrile, tetrahydrofuran or an equivalent thereto;

B-8) the step of removing the solvent and the moisture in the bead includes wiping of the bottom of the plate with a filter paper, a blotting paper, a gauze, a towel, a hand towel, a tissue paper or a cotton sheet;

B-9) the methyl esterifying agent is methyl-p-tolyl-triazene (MTT) or an equivalent thereto, and the reaction conditions use 100 mM MTT/dioxane at 20 to 80° C. for 30 minutes to 5 hours;
- B-10) the organic reaction solvent is dioxane, acetonitrile, tetrahydrofuran or an equivalent thereto;
- B-11) the washing is performed using at least one selected from the group consisting of methanol, a NaCl solution and water; and
- B-12) the tagging is carried out, such that the tagging is performed using a chromophore capable of absorbing ultraviolet and visible rays, a tag having a structure emitting fluorescence, an affinity tag having a molecule capable of interacting with another molecule, a tag having a functional group capable of specifically reacting with a functional group, a tag having a functional group in a hydrophobic structure, or a tag having a metal ion ligand, and the tagging is conducted by adding acetic acid, acetonitrile, an acetate buffer or an equivalent thereto; and
- B-13) the dissolving of the tagged captured sugar chain sample is performed using water, an aqueous solution or an equivalent thereto;
C) in the step of producing a plate for mass spectrometry having the captured sugar chain sample dotted thereon;
- C-1) the disposing on the plate for recovery is conducted under the conditions of removing the reagent for tagging;
- C-3) the solid phase carrier-enclosed plate is of multi-well type and includes a surface of a resin or membrane suitable for solid phase extraction;
- C-4) when the solid phase carrier-enclosed plate is in normal phase mode, washing is conducted sequentially with water and acetonitrile, and when the solid phase carrier-enclosed plate is in reverse phase mode, washing is conducted sequentially with a lower alcohol such as methanol and water;
- C-5) the solvent having an opposite polarity is a hydrophobic organic solvent in the case of the normal phase mode, and is a hydrophilic solvent in the case of the reverse phase mode;
- C-6) the second plate for recovery is of multi-well type and includes a surface of a resin or membrane suitable for solid phase extraction; and
- C-7) the matrix for mass spectrometry is 2,5-dihydroxybenzoic acid or an equivalent thereto, and the dotting of the tagged sugar chain sample solution on the matrix for mass spectrometry is conducted in mixture or in sequence, and is diluted as necessary;
D) the analysis of the sugar chain to be determined is conducted by high performance liquid chromatography (HPLC), liquid chromatography-electrospray ionization mass spectrometry (LC-ESI MS), matrix assisted laser desorption ionization-Time-of-Flight (MALDI-TOF), or an equivalent thereto, while when using a coloring reagent or biotin in the tagging, a step of removing any excess coloring reagent is carried out as necessary, and
when the beads are magnetic beads, the magnetic beads are beads having a modifiable functional group, a hydrazide group or an aminooxy group.

3. The method according to claim 1, further comprising at least one step among the following steps:
A) a sugar chain releasing step of releasing a sugar chain in a sample, the step comprising the following steps:
- A-1) a step of providing blood serum as a sample on a filter plate;
- A-2) a step of adding 1-propanesulfonic acid, 2-hydroxy-3-lauramide (PHL) or 1-propanesulfonic acid, 2-hydroxy-3-myristamide (PHM)/ammonium bicarbonate, and allowing the mixture to react for 5 to 60 minutes at 25 to 42° C.;
- A-3) a step of adding dithiothreitol (DTT) to the sample, allowing the mixture to react for 10 to 60 minutes at 50 to 80° C., and then cooling the reaction mixture to room temperature;
- A-4) a step of adding iodoacetamide (IAA), and allowing the mixture to react for 0.5 to 2 hours at room temperature in the dark;
- A-5) a step of adding trypsin to the sample, and allowing the mixture to react for 30 to 120 minutes at 25 to 42° C.;
- A-6) a step of heating the sample to 80 to 100° C. for 1 to 10 minutes, and then cooling the sample to room temperature; and
- A-7) a step of adding PNGaseF, and allowing the mixture to react for 6 to 24 hours at 25 to 42° C.;
B) a detection sample preparing step of preparing the released sugar chain for use in detection, the step comprising the following steps:
- B-1) a step of contacting the captured sugar chain sample prepared in the step (A) with beads for capturing sugar chain, to thereby allow binding at 40° C. or higher (for example, 80° C.), and thus producing a captured sugar chain sample;
- B-2) a step of adding guanidine hydrochloride to the captured sugar chain sample to thereby place the captured sugar chain sample under a reaction condition, and then discarding the reaction liquid by suction;
- B-3) a step of washing the captured sugar chain sample with water, and then discarding the water by suction;
- B-4) a step of washing the captured sugar chain sample with triethylamine, and then discarding the triethylamine by suction;
- B-5) a step of adding acetic anhydride to the captured sugar chain sample to thereby place the captured sugar chain sample under the reaction conditions of using 10% acetic anhydride/methanol at room temperature for 10 minutes to 2 hours, and then discarding the acetic anhydride by suction;
- B-6) a step of adding hydrochloric acid to the captured sugar chain sample, and discarding the hydrochloric acid by suction;
- B-7) a step of adding methanol to the captured sugar chain sample, discarding the methanol by suction, and then adding dioxane to the captured sugar chain sample;
- B-8) a step of wiping the bottom of the filter plate with a cotton sheet;
- B-9) a step of adding methyl-p-tolyl-triazene (MTT) to the captured sugar chain sample, and allowing the mixture to react for 30 to 120 minutes (for example, 60 min.) at 60° C. or higher;
- B-10) a step of adding dioxane to the captured sugar chain sample, and discarding the dioxane by suction;
- B-11) a step of washing the captured sugar chain sample sequentially with methanol, a NaCl solution and water, and then discarding the water by suction; and
- B-12) a step of adding acetic acid and acetonitrile to the captured sugar chain sample, and tagging the sugar chain in the captured sugar chain sample using aminooxytryptophanyl arginine methyl ester/water, O-benzylhydroxylamine hydrochloride/water, or anthraniloyl hydrazine/water; and B-13) a step of adding water to the tagged captured sugar chain sample to produce a tagged sugar chain sample solution;

C) a step of producing a plate for mass spectrometry having the tagged captured sugar chain sample dotted thereon, the step comprising:

C-1) a step of disposing the tagged sugar chain sample solution obtained in the step (B) on a plate for recovery;

C-2) a step of disposing the tagged sugar chain sample solution from the plate for recovery by adding acetonitrile to the plate and mixing, so as to achieve a final concentration in acetonitrile of 80 to 90%;

C-3) a step of providing a solid phase carrier-enclosed plate which is in normal phase mode;

C-4) a step of washing the solid phase carrier-enclosed plate sequentially with water and acetonitrile, and discarding water and acetonitrile by suction;

C-5) a step of adding the tagged sugar chain sample solution to the solid phase carrier-enclosed plate, discarding the liquid, washing the plate with acetonitrile, and adding 1 to 20% acetonitrile thereto;

C-6) a step of recovering the bead by suction from the solid phase carrier-enclosed plate to the second plate for recovery; and C-7) a step of adding 2,5-dihydroxybenzoic acid in 20 to 40% acetonitrile, to the tagged sugar chain sample solution, and mixing and dotting the mixture; and D) a step of performing mass spectrometry by MALDI-TOF MS.

4. The method according to claim 3, wherein the sugar chain-capturing bead is a magnetic bead, and separation is conducted by means of a magnetic field instead of the discarding by suction.

* * * * *

UNITED STATES PATENT AND TRADEMARK OFFICE
CERTIFICATE OF CORRECTION

| | | |
|---|---|---|
| PATENT NO. | : 8,877,454 B2 | Page 1 of 1 |
| APPLICATION NO. | : 12/681573 | |
| DATED | : November 4, 2014 | |
| INVENTOR(S) | : Shinichiro Nishimura et al. | |

It is certified that error appears in the above-identified patent and that said Letters Patent is hereby corrected as shown below:

On the Title Page, item (73) the Assignee "Shionogi & Co. Ltd." should be changed to
--Sumitomo Bakelite Co., Ltd.--

Signed and Sealed this
Twenty-eighth Day of April, 2015

Michelle K. Lee
*Director of the United States Patent and Trademark Office*